(12) United States Patent
McGregor et al.

(10) Patent No.: US 11,890,287 B2
(45) Date of Patent: *Feb. 6, 2024

(54) THERAPEUTIC COMPOUNDS AND COMPOSITIONS FOR TREATING SOCIAL DISORDERS AND SUBSTANCE USE DISORDERS

(71) Applicant: Kinoxis Therapeutics Pty Ltd, Camberwell (AU)

(72) Inventors: Iain Stewart McGregor, Warrimoo (AU); Michael Kassiou, Lugarno (AU); Michael Thomas Bowen, Cammeray (AU); Callum Hicks, Philadelphia, PA (US); William Jorgensen, Casula (AU)

(73) Assignee: Kinoxis Therapeutics Pty Ltd, Camberwell (AU)

( * ) Notice: Subject to any disclaimer, the term of this patent is extended or adjusted under 35 U.S.C. 154(b) by 173 days.

This patent is subject to a terminal disclaimer.

(21) Appl. No.: 17/314,664

(22) Filed: May 7, 2021

(65) Prior Publication Data

US 2022/0362261 A1 Nov. 17, 2022

Related U.S. Application Data

(63) Continuation of application No. 15/738,532, filed as application No. PCT/AU2016/050588 on Jul. 6, 2016, now Pat. No. 11,033,555.

(30) Foreign Application Priority Data

Jul. 6, 2015 (AU) .............................. 2015902659

(51) Int. Cl.

| | | |
|---|---|---|
| C07D 487/04 | (2006.01) | |
| A61K 31/5517 | (2006.01) | |
| A61P 25/30 | (2006.01) | |
| A61P 25/32 | (2006.01) | |
| A61P 25/36 | (2006.01) | |
| A61P 25/22 | (2006.01) | |
| A61K 31/4745 | (2006.01) | |
| A61K 31/553 | (2006.01) | |
| A61K 31/554 | (2006.01) | |
| C07D 498/04 | (2006.01) | |
| C07D 513/04 | (2006.01) | |

(52) U.S. Cl.
CPC ...... *A61K 31/5517* (2013.01); *A61K 31/4745* (2013.01); *A61K 31/553* (2013.01); *A61K 31/554* (2013.01); *A61P 25/22* (2018.01); *A61P 25/30* (2018.01); *C07D 487/04* (2013.01); *C07D 498/04* (2013.01); *C07D 513/04* (2013.01)

(58) Field of Classification Search
CPC ... C07D 487/04; A61K 31/5517; A61P 25/30; A61P 25/32; A61P 25/36
See application file for complete search history.

(56) References Cited

U.S. PATENT DOCUMENTS

2022/0288060 A1 9/2022 Bowen et al.

FOREIGN PATENT DOCUMENTS

| EP | 1512687 A1 | 3/2005 |
|---|---|---|
| WO | WO 2005/023812 A2 | 3/2005 |
| WO | WO 2003/000692 A2 | 3/2006 |
| WO | WO 2006/021213 A2 | 3/2006 |
| WO | WO 2007/050353 A2 | 5/2007 |
| WO | WO 2010/097576 A1 | 9/2010 |
| WO | WO-2017004674 A1 | 1/2017 |

OTHER PUBLICATIONS

CAS Registry No. 877927-94-4, Mar. 23, 2006, 2 pages.
Chemical Catalog Registry 1780762-56-2, entered STN Jun. 15, 2015, copyright 2016.
An, X. L. et al., "Strain and Sex Differences in Anxiety-Like and Social Behaviors in C57BL/6J and BALB/cJ Mice," Exp. Anim. 60(2):111-123 (2011).
Brodkin, E. S., "BALB/c mice: Low sociability and other phenotypes that may be relevant to autism," Behavioural Brain Research, 176:53-65 (2007).
Frantz, M. C. et al., "Subtlety of the Structure-Affinity and Structure-Efficacy Relationships around a Nonpeptide Oxytocin Receptor Agonist," J. Med. Chem., 53:1546-1562 (2010).
Heinla, I. et al., "Behavioural characterization of C57BL/6N and BALB/c female mice in social home cage—Effect of mixed housing in complex environment," Physiology & Behavior, 188:32-41 (2018).
Jorgensen, W. T. et al., "Flexible analogues of WAY-267,464: Synthesis and pharmacology at the human oxytocin and vasopressin $1_a$ receptors," European Journal of Medicinal Chemistry, 108:730-740 (2016).
Karpenko, I. A. et al., "Selective Nonpeptidic Fluorescent Ligands for Oxytocin Receptor: Design, Synthesis, and Application to Time-Resolved FRET Binding Assay," J. Med. Chem., 58:2547-2552 (2015).

(Continued)

*Primary Examiner* — Brenda L Coleman
(74) *Attorney, Agent, or Firm* — COOLEY LLP; Matthew Pavao

(57) ABSTRACT

Disclosed herein are compounds, compositions and methods for the treatment of neurological, psychiatric disorders which are characterized by a fundamental disruption of social behaviour, and substance use disorders. In particular, disclosed herein are compounds of Formula (I), or salts or prodrugs thereof. Methods of treating or preventing neurological, psychiatric disorders and substance use disorders, using compounds of Formula (I), or salts and prodrugs are also disclosed.

18 Claims, 20 Drawing Sheets

(56) References Cited

OTHER PUBLICATIONS

Koob, G. F. & Volkow, N. D., "Neurobiology of addiction: a neurocircuitry analysis," Lancet Psychiatry, 3(8):760-773 (2016).
Ottoni O. et al. "Efficient and Simple Methods for the Introduction of the Sulfonyl, Acyl and Alkyl Protecting Groups on the Nitrogen of Indole and its Derivatives", Tetrahedron, vol. 54, p. 13915-13928 (1998).
Reekie, T. A. et al., "Pyrazolo[1,4]diazepines as non-peptidic probes of the oxytocin and vasopressin receptors," Tetrahedron Letters 55:4569-4571, 2014.
Reekie, T. A. et al., "Synthesis of Biologically Active Seven-Membered-Ring Heterocycles," Synthesis, 45:3211-3227 (2013).
Sankoorikal, G. M. V. et al., "A Mouse Model System for Genetic Analysis of Sociability: C57BL/6J Versus BALB/cJ Inbred Mouse Strains," Biol Psychiatry, 59:415-423 (2006).
Koob et al., "Neurocircuitry of Addiction", Neuropsychopharmacology Reviews, 2010, 35: 217-238.

THERAPEUTIC COMPOUNDS AND COMPOSITIONS FOR TREATING SOCIAL DISORDERS AND SUBSTANCE USE DISORDERS

CROSS-REFERENCE TO RELATED APPLICATIONS

This application is a continuation of U.S. patent application Ser. No. 15/738,532, filed on Dec. 20, 2017, now U.S. Pat. No. 11,033,555, issued on Jun. 15, 2021), which is a U.S. National Phase application, filed under 35 U.S.C. § 371(c), of International Application No. PCT/AU2016/050588, filed Jul. 6, 2016. which claims priority from Australian Provisional Patent Application 2015902659 filed on 6 Jul. 2015. The contents of which is each of these applications are herein incorporated herein by reference in their entirety.

TECHNICAL FIELD

The present disclosure relates to compounds, compositions and methods for the treatment of neurological, psychiatric disorders which are characterised by a fundamental disruption of social behaviour, and substance use disorders. In a specific embodiment, this disclosure relates to the treatment of neurological, psychiatric disorders and substance use disorders, using compounds of Formula (I), or salts and prodrugs of compounds of Formula (I).

BACKGROUND

Many psychiatric disorders are characterised by a fundamental disruption of social behaviour. Common examples include autism spectrum disorder (ASD) and social anxiety disorder (SAD). Additionally, several disorders have social withdrawal as a secondary symptom; examples include schizophrenia, major depressive disorder (MDD) and substance use disorders. At present there are no approved medications that directly target social deficits, and drug-treatments for these disorders, where available, have at best limited efficacy.

Recent preclinical research shows remarkable therapeutic potential of the neuropeptide oxytocin in stimulating social behaviour and in reducing drug and alcohol self-administration. However, oxytocin itself shows poor penetration of the blood brain barrier, negligible oral bioavailability and a short half-life in vivo. Due to these issues, clinical studies employing intranasal oxytocin have yielded only modest benefits in clinical populations. Therefore small molecules able to stimulate brain oxytocin systems with far greater efficacy could have widespread therapeutic applications in the aforementioned disorders.

The aforementioned disorders are among the most prevalent diseases and are some of the largest contributors to global burden of disease. A recent study by the Centre for Disease Control (USA) estimates the prevalence of autism among 8 year olds to be 1 in 110. SAD is the second most prevalent anxiety disorder, with the NIH estimating some 6.8% of American adults suffer from the disorder.

According to the World Health Organization (WHO), schizophrenia affects some 24 million people worldwide and has one of the highest levels of chronicity of any disease. The WHO also estimate that alcohol abuse contributed to over 3 million deaths worldwide in the year 2012 (5.9% of all deaths). In the developed world psychoactive substance abuse accounts for 33.4% of total years of life lost for males.

The idea to specifically target the neural substrates of social behaviour represents a paradigm shift from existing therapies for the above disorders. For example, the use of antipsychotics in ASD (e.g. risperidone) is aimed at inhibiting aggressive and challenging behaviours rather than stimulating prosocial behaviours. The use of antidepressants in SAD (e.g. paroxetine or venlafaxine) assumes that low mood and generalized anxiety are primary drivers of social withdrawal in SAD and seeks to indirectly influence social anxiety through improving mood and decreasing global anxiety. Treatment of schizophrenia with antipsychotics (e.g. olanzapine or aripiprazole) seeks to control positive symptoms and, to a certain extent, neurocognitive impairment, but does not directly tackle the pervasive social withdrawal seen in the chronic disease state.

Current treatments for addictions provide either a substitute version of the abused drug (e.g. methadone, buprenorphine or varenicline) to control craving, or a therapeutic that may decrease craving through largely unknown mechanisms (e.g. acamprosate, naltrexone, baclofen or ondansetron). These current pharmacotherapies for addiction have limited efficacy at best, and none are aimed at the debilitating social dysfunction caused by these diseases. Although there are a number of psychological therapies for these disorders, their success is also limited.

The disclosed compounds of Formula (I), and salts and prodrugs thereof, have been developed to directly target social dysfunction by acting on brain regions known to be involved in the acute and long-term regulation of social behaviour, in order to try and produce a long-term shift in social motivation that may far outlast the duration of drug treatment, representing a "state change". In other words, the compounds have been developed to recalibrate the social behaviour of an individual to a higher level as a result of treatment. In treating substance abuse, the inventors believe that a lasting increase in social motivation may re-orientate behaviour around social rewards rather than the destructive cycle of drug-seeking behaviour.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY OF THE INVENTION

In a first aspect provided herein is a compound of Formula (I), or a salt or prodrug thereof:

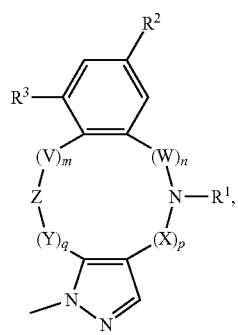

Formula (I)

wherein:
- V is NH, $CH_2$ or a direct bond;
- W is NH, $CH_2$ or a direct bond;
- X is NH, $CH_2$ or a direct bond;
- Y is NH, $CH_2$ or a direct bond;
- Z is selected from: NH, O, S, S(O), $SO_2$ or a direct bond;
- $R^1$ is selected from H or $C(O)R^4$;
- $R^2$ is selected from: H, OH, halogen, an optionally substituted $C_{1-5}$alkyl or an optionally substituted $OC_{1-5}$alkyl;
- $R^3$ is selected from: H, OH, halogen, an optionally substituted $C_{1-5}$alkyl or an optionally substituted $OC_{1-5}$alkyl;
- $R^4$ is an optionally substituted $C_{1-5}$alkyl;
- m is 0 or 1;
- n is 0 or 1;
- p is 0 or 1; and
- q is 0 or 1.

In a second aspect, provided herein is a pharmaceutical composition comprising a pharmaceutically acceptable compound, or a pharmaceutically acceptable salt or prodrug thereof, according to the first aspect, and a pharmaceutically acceptable carrier, diluent or excipient.

In a third aspect, provided herein is a method of treating or preventing a condition in a subject, the method comprising a step of administrating: a pharmaceutically acceptable compound, or a pharmaceutically acceptable salt or prodrug thereof, according to the first aspect; or a pharmaceutical composition according to the second aspect.

In a fourth aspect, provided herein is use of: a pharmaceutically acceptable compound, or a pharmaceutically acceptable salt or prodrug thereof, according to the first aspect; or a pharmaceutical composition according to the second aspect, for treating or preventing a condition in a subject.

In a fifth aspect, provided herein is use of: a pharmaceutically acceptable compound, or a pharmaceutically acceptable salt or prodrug thereof, according to the first aspect; or a pharmaceutical composition according to the second aspect, in the manufacture of a medicament for treating or preventing a condition in a subject.

DETAILED DESCRIPTION OF THE INVENTION

Figure 1:
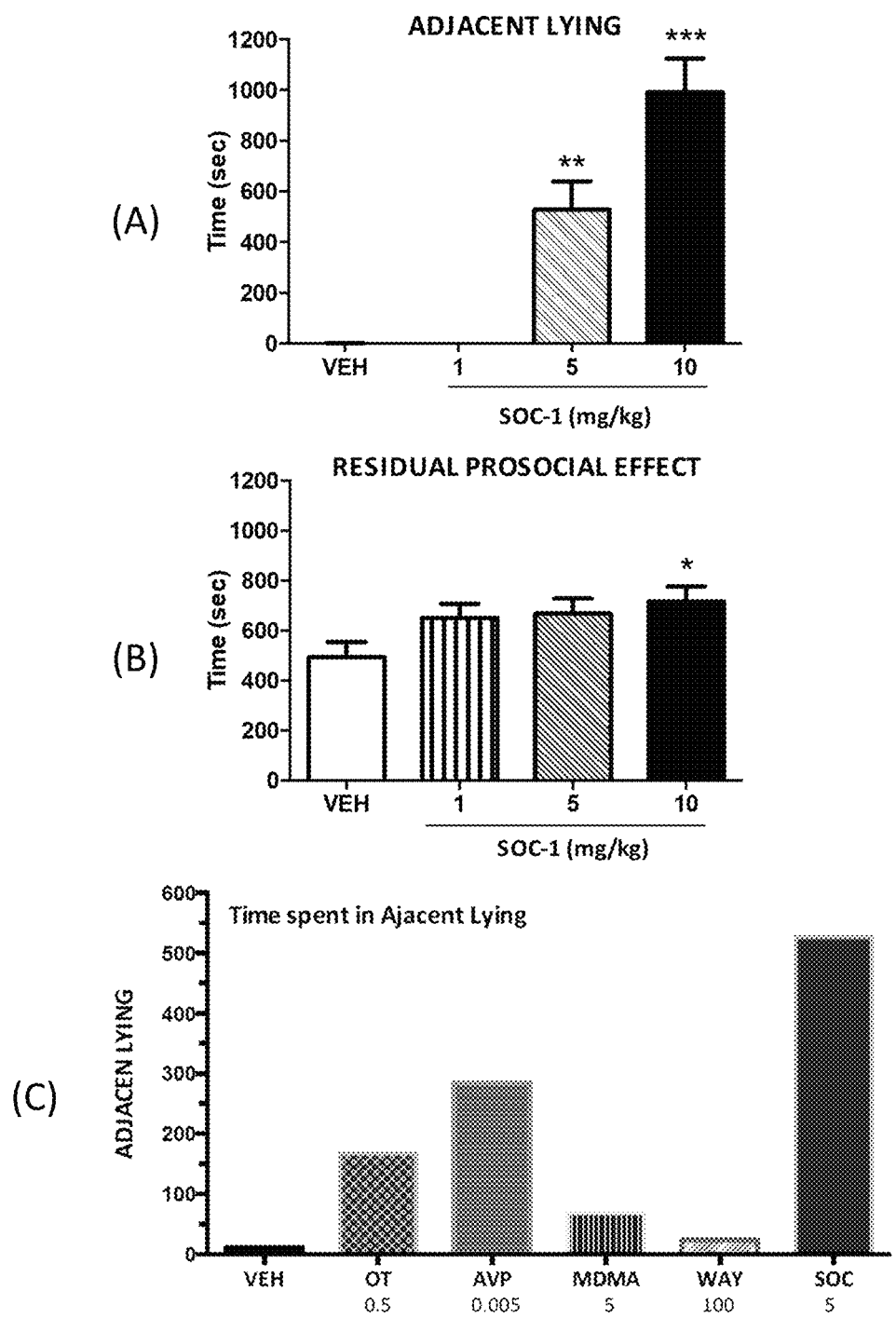
FIG. 1—Image (A) displays the results of a social interaction test for male Hooded Wistar rats given various doses of SOC-1 intraperitoneally (IP); image (B) shows the residual prosocial effect of various doses of SOC-1 in the Hooded Wistar rats in a social interaction test; and image (C) shows comparative results of adjacent lying in the social interaction test with Hooded Wistar rats given: vehicle (VEH); oxytocin (OT) (0.5 mg/kg); arginine vasopressin (AVP) (0.005 mg/kg); 3,4-methylenedioxy-methamphetamine (MDMA) (5 mg/kg); WAY 267,464 (100 mg/kg); or SOC-1 (5 mg/kg).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims. Furthermore, unless otherwise required by context, singular terms shall include pluralities and plural terms shall include the singular.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 5, 5.5 and 6. This applies regardless of the breadth of the disclosed range. Where specific values are required, these will be indicated in the specification.

As used herein, the term "$C_{1-5}$ alkyl" either used alone or in compound terms, refers to monovalent straight chain or branched hydrocarbon groups, having 1 to 5 carbon atoms. As understood by a person skilled in the art, the term "$C_{1-5}$alkyl" means an alkyl chain with 1, 2, 3, 4 or 5 carbon atoms or a range comprising any of two of those integers including 1-2, 1-3, 1-4, 1-5, 2-3, 2-4, 2-5, 3-4, 3-5 and 4-5. Suitable alkyl groups include, but are not limited to: methyl, ethyl, propyl, isopropyl, n-butyl, sec-butyl, tert-butyl, n-pentyl, neopentyl, iso-pentyl and tert-pentyl. The $C_{1-4}$alkyl may be optionally substituted with one or more substituents. The substituents may be in any position of the carbon chain. Suitable substituents include, but are not limited to: OH, $NH_2$, halogen, $NH(C_{1-5}alkyl)$, $N(C_{1-5}alkyl)_2$, CN, $NO_2$, $CO_2H$, or $OC_{1-5}alkyl$.

As used herein, the term "$OC_{1-5}alkyl$" either used alone or in compound terms, refers to alkoxy groups having 1 to 5 carbon atoms. As understood by a person skilled in the art, the term "$OC_{1-5}alkyl$" means an alkoxy group with 1, 2, 3, 4 or 5 carbon atoms or a range comprising any of two of those integers and including 1-2, 1-3, 1-4, 1-5, 2-3, 2-4, 2-5, 3-4, 3-5 and 4-5. Suitable $OC_{1-5}alkyl$ groups include, but are not limited to, methoxy, ethoxy, propyloxy, isopropyloxy, n-butyloxy, sec-butyloxy, tert-butyloxy, n-pentyloxy, neopentyloxy, iso-pentyloxy and tert-pentyloxy. The $C_{1-5}$alkyl may be optionally substituted with one or more substituents. The substituents may be in any position of the carbon chain. Suitable substituents include, but are not limited to: OH, $NH_2$, halogen, $NH(C_{1-5}alkyl)$, $N(C_{1-5}alkyl)_2$, CN, $NO_2$, $CO_2H$, or $OC_{1-5}alkyl$.

As used herein, the term "halo" or "halogen" refers to fluorine (fluoro), chlorine (chloro), bromine (bromo) or iodine (iodo).

Compounds of Formula (I) and Salts or Prodrugs Thereof:

Disclosed herein are compounds of Formula (I) or salts or prodrugs thereof,

Formula (I)

wherein:
V is NH, $CH_2$ or a direct bond;
W is NH, $CH_2$ or a direct bond
X is NH, $CH_2$ or a direct bond
Y is NH, $CH_2$ or a direct bond
Z is selected from: NH, O, S, S(O), $SO_2$ or a direct bond;
$R^1$ is selected from H or $C(O)R^4$;
$R^2$ is selected from: H, OH, halogen, an optionally substituted $C_{1-5}$alkyl or an optionally substituted $OC_{1-5}$alkyl;
$R^3$ is selected from: H, OH, halogen, an optionally substituted $C_{1-5}$alkyl or an optionally substituted $OC_{1-5}$alkyl;
$R^4$ is an optionally substituted $C_{1-5}$alkyl;
m is 0 or 1;
n is 0 or 1;
p is 0 or 1; and
q is 0 or 1.

Disclosed herein are compounds of Formula (Ia) or salts or prodrugs thereof,

Formula (Ia)

wherein:
Z is selected from: NH, O, S, S(O) or $SO_2$;
$R^1$ is selected from H or $C(O)R^4$;
$R^2$ is selected from: H, OH, halogen, an optionally substituted $C_{1-5}$alkyl or an optionally substituted $OC_{1-5}$alkyl;
$R^3$ is selected from: H, OH, halogen, an optionally substituted $C_{1-5}$alkyl or an optionally substituted $OC_{1-5}$alkyl; and
$R^4$ is an optionally substituted $C_{1-5}$alkyl.

Disclosed herein are compounds of Formula (Ib) or salts or prodrugs thereof,

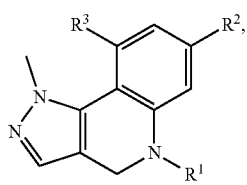

Formula (Ib)

wherein:
R¹ is selected from H or C(O)R⁴;
R² is selected from: H, OH, halogen, an optionally substituted $C_{1-5}$alkyl or an optionally substituted $OC_{1-5}$alkyl;
R³ is selected from: H, OH, halogen, an optionally substituted $C_{1-5}$alkyl or an optionally substituted $OC_{1-5}$alkyl; and
R⁴ is an optionally substituted $C_{1-5}$alkyl.

Disclosed herein are compounds of Formula (Ic) or salts or prodrugs thereof,

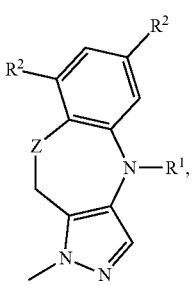

Formula (Ic)

wherein:
Z is selected from: NH, O, S, S(O) or $SO_2$;
R¹ is selected from H or C(O)R⁴;
R² is selected from: H, OH, halogen, an optionally substituted $C_{1-5}$alkyl or an optionally substituted $OC_{1-5}$alkyl;
R³ is selected from: H, OH, halogen, an optionally substituted $C_{1-5}$alkyl or an optionally substituted $OC_{1-5}$alkyl; and
R⁴ is an optionally substituted $C_{1-5}$alkyl.

Disclosed herein are compounds of Formula (Id) or salts or prodrugs thereof,

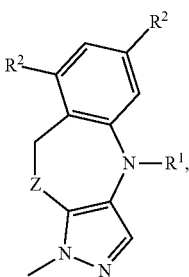

Formula (Id)

wherein:
Z is selected from: NH, O, S, S(O) or $SO_2$;
R¹ is selected from H or C(O)R⁴;
R² is selected from: H, OH, halogen, an optionally substituted $C_{1-5}$alkyl or an optionally substituted $OC_{1-5}$alkyl;
R³ is selected from: H, OH, halogen, an optionally substituted $C_{1-5}$alkyl or an optionally substituted $OC_{1-5}$alkyl; and
R⁴ is an optionally substituted $C_{1-5}$alkyl.

Disclosed herein are compounds of Formula (Ie) or salts or prodrugs thereof,

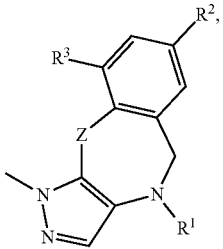

Formula (Ie)

wherein:
Z is selected from: NH, O, S, S(O) or $SO_2$;
R¹ is selected from H or C(O)R⁴;
R² is selected from: H, OH, halogen, an optionally substituted $C_{1-5}$alkyl or an optionally substituted $OC_{1-5}$alkyl;
R³ is selected from: H, OH, halogen, an optionally substituted $C_{1-5}$alkyl or an optionally substituted $OC_{1-5}$alkyl; and
R⁴ is an optionally substituted $C_{1-5}$alkyl Disclosed herein are compounds of Formula (If) or salts or prodrugs thereof,

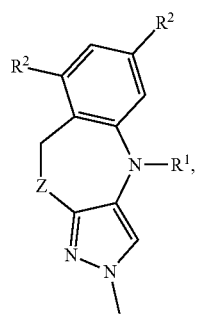

Formula (If)

wherein:
Z is selected from: NH, O, S, S(O) or $SO_2$;
R¹ is selected from H or C(O)R⁴;
R² is selected from: H, OH, halogen, an optionally substituted $C_{1-5}$alkyl or an optionally substituted $OC_{1-5}$alkyl;
R³ is selected from: H, OH, halogen, an optionally substituted $C_{1-5}$alkyl or an optionally substituted $OC_{1-5}$alkyl; and
R⁴ is an optionally substituted $C_{1-5}$alkyl.

In one embodiment the compound of Formula (I) is a compound of Formula (Ia), or a salt or prodrug thereof.

In one embodiment the compound of Formula (I) is a compound of Formula (Ib), or a salt or prodrug thereof.

In one embodiment the compound of Formula (I) is a compound of Formula (Ic), or a salt or prodrug thereof.

In one embodiment the compound of Formula (I) is a compound of Formula (Id), or a salt or prodrug thereof.

In one embodiment the compound of Formula (I) is a compound of Formula (Ie), or a salt or prodrug thereof.

In one embodiment the compound of Formula (I) is a compound of Formula (If), or a salt or prodrug thereof.

In one embodiment V is NH.
In one embodiment V is $CH_2$.
In one embodiment V is a direct bond;
In one embodiment W is NH.
In one embodiment W is $CH_2$.
In one embodiment W is a direct bond.
In one embodiment X is NH.
In one embodiment X is $CH_2$.
In one embodiment X is a direct bond
In one embodiment Y is NH.
In one embodiment Y is $CH_2$.
In one embodiment Y is a direct bond
In one embodiment Z is NH.
In one embodiment Z is O.
In one embodiment Z is S.
In one embodiment Z is S(O).
In one embodiment Z is $SO_2$.
In one embodiment Z is a direct bond.
In one embodiment $R^1$ is hydrogen.
In one embodiment $R^1$ is $C(O)R^4$. For example, $R^4$ may be an optionally substituted $C_{1-5}$ alkyl selected from: methyl, ethyl, propyl, isopropyl, n-butyl, sec-butyl, tert-butyl, n-pentyl, neopentyl, iso-pentyl and tert-pentyl groups. In one embodiment $R^4$ is an optionally substituted methyl.

In one embodiment $R^2$ is hydrogen.
In one embodiment $R^2$ is a hydroxyl group.
In one embodiment $R^2$ is a halogen. For example, in one embodiment $R^2$ is fluorine. In another embodiment $R^2$ is chlorine.

In one embodiment $R^2$ is an optionally substituted $C_{1-5}$ alkyl. For example, $R^2$ may be an optionally substituted $C_{1-5}$ alkyl selected from: methyl, ethyl, propyl, isopropyl, n-butyl, sec-butyl, tert-butyl, n-pentyl, neopentyl, iso-pentyl and tert-pentyl. In one embodiment $R^2$ is be an optionally substituted methyl.

In one embodiment $R^2$ is an optionally substituted $OC_{1-5}$ alkyl. For example, $R^2$ may be an optionally substituted $OC_{1-5}$ alkyl selected from: methoxy, ethoxy, propyloxy, isopropyloxy, n-butyloxy, sec-butyloxy, tert-butyloxy, n-pentyloxy, neopentyloxy, iso-pentyloxy and tert-pentyloxy groups. In one embodiment $R^2$ is an optionally substituted methoxy group.

In one embodiment $R^3$ is hydrogen.
In one embodiment $R^3$ is a hydroxyl group.
In one embodiment $R^3$ is a halogen. For example, in one embodiment $R^3$ is fluorine. In another embodiment $R^3$ is chlorine.

In one embodiment $R^3$ is an optionally substituted $C_{1-5}$ alkyl. For example, $R^3$ may be an optionally substituted $C_{1-5}$ alkyl selected from: methyl, ethyl, propyl, isopropyl, n-butyl, sec-butyl, tert-butyl, n-pentyl, neopentyl, iso-pentyl and tert-pentyl. In one embodiment $R^3$ is be an optionally substituted methyl.

In one embodiment $R^3$ is an optionally substituted $OC_{1-5}$ alkyl. For example, $R^3$ may be an optionally substituted $OC_{1-5}$ alkyl selected from: methoxy, ethoxy, propyloxy, isopropyloxy, n-butyloxy, sec-butyloxy, tert-butyloxy, n-pentyloxy, neopentyloxy, iso-pentyloxy and tert-pentyloxy groups. In one embodiment $R^3$ is an optionally substituted methoxy group.

In one embodiment the compound of Formula (I) is selected from:

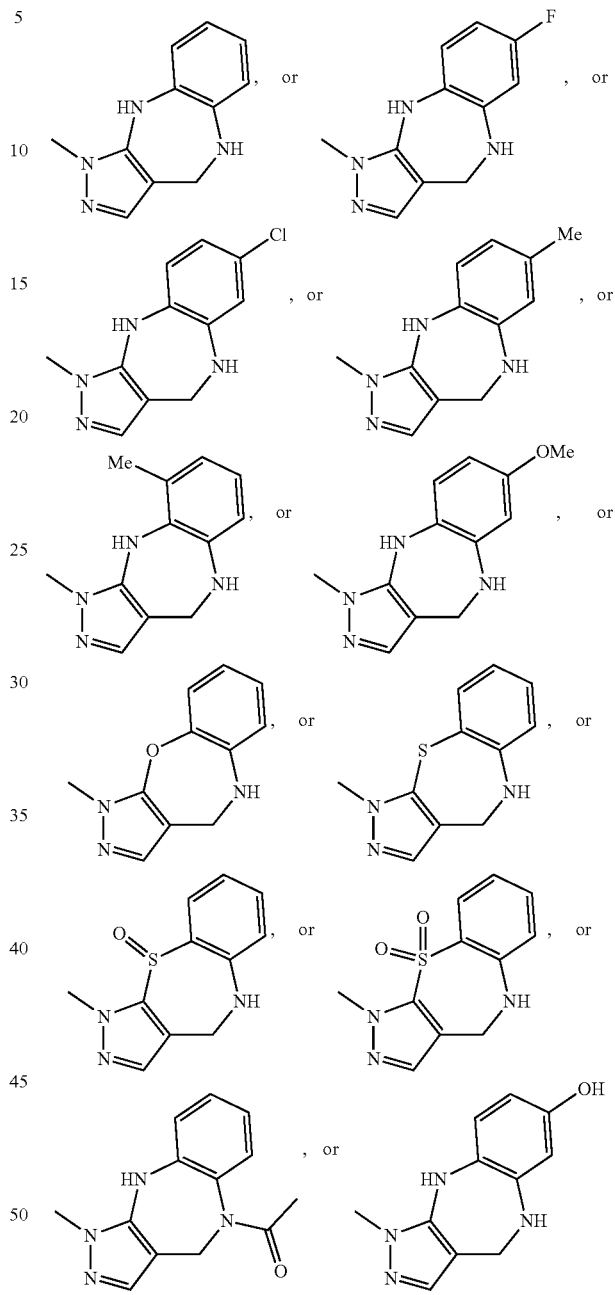

or a salt or prodrug thereof.

In another embodiment, the compound of Formula (I) is selected from:

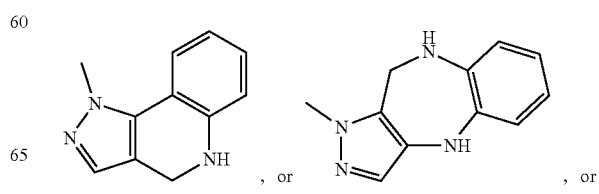

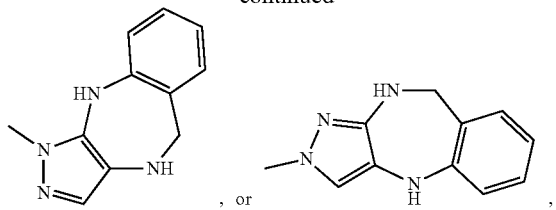

or a salt or prodrug thereof.

In another embodiment compound of Formula (I) is selected from:

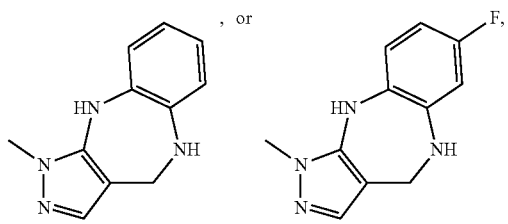 [SMILES: Cn1ncc2c1Nc1ccccc1NC2 ; Cn1ncc2c1Nc1ccc(F)cc1NC2]

or a salt or prodrug thereof. For example, in one embodiment the compound of Formula (I) is:

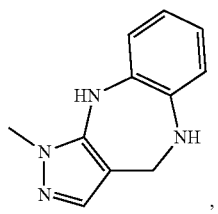

or a salt or prodrug thereof. In another embodiment, the compound of Formula (I) is:

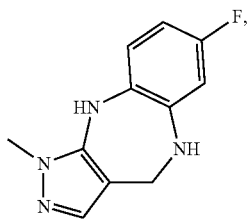

or a salt or prodrug thereof.

In one embodiment the compound of Formula (I), or a salt or prodrug thereof, is pharmaceutically acceptable.

In one embodiment the compound of Formula (I) is a compound of Formula (Ia), or a salt or prodrug thereof, and is pharmaceutically acceptable.

In one embodiment the compound of Formula (I) is a compound of Formula (Ib), or a salt or prodrug thereof, and is pharmaceutically acceptable.

In one embodiment the compound of Formula (I) is a compound of Formula (Ic), or a salt or prodrug thereof, and is pharmaceutically acceptable.

In one embodiment the compound of Formula (I) is a compound of Formula (Id), or a salt or prodrug thereof, and is pharmaceutically acceptable.

In one embodiment the compound of Formula (I) is a compound of Formula (Ie), or a salt or prodrug thereof, and is pharmaceutically acceptable.

In one embodiment the compound of Formula (I) is a compound of Formula (II), or a salt or prodrug thereof, and is pharmaceutically acceptable.

The compounds of Formula (I), or salts or prodrugs thereof, may be pharmaceutically acceptable, but it will be appreciated that non-pharmaceutically acceptable compounds, salts and prodrugs also fall within the scope of the present invention, since these are useful as intermediates in the preparation of pharmaceutically acceptable compounds, salts and prodrugs.

In one embodiment the compound of Formula (I) is a salt, for example a pharmaceutically acceptable salt.

In one embodiment the compound of Formula (I) is a compound of Formula (Ia) and is a salt, for example a pharmaceutically acceptable salt.

In one embodiment the compound of Formula (I) is a compound of Formula (Ib) and is a salt, for example a pharmaceutically acceptable salt.

In one embodiment the compound of Formula (I) is a compound of Formula (Ic) and is a salt, for example a pharmaceutically acceptable salt.

In one embodiment the compound of Formula (I) is a compound of Formula (Id) and is a salt, for example a pharmaceutically acceptable salt.

In one embodiment the compound of Formula (I) is a compound of Formula (Ie) and is a salt, for example a pharmaceutically acceptable salt.

In one embodiment the compound of Formula (I) is a compound of Formula (II) and is a salt, for example a pharmaceutically acceptable salt.

Suitable pharmaceutically acceptable salts include, but are not limited to: salts of pharmaceutically acceptable inorganic acids such as: hydrochloric, sulfuric, phosphoric, nitric, carbonic, boric, sulfamic, and hydrobromic acids; or salts of pharmaceutically acceptable organic acids such as acetic, propionic, butyric, tartaric, maleic, hydroxymaleic, fumaric, isethionic, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids.

Base salts include, but are not limited to: those formed with pharmaceutically acceptable cations, such as: sodium, potassium, lithium, calcium, magnesium, zinc, ammonium and alkylammonium; salts formed from triethylamine; alkoxyammonium salts such as those formed with ethanolamine; and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, $1^{st}$ edition, 2002, Wiley-VCH.

Basic nitrogen-containing groups in Formula (I) (or basic nitrogen-containing groups in a compound of Formula (Ia), Formula (Ib), Formula (Ic), Formula (Id), Formula (Ie), or Formula (II)), may be quaternised with such agents as lower alkyl halide, such as methyl, ethyl, propyl, and butyl chlorides, bromides and iodides; dialkyl sulfates like dimethyl and diethyl sulfate; and others known in the art.

In one embodiment the compound of Formula (I) is a salt of a compound selected from:

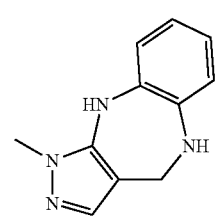 , or 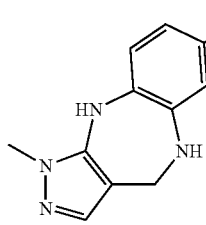 , or

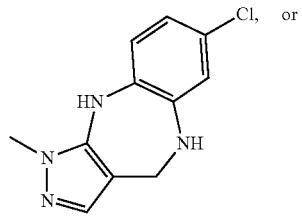 , or

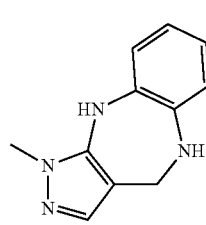 , or 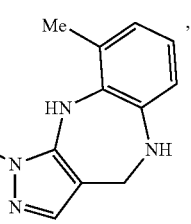 , or

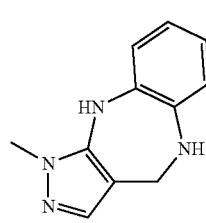 , or 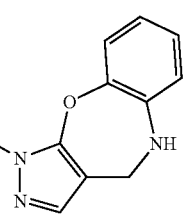 , or

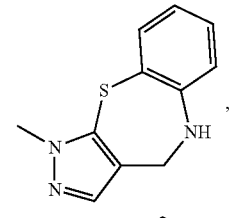 , or 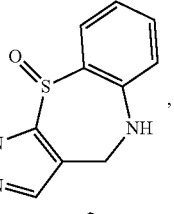 , or

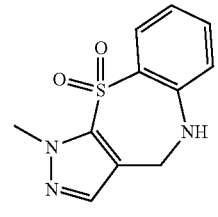 , or 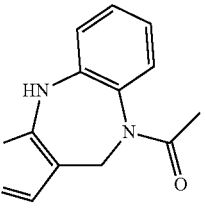 , or

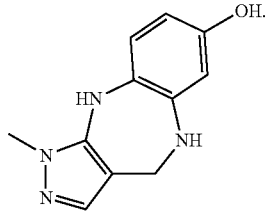 .

In another embodiment, the compound of Formula (I) is a salt of a compound selected from:

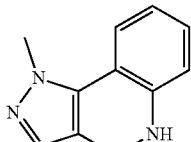 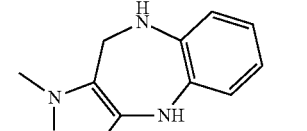 , or

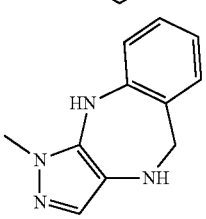 , or 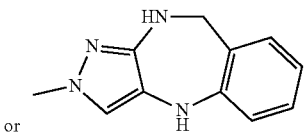 .

In another embodiment, the compound of Formula (I) is a salt of a compound selected from:

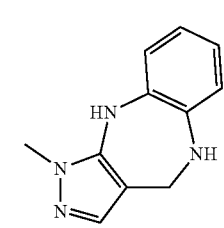 , or 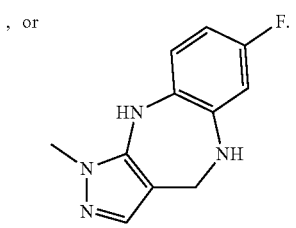 .

For example, in one embodiment, the salt of a compound of Formula (I) is a salt of

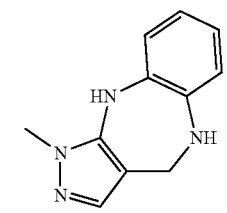

Whilst, in yet another embodiment, the salt of a compound of Formula (I) is a salt of

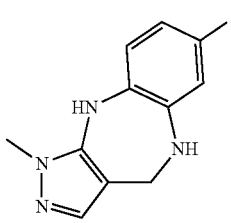

In one embodiment the compound of Formula (I) is a hydrochloride salt.

In one embodiment the compound of Formula (I) is a compound of Formula (Ia) in the form of a hydrochloride salt, for example a pharmaceutically acceptable hydrochloride salt.

In one embodiment the compound of Formula (I) is a compound of Formula (Ib) in the form of a hydrochloride salt, for example a pharmaceutically acceptable hydrochloride salt.

In one embodiment the compound of Formula (I) is a compound of Formula (Ic) in the form of a hydrochloride salt, for example a pharmaceutically acceptable hydrochloride salt.

In one embodiment the compound of Formula (I) is a compound of Formula (Id) is a hydrochloride salt, for example a pharmaceutically acceptable hydrochloride salt.

In one embodiment the compound of Formula (I) is a compound of Formula (Ie) in the form of a hydrochloride salt, for example a pharmaceutically acceptable hydrochloride salt.

In one embodiment the compound of Formula (I) is a compound of Formula (If) in the form of a hydrochloride salt, for example a pharmaceutically acceptable hydrochloride salt.

In one embodiment the compound of Formula (I) is a hydrochloride salt of a compound selected from:

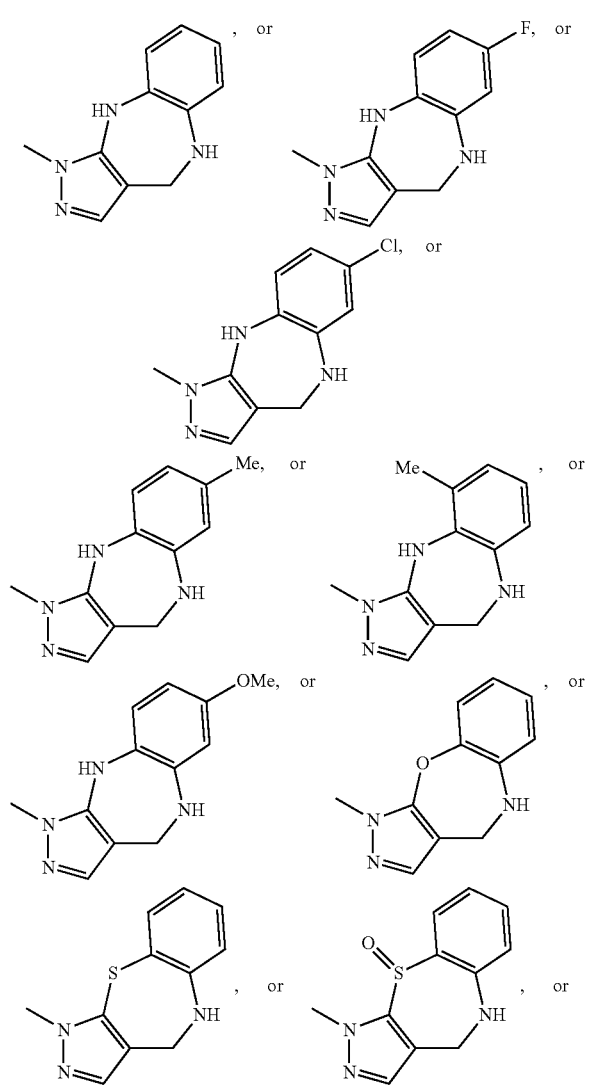

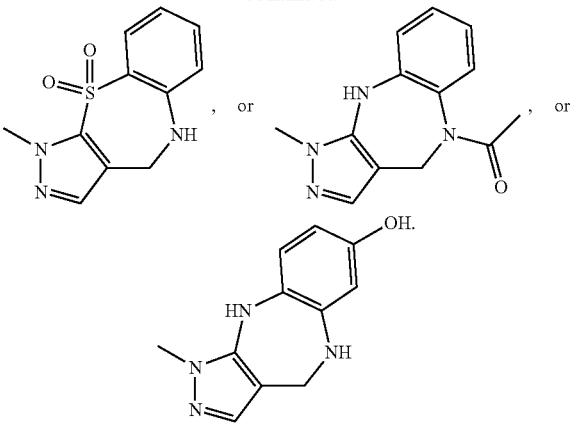

In another embodiment, the compound of Formula (I) is a hydrochloride salt of a compound selected from:

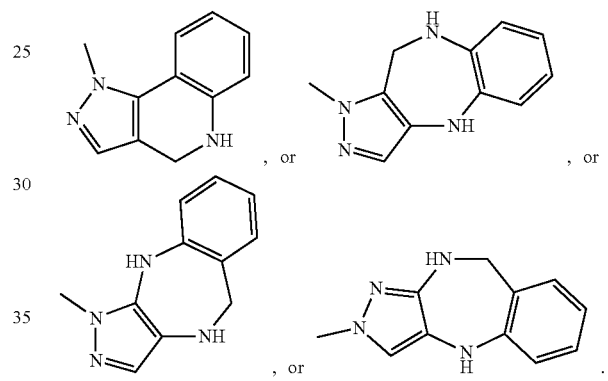

In another embodiment, the compound of Formula (I) is a hydrochloride salt of a compound selected from:

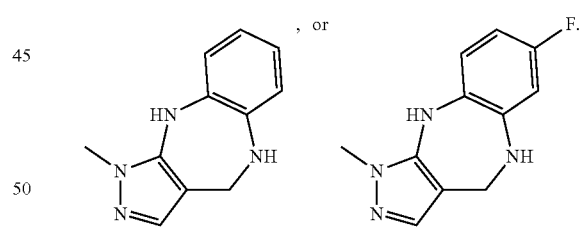

For example, in one embodiment, the salt of a compound of Formula (I) is a hydrochloride salt of

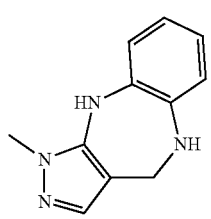

Whilst, in yet another embodiment, the salt of a compound of Formula (I) is a hydrochloride salt of

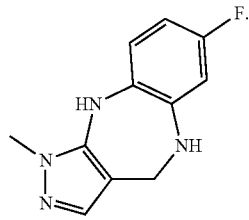 [SMILES: Cn1ncc2c1Nc1ccc(F)cc1NC2]

In one embodiment the compound of Formula (I) is a prodrug.

In one embodiment the compound of Formula (Ia) is a prodrug.

In one embodiment the compound of Formula (Ib) is a prodrug.

In one embodiment the compound of Formula (Ic) is a prodrug.

In one embodiment the compound of Formula (Id) is a prodrug.

In one embodiment the compound of Formula (Ie) is a prodrug.

In one embodiment the compound of Formula (If) is a prodrug.

Prodrugs include compounds wherein an amino acid residue, or a polypeptide chain of two or more (e.g., two, three or four) amino acid residues which are covalently joined to free amino, hydroxy and carboxylic acid groups of compounds of Formula (I). The amino acid residues include the 20 naturally occurring amino acids commonly designated by three letter symbols and also include: 4-hydroxyproline, hydroxylysine, demosine, isodemosine, 3-methylhistidine, norvaline, beta-alanine, gamma-aminobutyric acid, citrulline, homocysteine, homoserine, ornithine and methionine sulfone. Prodrugs also include compounds wherein carbonates, carbamates, amides and alkyl esters, which may be covalently bonded to the above substituents of Formula (I) through the carbonyl carbon prodrug side chain. Prodrugs also include phosphate derivatives of compounds of Formula (I) (such as acids, salts of acids, or esters) joined through a phosphorus-oxygen bond to a free hydroxyl of compounds of Formula (I).

Pharmaceutical Compositions

Disclosed herein are pharmaceutical compositions comprising a compound of Formula (I) or a salt or prodrug thereof, and a pharmaceutically acceptable carrier, diluent or excipient. In one embodiment, the compound of Formula (I), or a salt or prodrug thereof, is pharmaceutically acceptable.

As used herein, "pharmaceutically acceptable carrier, diluent or excipient" includes excipients or agents such as solvents, diluents, dispersion media, coatings, antibacterial and antifungal agents, isotonic and absorption delaying agents and the like that are physiologically compatible and are not deleterious to a compound as described herein or use thereof. The use of such carriers and agents to prepare compositions of pharmaceutically active substances is well known in the art (see, for example *Remington: The Science and Practice of Pharmacy,* 21st Edition; Lippincott Williams & Wilkins: Philadelphia, PA, 2005).

The pharmaceutically acceptable composition may be diluted prior to use. Suitable diluents may be selected from, for example: Ringer's solution, Hartmann's solution, dextrose solution, saline solution and sterile water for injection.

The term "composition" as used herein is intended to encompass a product comprising the specified ingredients in the specified amounts, as well as any product which results, directly or indirectly, from combination of the specified ingredients in the specified amounts.

Herein, "pharmaceutically acceptable" means that compounds of Formula (I), or a salt or prodrugs thereof, along with carriers, diluents or excipient, must be compatible with the other ingredients of the formulation and not deleterious to the recipient thereof. The compounds of Formula (I), or a salt or prodrug thereof, should be able to contact tissues of a recipient without excessive toxicity, irritation, allergic response or other potential complications commensurate with a reasonable benefit/risk ratio identified by a skilled medical professional or veterinarian. In addition a compound of Formula (I), or a drug or prodrug thereof, should be compatible with a carrier and/or excipient in any composition that is to be delivered as a medicament to an individual, for example to an animal or human being.

It will be appreciated that in some cases the compounds of Formula (I), or a salt or prodrug thereof are non-pharmaceutically acceptable and these fall within the scope of the present invention. However, in order for use in pharmaceutical formulations, in some embodiments the compounds of Formula (I), or a salt or prodrug thereof, are pharmaceutically acceptable compounds. Non-pharmaceutically acceptable compounds of Formula (I), or a salt or prodrug thereof, may be useful in the preparation of pharmaceutically acceptable compounds of Formula (I), or a salt or prodrug thereof.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.), according to techniques such as those well known in the art of pharmaceutical formulation.

The compounds of Formula (I), or a salt or prodrug thereof, defined herein may be administered by any suitable means, for example, parenterally, such as by subcutaneous, intraperitoneal, intravenous, intramuscular, or intracisternal injection or infusion techniques (e.g., as sterile injectable aqueous or non-aqueous solutions or suspensions).

Pharmaceutical formulations include those for oral, rectal, nasal, topical (including buccal and sub-lingual), parenteral administration (including intramuscular, intraperitoneal, sub-cutaneous and intravenous), or in a form suitable for administration by inhalation or insufflation. The compounds of Formula (I), or a salt or prodrug thereof, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, or in the form of sterile injectable solutions for parenteral (including subcutaneous) use.

The pharmaceutical compositions for the administration of the compounds of this invention may conveniently be presented in dosage unit form and may be prepared by any of the methods well known in the art of pharmacy. All methods include the step of bringing the active ingredient, for example a compound defined by Formula (I), or a salt or prodrug thereof, into association with the carrier which constitutes one or more accessory ingredients. In general, the pharmaceutical compositions are prepared by uniformly and intimately bringing the active ingredient, for example a compound defined by Formula (I), or a salt or prodrug thereof, into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

The pharmaceutical compositions and methods disclosed herein may further comprise other therapeutically active compounds which are usually applied in the treatment of the disclosed disorders or conditions. Selection of the appropriate agents for use in combination therapy may be made by one of ordinary skill in the art, according to conventional pharmaceutical principles. The combination of therapeutic agents may act synergistically to effect the treatment or prevention of the various disorders or conditions disclosed herein. Using this approach, one may be able to achieve therapeutic efficacy with lower dosages of each agent, thus reducing the potential for adverse side effects.

When other therapeutic agents are employed in combination with a compound of Formula (I), or a salt or prodrug thereof, they may be used for example in amounts as noted in the Physician Desk Reference (PDR) or as otherwise determined by one of ordinary skill in the art.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods of Treatment

Disclosed herein are methods of treating or preventing a condition in a subject, the method comprising a step of administrating: a pharmaceutically acceptable amount of a compound of Formula (I), or a pharmaceutically acceptable salt or prodrug thereof, or a pharmaceutical composition as defined herein, to the subject.

Also disclosed herein is use of a pharmaceutically acceptable compound of Formula (I), or a pharmaceutically acceptable salt or prodrug thereof, or a pharmaceutical composition as defined herein, for treating or preventing a condition in a subject.

Also disclosed herein is use of a pharmaceutically acceptable compound of Formula (I), or a pharmaceutically acceptable salt or prodrug thereof, in the manufacture of a medicament for treating or preventing a condition in a subject.

In one embodiment a compound of Formula (I), or a salt or prodrug thereof, is used as a medicament.

In one embodiment a compound of Formula (Ia), or a salt or prodrug thereof, is used as a medicament.

In one embodiment a compound of Formula (Ib), or a salt or prodrug thereof, is used as a medicament.

In one embodiment a compound of Formula (Ic), or a salt or prodrug thereof, is used as a medicament.

In one embodiment a compound of Formula (Id), or a salt or prodrug thereof, is used as a medicament.

In one embodiment a compound of Formula (Ie), or a salt or prodrug thereof, is used as a medicament.

In one embodiment a compound of Formula (If), or a salt or prodrug thereof, is used as a medicament.

Compounds of Formula (I), or a salt or prodrug thereof, may be provided in an "effective amount", for example when an appropriate compound is added to a pharmaceutical composition. "Effective amount" is taken to mean an amount of a compound that will elicit a desired biological or medical response of a tissue, system, animal or human that is being sought by the researcher, veterinarian, medical doctor or other clinician administering the compound of a composition comprising the compound.

The "effective amount" will be dependent on a number of factors, including the efficacy of the particular compound. The subject's weight and age may also be a factor for the person skilled in the art when determining the concentration of compound that the subject should receive.

The phrases "administration of" and or "administering a" compound should be understood to mean providing a compound of Formula (I) (or a compound of Formula (Ia), or Formula (Ib), or Formula (Ic), or Formula (Id), or Formula (Ie), or Formula (IQ), or a salt or prodrug thereof, to a subject in need of treatment.

The recipients of a compound of Formula (I) or a pharmaceutically acceptable salt or prodrug thereof; or a pharmaceutical composition comprising a compound of Formula (I) or a pharmaceutically acceptable salt or prodrug thereof, can be human beings, male or female.

Alternatively the recipients of: a compound of Formula (I) or a pharmaceutically acceptable derivative, salt or prodrug thereof; or a pharmaceutical composition comprising a compound of Formula (I) or a pharmaceutically acceptable derivative, salt or prodrug thereof can also be a non-human animal. "Non-human animals" or "non-human animal" is directed to the kingdom Animalia, excluding humans, and includes both vertebrates and invertebrates, male or female, and comprises: warm blooded animals, including mammals (comprising but not limited to primates, dogs, cats, cattle, pigs, sheep, goats, rats, guinea pigs, horses, or other bovine, ovine, equine, canine, feline, rodent or murine species), birds, insects, reptiles, fish and amphibians.

The recipients of the compounds and pharmaceutically acceptable compositions are referred herein with the interchangeable terms "patient", "recipient" "individual", and "subject". These four terms are used interchangeably and refer to any human or animal (unless indicated otherwise), as defined herein.

In one embodiment: a compound of Formula (I), or a salt or prodrug thereof; or a pharmaceutical composition comprising a compound of Formula (I), or a salt or prodrug thereof, is used to stimulate prosocial behaviour in a subject.

In one embodiment: a compound of Formula (I), or a salt or prodrug thereof; or a pharmaceutical composition comprising a compound of Formula (I), or a salt or prodrug thereof, is used to provide acute and long-term regulation of social behaviour in a subject.

In one embodiment: a compound of Formula (I), or a salt or prodrug thereof; or a pharmaceutical composition comprising a compound of Formula (I), or a salt or prodrug thereof, is used to treat a substance abuse disorder. For example, a compound of Formula (I), or a salt or prodrug thereof; or a pharmaceutical composition comprising a compound of Formula (I), or a salt or prodrug thereof may be used to treat an individual abusing drugs. Examples of drugs include, but are not limited to opiates and stimulants. Specific examples of drugs include, but are not limited to cocaine, methamphetamine and cannabis. Alternatively, a compound of Formula (I), or a salt or prodrug thereof; or a pharmaceutical composition comprising a compound of Formula (I), or a salt or prodrug thereof may be used to treat an individual abusing alcohol.

In one embodiment: a compound of Formula (I), or a salt or prodrug thereof; or a pharmaceutical composition comprising a compound of Formula (I), or a salt or prodrug thereof, is used to treat or prevent a social dysfunction. The inventors have developed the compounds disclosed herein as part of a therapy for psychiatric disorders that feature social dysfunction as a primary or secondary feature, such as an autistic spectrum disorder (ASD), a social anxiety disorder (SAD), a depressive disorder, including major depressive disorder (MDD), schizophrenia and substance use disorders.

Herein, target treatment patient populations include:

children and adults with a diagnosis of autistic spectrum disorder;

persons with a diagnosis of social anxiety disorder;

drug (e.g. opiate, stimulant, cannabis) and alcohol-dependent persons in recovery who are seeking to maintain ongoing abstinence;

persons with a diagnosis of chronic schizophrenia, where the drug may be used as an adjunct to antipsychotic medication to improve social functioning; or other persons seeking to overcome social deficits as part of a current disease state (e.g. MDD)

In one embodiment the condition being treated or prevented is a social dysfunction. For example, a social dysfunction selected from:

social withdrawal;

aggressiveness;

an anti-social disorder; or an addiction to a substance.

In one embodiment the subject has a psychiatric disorder. For example, in another embodiment the subject has a psychiatric disorder, wherein social withdrawal is a primary or secondary feature of the psychiatric disorder.

In one embodiment the subject has a psychiatric disorder selected from:

an autistic spectrum disorder;

a social anxiety disorder;

a depressive disorder, including major depressive disorder; or schizophrenia.

In one embodiment the subject suffers or is recovering from a substance abuse disorder. For example an addiction to drugs and chemical substances such as cocaine, opiates, amphetamines, heroin, ethanol and nicotine In another embodiment the subject is recovering from a substance abuse disorder and seeks to maintain ongoing abstinence of the substance.

EXAMPLE EMBODIMENTS

1. A compound of Formula (I), or a salt or prodrug thereof:

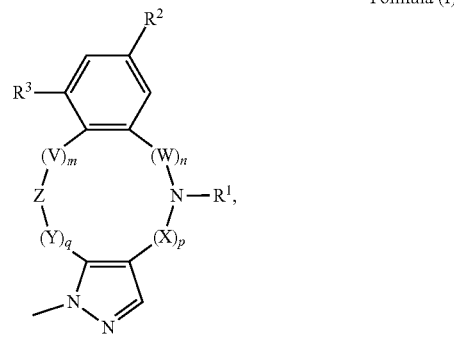

Formula (I)

wherein:

V is NH, $CH_2$ or a direct bond;

W is NH, $CH_2$ or a direct bond;

X is NH, $CH_2$ or a direct bond;

Y is NH, $CH_2$ or a direct bond;

Z is selected from: NH, O, S, S(O), $SO_2$ or a direct bond;

$R^1$ is selected from H or $C(O)R^4$;

$R^2$ is selected from: H, OH, halogen, an optionally substituted $C_{1-5}$alkyl or an optionally substituted $OC_{1-5}$alkyl;

$R^3$ is selected from: H, OH, halogen, an optionally substituted $C_{1-5}$alkyl or an optionally substituted $OC_{1-5}$alkyl;

$R^4$ is an optionally substituted $C_{1-5}$alkyl;

m is 0 or 1;

n is 0 or 1;

p is 0 or 1; and q is 0 or 1.

2. The compound according to example embodiment 1 having Formula (Ia):

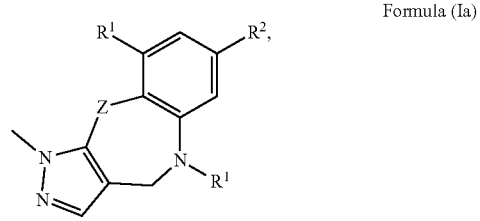

Formula (Ia)

wherein:

Z is selected from: NH, O, S, S(O) or $SO_2$;

$R^1$ is selected from H or $C(O)R^4$;

$R^2$ is selected from: H, a halogen, an optionally substituted $C_{1-5}$alkyl, or an optionally substituted $OC_{1-5}$alkyl;

$R^3$ is selected from: H, a halogen, an optionally substituted $C_{1-5}$alkyl, or an optionally substituted $OC_{1-5}$alkyl; and $R^4$ is an optionally substituted $C_{1-5}$alkyl, or a salt or prodrug thereof.

3. The compound according to example embodiment 1 having Formula (Ib):

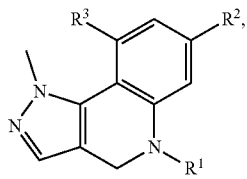

Formula (Ib)

wherein:
R$^1$ is selected from H or C(O)R$^4$;
R$^2$ is selected from: H, OH, halogen, an optionally substituted C$_{1-5}$alkyl or an optionally substituted OC$_{1-5}$alkyl;
R$^3$ is selected from: H, OH, halogen, an optionally substituted C$_{1-5}$alkyl or an optionally substituted OC$_{1-5}$alkyl; and
R$^4$ is an optionally substituted C$_{1-5}$alkyl,
or a salt or prodrug thereof.

4. The compound according to example embodiment 1 having Formula (Ic):

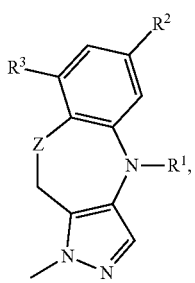

Formula (Ic)

wherein:
Z is selected from: NH, O, S, S(O) or SO$_2$;
R$^1$ is selected from H or C(O)R$^4$;
R$^2$ is selected from: H, OH, halogen, an optionally substituted C$_{1-5}$alkyl or an optionally substituted OC$_{1-5}$alkyl;
R$^3$ is selected from: H, OH, halogen, an optionally substituted C$_{1-5}$alkyl or an optionally substituted OC$_{1-5}$alkyl; and
R$^4$ is an optionally substituted C$_{1-5}$alkyl,
or a salt or prodrug thereof.

5. The compound according to example embodiment 1 having Formula (Id):

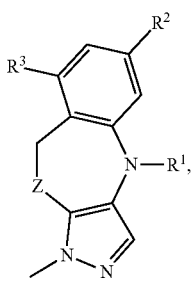

Formula (Id)

wherein:
Z is selected from: NH, O, S, S(O) or SO$_2$;
R$^1$ is selected from H or C(O)R$^4$;
R$^2$ is selected from: H, OH, halogen, an optionally substituted C$_{1-5}$alkyl or an optionally substituted OC$_{1-5}$alkyl;
R$^3$ is selected from: H, OH, halogen, an optionally substituted C$_{1-5}$alkyl or an optionally substituted OC$_{1-5}$alkyl; and
R$^4$ is an optionally substituted C$_{1-5}$alkyl,
or a salt or prodrug thereof.

6. The compound according to example embodiment 1 having Formula (Ie):

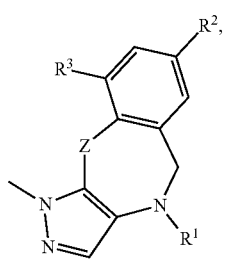

Formula (Ie)

wherein:
Z is selected from: NH, O, S, S(O) or SO$_2$;
R$^1$ is selected from H or C(O)R$^4$;
R$^2$ is selected from: H, OH, halogen, an optionally substituted C$_{1-5}$alkyl or an optionally substituted OC$_{1-5}$alkyl;
R$^3$ is selected from: H, OH, halogen, an optionally substituted C$_{1-5}$alkyl or an optionally substituted OC$_{1-5}$alkyl; and
R$^4$ is an optionally substituted C$_{1-5}$alkyl,
or a salt or prodrug thereof.

7. The compound according to example embodiment 1 having Formula (II):

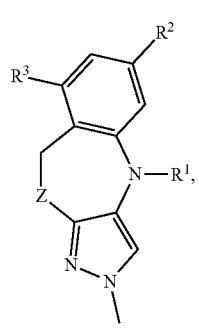

Formula (If)

wherein:
Z is selected from: NH, O, S, S(O) or SO$_2$;
R$^1$ is selected from H or C(O)R$^4$;
R$^2$ is selected from: H, OH, halogen, an optionally substituted C$_{1-5}$alkyl or an optionally substituted OC$_{1-5}$alkyl;
R$^3$ is selected from: H, OH, halogen, an optionally substituted C$_{1-5}$alkyl or an optionally substituted OC$_{1-5}$alkyl; and
R$^4$ is an optionally substituted C$_{1-5}$alkyl,
or a salt or prodrug thereof.

8. The compound, or a salt or prodrug thereof, according to any one of example embodiments 1 to 7, wherein Z is NH.
9. The compound, or a salt or prodrug thereof, according to any one of example embodiments 1 to 7, wherein Z is O.
10. The compound, or a salt or prodrug thereof, according to any one of example embodiments 1 to 7, wherein Z is S.
11. The compound, or a salt or prodrug thereof, according to any one of example embodiments 1 to 7, wherein Z is S(O).
12. The compound, or a salt or prodrug thereof, according to any one of example embodiments 1 to 7, wherein Z is $SO_2$.
13. The compound, or a salt or prodrug thereof, any one of example embodiments 1 to 12, wherein $R^1$ is hydrogen.
14. The compound, or a salt or prodrug thereof, according to any one of example embodiments 1 to 12, wherein $R^1$ is $C(O)R^4$.
15. The compound, or a salt or prodrug thereof, according to any one of example embodiments 1 to 12 or 14, wherein $R^4$ is an optionally substituted $C_{1-5}$ alkyl selected from any one of: methyl, ethyl, propyl, isopropyl, n-butyl, sec-butyl, tert-butyl, n-pentyl, neopentyl, iso-pentyl and tert-pentyl.
16. The compound, or a salt or prodrug thereof, according to any one of example embodiments 1 to 12, 14 or 15, wherein $R^4$ is an optionally substituted methyl.
17. The compound, or a salt or prodrug thereof, according to any one of example embodiments 1 to 16, wherein $R^2$ is hydrogen.
18. The compound, or a salt or prodrug thereof, according to any one of example embodiments 1 to 16, wherein $R^2$ is a hydroxyl group.
19. The compound, or a salt or prodrug thereof, according to any one of example embodiments 1 to 16, wherein $R^2$ is a halogen.
20. The compound, or a salt or prodrug thereof, according to any one of example embodiments 1 to 16 or 19, wherein $R^2$ is fluorine.
21. The compound, or a salt or prodrug thereof, according to any one of example embodiments 1 to 16 or 19, wherein $R^2$ is chlorine.
22. The compound, or a salt or prodrug thereof, according to any one of example embodiments 1 to 16, wherein $R^2$ is an optionally substituted $C_{1-5}$ alkyl.
23. The compound, or a salt or prodrug thereof, according to any one of example embodiments 1 to 16 or 22, wherein $R^2$ is an optionally substituted methyl.
24. The compound, or a salt or prodrug thereof, according to any one of example embodiments 1 to 16, wherein $R^2$ is an optionally substituted $OC_{1-5}$alkyl.
25. The compound, or a salt or prodrug thereof, according to any one of example embodiments 1 to 16 or 24, wherein $R^2$ is an optionally substituted methoxy group.
26. The compound, or a salt or prodrug thereof, according to any one of example embodiments 1 to 25, wherein $R^3$ is hydrogen.
27. The compound, or a salt or prodrug thereof, according to any one of example embodiments 1 to 25, wherein $R^3$ is a hydroxyl group.
28. The compound, or a salt or prodrug thereof, according to any one of example embodiments 1 to 25, wherein $R^3$ is a halogen.
29. The compound, or a salt or prodrug thereof, according to any one of example embodiments 1 to 25 or 28, wherein $R^3$ is fluorine.
30. The compound, or a salt or prodrug thereof, according to any one of example embodiments 1 to 25 or 28, wherein $R^3$ is chlorine.
31. The compound, or a salt or prodrug thereof, according to any one of example embodiments 1 to 25, wherein $R^3$ is an optionally substituted $C_{1-5}$ alkyl.
32. The compound, or a salt or prodrug thereof, according to any one of example embodiments 1 to 25 or 31, wherein $R^3$ is an optionally substituted methyl.
33. The compound, or a salt or prodrug thereof, according to any one of example embodiments 1 to 25, wherein $R^3$ is an optionally substituted $OC_{1-5}$alkyl.
34. The compound, or a salt or prodrug thereof, according to any one of example embodiments 1 to 25 or 33, wherein $R^3$ is an optionally substituted methoxy group.
35. The compound, or a salt or prodrug thereof, according to any one of example embodiments 1 to 34, wherein the compound is selected from any one of:

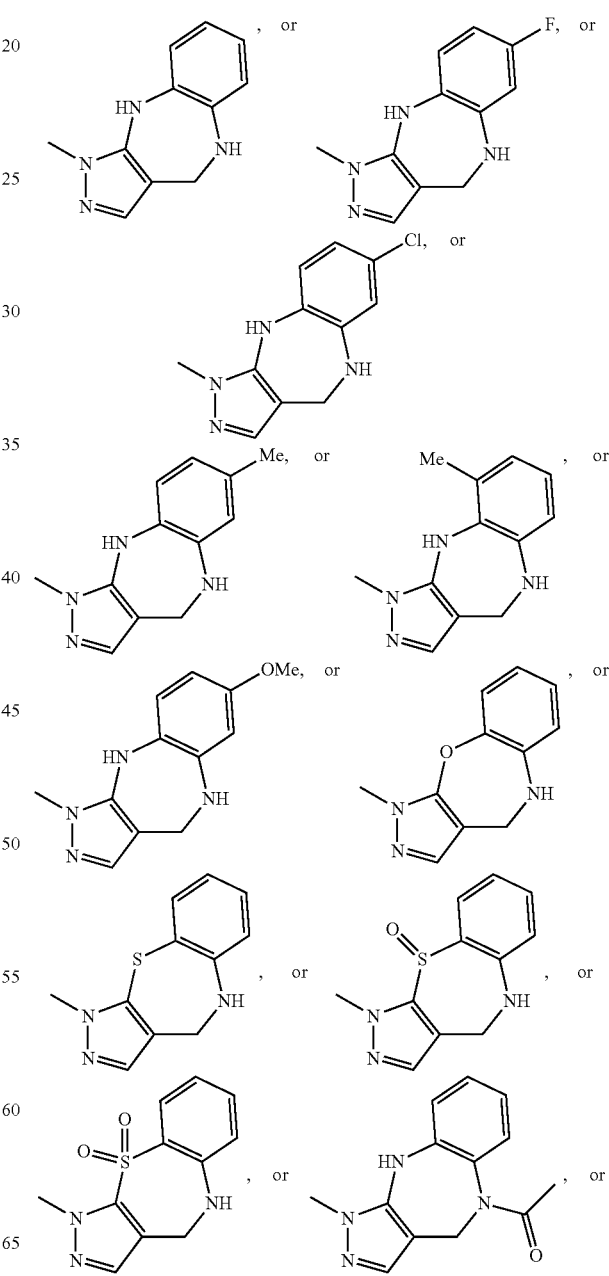

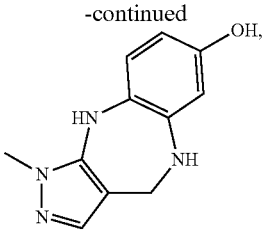

or a salt or prodrug thereof.

36. The compound, or a salt or prodrug thereof, according to any one of example embodiments 1 to 35, wherein the compound is

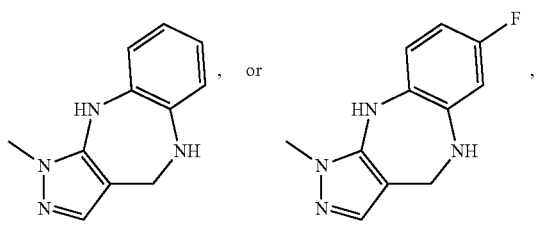 [SMILES: Cn1ncc2c1Nc1ccccc1NC2 ; Cn1ncc2c1Nc1ccc(F)cc1NC2]

or a salt or prodrug thereof.

37. The compound, or a salt or prodrug thereof, according to any one of example embodiments 1 to 36, wherein the compound is

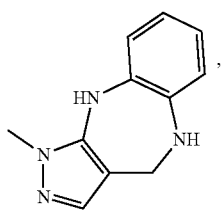

or a salt or prodrug thereof.

38. The compound, or a salt or prodrug thereof, according to any one of example embodiments 1 to 36, wherein the compound is

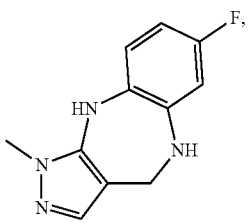 [SMILES: Cn1ncc2c1Nc1ccc(F)cc1NC2]

or a salt or prodrug thereof.

39. The compound, or a salt or prodrug thereof, according to any one of example embodiments 1 to 36, wherein the compound is selected from any one of:

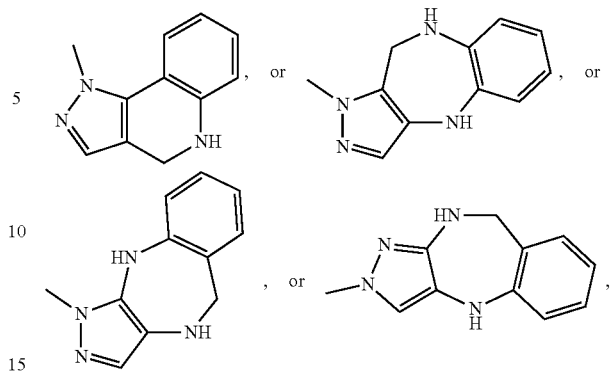

or a salt or prodrug thereof.

40. The compound, or a salt or prodrug thereof, according to any one of example embodiments 1 to 39, wherein the compound is a salt of a compound having any one of: Formula (Ia), or Formula (Ib), or Formula (Ic), or Formula (Id), or Formula (Ie), or Formula (If).

41. The compound, or a salt or prodrug thereof, according to example embodiment 40, wherein the compound is a salt of a compound having Formula (Ia).

42. The compound, or a salt or prodrug thereof, according to example embodiment 40, wherein the compound is a salt of a compound having Formula (Ib).

43. The compound, or a salt or prodrug thereof, according to example embodiment 40, wherein the compound is a salt of a compound having Formula (Ic).

44. The compound, or a salt or prodrug thereof, according to example embodiment 40, wherein the compound is a salt of a compound having Formula (Id).

45. The compound, or a salt or prodrug thereof, according to example embodiment 40, wherein the compound is a salt of a compound having Formula (Ie).

46. The compound, or a salt or prodrug thereof, according to example embodiment 40, wherein the compound is a salt of a compound having Formula (If).

47. The compound, or a salt or prodrug thereof, according to any one of example embodiments 1 to 46, wherein the compound is a salt selected from any one of: hydrochloric, sulfuric, phosphoric, nitric, carbonic, boric, sulfamic, hydrobromic acids, acetic, propionic, butyric, tartaric, maleic, hydroxymaleic, fumaric, isethionic, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acid salts; or metal salts, including sodium, potassium, lithium, calcium, magnesium and zinc metal salts; or ammonium, alkylammonium salts; or amino acid salts; or metal salts, including sodium, potassium, lithium, calcium, magnesium and zinc metal salts; or ammonium, alkylammonium salts; or amino acid salts.

48. The compound, or a salt or prodrug thereof according to any one of example embodiments 1 to 47, wherein the compound is a hydrochloric salt.

49. The compound, or a salt or prodrug thereof according to any one of example embodiments 1 to 48, wherein the salt is a hydrochloride salt of a compound selected from any one of:

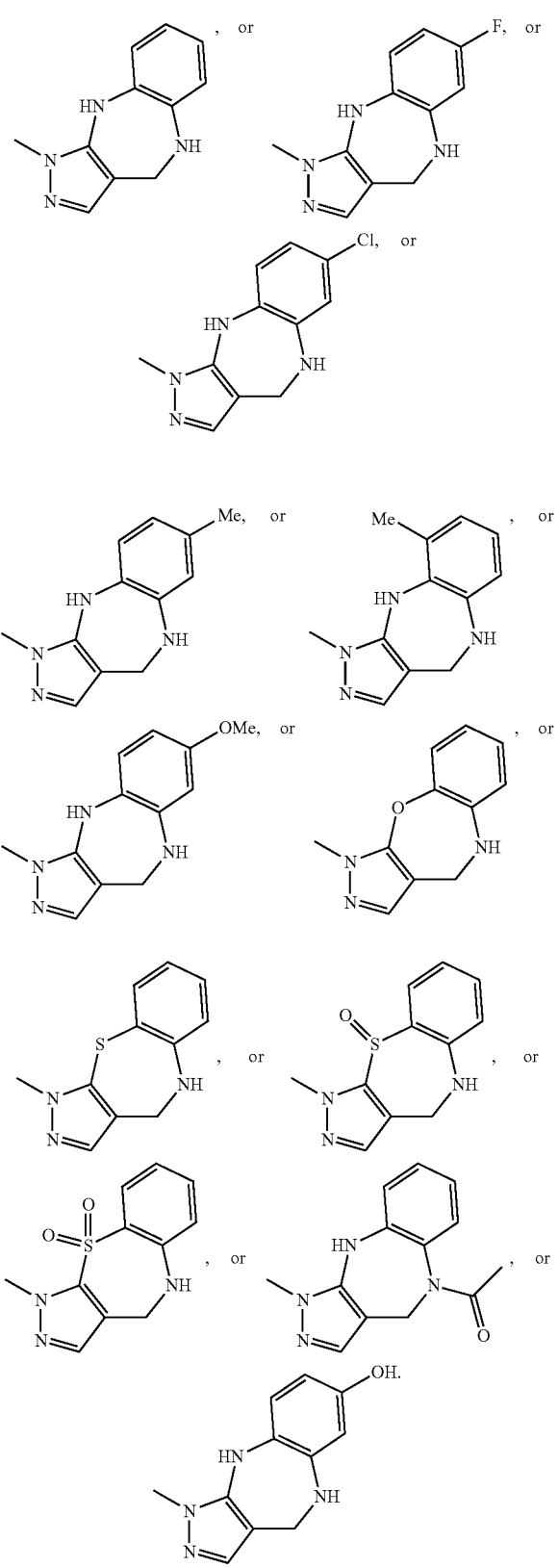

50. The compound, or a salt or prodrug thereof according to any one of example embodiments 1 to 49, wherein the salt is a hydrochloride salt of a compound selected from:

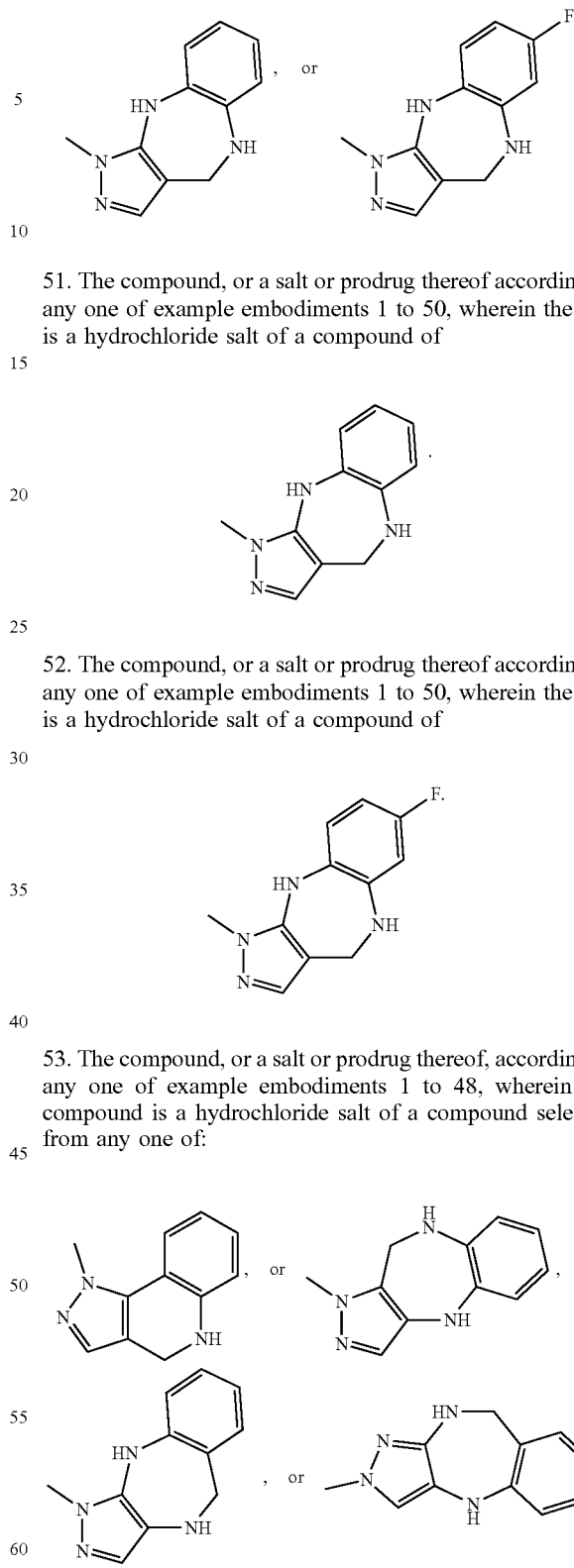

51. The compound, or a salt or prodrug thereof according to any one of example embodiments 1 to 50, wherein the salt is a hydrochloride salt of a compound of 52. The compound, or a salt or prodrug thereof according to any one of example embodiments 1 to 50, wherein the salt is a hydrochloride salt of a compound of 53. The compound, or a salt or prodrug thereof, according to any one of example embodiments 1 to 48, wherein the compound is a hydrochloride salt of a compound selected from any one of:

54. The compound, or a salt or prodrug thereof, according to any one of example embodiments 1 to 39, wherein the compound is a prodrug of a compound having Formula (Ia), or Formula (Ib), or Formula (Ic), or Formula (Id), or Formula (Ie), or Formula (If).

55. The compound, or a salt or prodrug thereof, according to example embodiment 54, wherein the compound is a prodrug of a compound having Formula (Ia).

56. The compound, or a salt or prodrug thereof, according to example embodiment 54, wherein the compound is a prodrug of a compound having Formula (Ib).

57. The compound, or a salt or prodrug thereof, according to example embodiment 54, wherein the compound is a prodrug of a compound having Formula (Ic).

58. The compound, or a salt or prodrug thereof, according to example embodiment 54, wherein the compound is a prodrug of a compound having Formula (Id).

59. The compound, or a salt or prodrug thereof, according to example embodiment 54, wherein the compound is a prodrug of a compound having Formula (Ie).

60. The compound, or a salt or prodrug thereof, according to example embodiment 54, wherein the compound is a prodrug of a compound having Formula (If).

61. The compound, or a salt or prodrug thereof, according to any one of example embodiments 1 to 60 when used as a medicament.

62. A pharmaceutical composition comprising a pharmaceutically acceptable compound, or a pharmaceutically acceptable salt or prodrug thereof, according to any one of example embodiments 1 to 60, and a pharmaceutically acceptable carrier, diluent or excipient.

63. The pharmaceutical composition of example embodiment 62, wherein the pharmaceutically acceptable compound, or a pharmaceutically acceptable salt or prodrug thereof is a compound having Formula (Ia), or a salt or prodrug thereof.

64. The pharmaceutical composition of example embodiment 62, wherein the pharmaceutically acceptable compound, or a pharmaceutically acceptable salt or prodrug thereof is a compound having Formula (Ib), or a salt or prodrug thereof.

65. The pharmaceutical composition of example embodiment 62, wherein the pharmaceutically acceptable compound, or a pharmaceutically acceptable salt or prodrug thereof is a compound having Formula (Ic), or a salt or prodrug thereof.

66. The pharmaceutical composition of example embodiment 62, wherein the pharmaceutically acceptable compound, or a pharmaceutically acceptable salt or prodrug thereof is a compound having Formula (Id), or a salt or prodrug thereof.

67. The pharmaceutical composition of example embodiment 62, wherein the pharmaceutically acceptable compound, or a pharmaceutically acceptable salt or prodrug thereof is a compound having Formula (Ie), or a salt or prodrug thereof.

68. The pharmaceutical composition of example embodiment 62, wherein the pharmaceutically acceptable compound, or a pharmaceutically acceptable salt or prodrug thereof is a compound having Formula (If), or a salt or prodrug thereof.

69. A method of treating or preventing a condition in a subject, the method comprising a step of administrating: a pharmaceutically acceptable compound, or a pharmaceutically acceptable salt or prodrug thereof, according to any one of example embodiments 1 to 60; or a pharmaceutical composition according to any one of example embodiments 62 to 68, to the subject.

70. The method of example embodiment 69, wherein the pharmaceutically acceptable compound, or a pharmaceutically acceptable salt or prodrug thereof is a compound having Formula (Ia), or a salt or prodrug thereof.

71. The method of example embodiment 69, wherein the pharmaceutically acceptable compound, or a pharmaceutically acceptable salt or prodrug thereof is a compound having Formula (Ib), or a salt or prodrug thereof.

72. The method of example embodiment 69, wherein the pharmaceutically acceptable compound, or a pharmaceutically acceptable salt or prodrug thereof is a compound having Formula (Ic), or a salt or prodrug thereof.

73. The method of example embodiment 69, wherein the pharmaceutically acceptable compound, or a pharmaceutically acceptable salt or prodrug thereof is a compound having Formula (Id), or a salt or prodrug thereof.

74. The method of example embodiment 69, wherein the pharmaceutically acceptable compound, or a pharmaceutically acceptable salt or prodrug thereof is a compound having Formula (Ie), or a salt or prodrug thereof.

75. The method of example embodiment 69, wherein the pharmaceutically acceptable compound, or a pharmaceutically acceptable salt or prodrug thereof is a compound having Formula (If), or a salt or prodrug thereof.

76. The method according to any one of example embodiments 69 to 75, wherein the condition is a social dysfunction.

77. The method according to any one of example embodiment 69 to 76, wherein the condition is a social dysfunction selected from:
   social withdrawal; or
   aggressiveness; or
   an anti-social disorder; or
   an addiction to a substance.

78. The method according to any one of example embodiments 69 to 77, wherein the subject has a psychiatric disorder.

79. The method according to example embodiment 78, wherein social withdrawal is a primary or secondary feature of the psychiatric disorder.

80. The method according to any one of example embodiments 69 to 79, wherein the subject has a psychiatric disorder selected from:
   an autistic spectrum disorder;
   a social anxiety disorder;
   a depressive disorder, including major depressive disorder; or
   schizophrenia.

81. The method according to any one of example embodiments 69 to 80, wherein the subject suffers or is recovering from a substance abuse disorder.

82. The method according to any one of example embodiments 69 to 81, wherein the subject is recovering from a substance abuse disorder and seeks to maintain ongoing abstinence of the substance.

83. Use of: a pharmaceutically acceptable compound, or a pharmaceutically acceptable salt or prodrug thereof, according to any one of example embodiments 1 to 60; or a pharmaceutical composition according to any one of example embodiments 62 to 68, for treating or preventing a condition in a subject.

84. The use of example embodiment 83, wherein the pharmaceutically acceptable compound, or a pharmaceutically acceptable salt or prodrug thereof is a compound having Formula (Ia), or a salt or prodrug thereof.

85. The use of example embodiment 83, wherein the pharmaceutically acceptable compound, or a pharmaceutically acceptable salt or prodrug thereof is a compound having Formula (Ib), or a salt or prodrug thereof.

86. The use of example embodiment 83, wherein the pharmaceutically acceptable compound, or a pharmaceutically acceptable salt or prodrug thereof is a compound having Formula (Ic), or a salt or prodrug thereof.

87. The use of example embodiment 83, wherein the pharmaceutically acceptable compound, or a pharmaceutically acceptable salt or prodrug thereof is a compound having Formula (Id), or a salt or prodrug thereof.

88. The use of example embodiment 83, wherein the pharmaceutically acceptable compound, or a pharmaceutically acceptable salt or prodrug thereof is a compound having Formula (Ie), or a salt or prodrug thereof.

89. The use of example embodiment 83, wherein the pharmaceutically acceptable compound, or a pharmaceutically acceptable salt or prodrug thereof is a compound having Formula (If), or a salt or prodrug thereof.

90. The use according to any one of example embodiments 83 to 89, wherein the condition is a social dysfunction.

91. The use according to any one of example embodiment 83 to 90, wherein the condition is a social dysfunction selected from:
- social withdrawal;
- aggressiveness;
- an anti-social disorder; or
- an addiction to a substance.

92. The use according to any one of example embodiments 83 to 91, wherein the subject has a psychiatric disorder.

93. The use according to example embodiment 92, wherein social withdrawal is a primary or secondary feature of the psychiatric disorder.

94. The use according to any one of example embodiments 83 to 93, wherein the subject has a psychiatric disorder selected from:
- an autistic spectrum disorder;
- a social anxiety disorder;
- a depressive disorder, including major depressive disorder; or
- schizophrenia.

95. The use according to any one of example embodiments 83 to 94, wherein the subject suffers or is recovering from a substance abuse disorder.

96. The use according to any one of example embodiments 83 to 95, wherein the subject is recovering from a substance abuse disorder and seeks to maintain ongoing abstinence of the substance.

97. Use of: a pharmaceutically acceptable compound, or a pharmaceutically acceptable salt or prodrug thereof, according to any one of example embodiments 1 to 60; or a pharmaceutical composition according to any one of example embodiments 62 to 68, in the manufacture of a medicament for treating or preventing a condition in a subject.

98. The use of example embodiment 97, wherein the pharmaceutically acceptable compound, or a pharmaceutically acceptable salt or prodrug thereof is a compound having Formula (Ia), or a salt or prodrug thereof.

99. The use of example embodiment 98, wherein the pharmaceutically acceptable compound, or a pharmaceutically acceptable salt or prodrug thereof is a compound having Formula (Ib), or a salt or prodrug thereof.

100. The use of example embodiment 98, wherein the pharmaceutically acceptable compound, or a pharmaceutically acceptable salt or prodrug thereof is a compound having Formula (Ic), or a salt or prodrug thereof.

101. The use of example embodiment 98, wherein the pharmaceutically acceptable compound, or a pharmaceutically acceptable salt or prodrug thereof is a compound having Formula (Id), or a salt or prodrug thereof.

102. The use of example embodiment 98, wherein the pharmaceutically acceptable compound, or a pharmaceutically acceptable salt or prodrug thereof is a compound having Formula (Ie), or a salt or prodrug thereof.

103. The use of example embodiment 98, wherein the pharmaceutically acceptable compound, or a pharmaceutically acceptable salt or prodrug thereof is a compound having Formula (If), or a salt or prodrug thereof.

104. The use according to any one of example embodiments 98 to 103, wherein the condition is a social dysfunction.

105. The use according to any one of example embodiment 98 to 104, wherein the condition is a social dysfunction selected from:
- social withdrawal;
- aggressiveness;
- an anti-social disorder; or
- an addiction to a substance.

106. The use according to any one of example embodiments 98 to 105, wherein the subject has a psychiatric disorder.

107. The use according to example embodiment 106, wherein social withdrawal is a primary or secondary feature of the psychiatric disorder.

108. The use according to any one of example embodiments 98 to 107, wherein the subject has a psychiatric disorder selected from:
- an autistic spectrum disorder;
- a social anxiety disorder;
- a depressive disorder, including major depressive disorder;
- schizophrenia.

109. The use according to any one of example embodiments 98 to 108, wherein the subject suffers or is recovering from a substance abuse disorder.

110. The use according to any one of example embodiments 98 to 109, wherein the subject is recovering from a substance abuse disorder and seeks to maintain ongoing abstinence of the substance.

111. The method according to any one of example embodiments 69 to 75, wherein the condition is a substance abuse disorder.

112. The method of example embodiment 111, wherein the substance is alcohol.

113. The method of example embodiment 111, wherein the substance is cocaine.

114. The method of example embodiment 111, wherein the substance is methamphetamines.

115. The use according to any one of example embodiments 83 to 89, wherein the condition is a substance abuse disorder.

116. The use according to example embodiment 115, wherein the substance is alcohol.

117. The use according to example embodiment 115, wherein the substance is cocaine.

118. The use according to example embodiment 115, wherein the substance is methamphetamines.

119. The use according to any one of example embodiments 97 to 103, wherein the condition is a substance abuse disorder.

120. The use according to example embodiment 119, wherein the substance is alcohol.

121. The use according to example embodiment 119, wherein the substance is cocaine.

122. The use according to example embodiment 119, wherein the substance is methamphetamines.

EXAMPLES

A selection of abbreviations used herein are shown in Table 1:

TABLE 1

A selection of abbreviations utilised in the present specification

| Abbreviation | Full Name/Description |
| --- | --- |
| APCI | Atmospheric-pressure chemical ionization |
| DCM | Dichloromethane |
| DMF | N,N-Dimethyformamide |
| DMSO | Dimethyl sulfoxide |
| ESI | Electrospray ionisation |
| EtOH | Ethanol |
| HRESIMS | High-resolution electrospray ionisation mass spectrometry |
| HRMS | High resolution mass spectrometry |
| LRMS | Low resolution mass spectrometry |
| MeOH | Methanol |
| THF | Tetrahydrofuran |
| TLC | Thin-layer chromatography |

General Details for Synthetic and Characterisation Methods

All reactions were performed under an atmosphere of nitrogen or argon unless otherwise specified. THF, toluene, and 1,4-dioxane were dried over sodium wire and distilled from, in the case of THF, sodium benzophenone ketyl, dichloromethane, methanol, ethanol, and acetonitrile were distilled from $CaH_2$. AR Grade acetone was used as purchased. Commercially available chemicals were used as purchased. Analytical thin-layer chromatography (TLC) was performed using Merck aluminium-backed silica gel 60 F254 (0.2 mm) plates which were visualized using shortwave (254 nm) and/or longwave (365 nm) UV fluorescence. Flash chromatography was performed using Merck Kieselgel 60 (230-400 mesh) silica gel. Melting points were measured in open capillaries using a Stuart SMP10 melting point apparatus and are uncorrected. Infrared absorption spectra were recorded on a Bruker Alpha FT-IR spectrophotometer, and the data are reported as vibrational frequency ($cm^{-1}$). Nuclear magnetic resonance spectra were recorded at 300 K using a Bruker Avance 200 NMR (300.1 MHz) spectrometer. The data is reported as chemical shift (δ ppm) relative to the residual protonated solvent resonance, relative integral, multiplicity (s=singlet, br s=broad singlet, d=doublet, dd=doublet of doublets, t=triplet, dt=doublet of triplets, q=quartet, sep=septet, m=multiplet), coupling constants (J Hz), and assignment. Assignment of signals was assisted by COSY, DEPT, HSQC, and HMBC experiments where necessary, relative to the residual protonated solvent resonance. Assignment of signals was assisted by COSY, DEPT, HSQC, and HMBC experiments where necessary. LRMS were recorded using electrospray ionization (ESI) or atmospheric-pressure chemical ionization (APCI) recorded on a Finnigan LCQ ion trap spectrometer.

Example 1—Synthesis of Compounds of Formula (I)

Appropriate synthetic methodologies can be found in T. A. Reekie el al., *Tetrahedron Letters*, 55, 4568-4571, 2014; and T. A. Reekie et al., *Synthesis*, 45, 3211-3227, 2013.

1-Methyl-1H-pyrazol-5-ol (1)

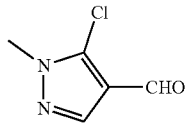

A magnetically stirred solution of methyl 3-methoxyacrylate (20.0 g, 172.2 mmol) in methanol (100 mL) was treated slowly with A-methylhydrazine (10.0 mL, 189.4 mmol) then heated at reflux for 16 hours. The resulting mixture was cooled to room temperature then concentrated under reduced pressure to afford an orange solid that was dissolved in N,N-Dimethyformamide (DMF) (19.9 mL, 258.4 mmol) and cooled to 0° C. The resulting mixture was treated slowly with phosphoryl chloride (48.1 mL, 516.6 mmol) then heated at 80° C. for 7 hours before being cooled and poured slowly into ice cold $Na_2CO_3$ (600 mL of a 20% w/v aqueous solution). The aqueous solution was then extracted with chloroform (5×100 mL) and the combined organic phases were washed with brine (1×100 mL) before being dried ($MgSO_4$), filtered and concentrated under reduced pressure to afford an orange solid. Recrystallisation (dichloromethane/hexane) afforded compound 1 (12.87 g, 52%) as yellow crystals, m.p. 77-78° C., ($R_f$=0.44 in 1:1 v/v ethyl acetate/hexane).

Characterisation data for compound 1 is shown in Table 2.

General Procedure 1

Compounds Pre-SOC-2, Pre-SOC-3, Pre-SOC-4, Pre-SOC-5 and Pre-SOC-6, were prepared via General Procedure 1, whereby a magnetically stirred solution of 1 (500 mg, 3.46 mmol) in DMF (7 mL) was treated with KOH (387 mg, 6.90 mmol) and an appropriate nitroaniline (3 equivalents, 10.38 mmol) then heated at 100° C. for 1 hour. The resulting mixture was cooled to room temperature then treated with $NH_4Cl$ (100 mL of a saturated aqueous solution) and extracted with ethyl acetate (3×25 mL). The combined organic phases were washed with brine (1×50 mL) before being dried ($MgSO_4$), filtered and concentrated under reduced pressure to afford a yellow oil. Subjection of this residue to flash column chromatography (silica, 1:4→1:1 v/v ethyl acetate/n-hexane gradient elution) and concentration of the relevant fractions afforded the target pyrazole.

General Procedure 2

Compounds FB-SOC-2, FB-SOC-4, FB-SOC-5 and FB-SOC-6 were prepared by General Procedure 2, whereby a suspension of Pre-SOC-2, Pre-SOC-4, Pre-SOC-5 or Pre-SOC-6 (1.20 mmol) and palladium on carbon (10 mg of 10% w/v) in methanol (12 mL) was stirred magnetically at room temperature under an atmosphere of $H_2$ (1 atm) for 18 hours. The resulting mixture was filtered through Celite™ and the solids thus retained were washed with methanol (3×10 mL). The combined filtrates were concentrated under reduced pressure to afford the required benzodiazepine compound.

1-Methyl-5-((2-nitrophenyl)amino)-1H-pyrazole-4-carbaldehyde (Pre-SOC-1)

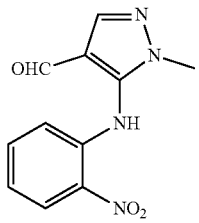 [SMILES: Cn1ncc(C=O)c1Nc1ccccc1[N+](=O)[O-]]

A magnetically stirred solution of compound 1 (5.78 g, 40.0 mmol) and 2-nitroaniline (5.52 g, 40.0 mmol) in DMF (40 mL) was treated with powdered KOH (4.49 g, 80.0 mmol) then heated at 120° C. for 2 hours. The resulting mixture was cooled to room temperature then treated with $NH_4Cl$ (500 mL of a saturated aqueous solution) and extracted with ethyl acetate (3×200 mL). The combined organic phases were washed with brine (1×100 mL) before being dried ($MgSO_4$), filtered and concentrated under reduced pressure to afford a yellow oil. Subjection of this residue to flash column chromatography (silica, 1:4→1:1 v/v ethyl acetate/hexane gradient elution) and concentration of the relevant fractions ($R_f$=0.33 in 1:1 v/v ethyl acetate/hexane) afforded the compound Pre-SOC-1 (7.38 g, 75%) as a yellow, crystalline solid, m.p. 102-105° C.

Characterisation data for compound Pre-SOC-1 is shown in Table 2.

1-Methyl-1,4,5,10-tetrahydrobenzo[b]pyrazolo[3,4-e][1,4]diazepine (FB-SOC-1)

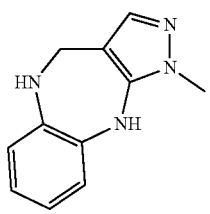

A suspension of Pre-SOC-1 (3.94 g, 16.0 mmol) and palladium on carbon (100 mg of 10% w/v) in methanol (160 mL) was stirred magnetically at room temperature under an atmosphere of $H_2$ (1 atm) for 16 hours. The resulting mixture was filtered through Celite™ and the solids thus retained were washed with methanol (3×20 mL). The combined filtrates were concentrated under reduced pressure to afford FB-SOC-1 (3.04 g, 95%) as yellow powder, m.p. 205-207° C., ($R_f$=0.43 in 1:9 v/v methanol/dichloromethane).

Characterisation data for compound FB-SOC-1 is shown in Table 2.

5-((4-Fluoro-2-nitrophenyl)amino)-1-methyl-1H-pyrazole-4-carbaldehyde (Pre-SOC-2)

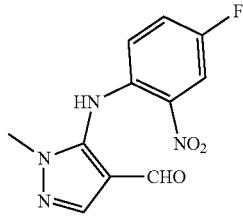 [SMILES: Cn1ncc(C=O)c1Nc1ccc(F)cc1[N+](=O)[O-]]

Pre-SOC-2 was prepared (539 mg, 59%) as an orange solid, m.p. 113-116° C., ($R_f$=0.32 in 1:1 v/v ethyl acetate/n-hexane) as per General Procedure 1 with 4-fluoro-2-nitroaniline.

Characterisation data for Pre-SOC-2 can be found in Table 2.

7-Fluoro-1-methyl-1,4,5,10-tetrahydrobenzo[b]pyrazolo[3,4-e][1,4]diazapine (FB-SOC-2)

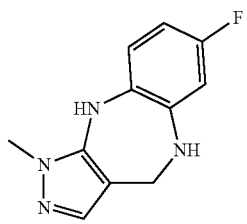 [SMILES: Cn1ncc2c1Nc1ccc(F)cc1NC2]

FB-SOC-2 was prepared (236 mg, 90%) as brown crystals, m.p. 181-183° C., ($R_f$=0.43 in 1:9 v/v methanol/dichloromethane) as per General Procedure 2.

Characterisation data for FB-SOC-2 can be found in Table 2.

5-((4-Chloro-2-nitrophenyl)amino)-1-methyl-1H-pyrazole-4-carbaldehyde (Pre-SOC-3)

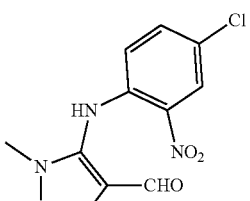

Pre-SOC-3 was prepared (563 mg, 58%) as yellow crystals, m.p. 131-132° C., ($R_f$=0.40 in 1:1 v/v ethyl acetate/n-hexane) as per General Procedure 1 with 4-chloro-2-nitroaniline.

Characterisation data for Pre-SOC-3 can be found in Table 2.

7-Chloro-1-methyl-1,4,5,10-tetrahydrobenzo[b]pyrazolo[3,4-e][1,4]diazapine (FB-SOC-3)

A magnetically stirred solution of Pre-SOC-3 (337 mg, 1.20 mmol) in methanol (12 mL) was treated with HCl (2.0 mL of a 6.0 M aqueous solution, 12.0 mmol) then Zn powder (1.57 g, 24.0 mmol). The ensuing mixture was stirred at room temperature for 1 hour then filtered through Celite™. The solids thus retained were washed with methanol (2×25 mL) and the combined filtrates concentrated under reduced pressure to give a yellow solid. Recrystallization (n-hexane/dichloromethane) afforded FB-SOC-3 (175 mg, 62%) as a brown solid, m.p. 174-176° C., ($R_f$=0.25 in 1:9 v/v methanol/dichloromethane).

Characterisation data for FB-SOC-3 can be found in Table 2.

1-Methyl-5-((4-methyl-2-nitrophenyl)amino)-1H-pyrazole-4-carbaldehyde (Pre-SOC-4)

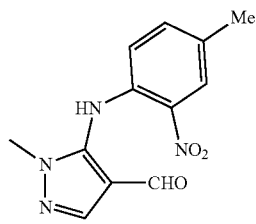 [SMILES: Cc1ccc(Nc2c(C=O)cnn2C)c([N+](=O)[O-])c1]

Pre-SOC-4 was prepared (621 mg 69%) as an orange solid, m.p. 162-163° C., ($R_f$=0.40 in 1:1 v/v ethyl acetate/n-hexane) as per General Procedure 1 with 4-methyl-2-nitroaniline.

Characterisation data for Pre-SOC-4 can be found in Table 2.

1,7-Dimethyl-1,4,5,10-tetrahydrobenzo[b]pyrazolo[3,4-e][1,4]diazapine (FB-SOC-4)

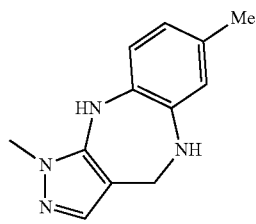 [SMILES: Cc1ccc2c(c1)NCc1cnn(C)c1N2]

FB-SOC-4 was prepared (247 mg, 96%) as pale yellow crystals, m.p. 172-173° C., ($R_f$=0.50 in 1:9 v/v methanol/dichloromethane) as per General Procedure 2.

Characterisation data for FB-SOC-4 can be found in Table 2.

1-Methyl-5-((2-methyl-6-nitrophenyl)amino)-1H-pyrazole-4-carbaldehyde (Pre-SOC-5)

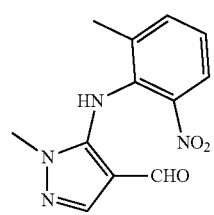 [SMILES: Cc1cccc([N+](=O)[O-])c1Nc1c(C=O)cnn1C]

Pre-SOC-5 was prepared as per General Procedure 1 but heated at 100° C. for 18 hours. This afforded Pre-SOC-5 (396 mg, 44%) as a yellow solid and 1:1.5 mix of atropisomers, m.p. 129-130° C., ($R_f$=0.25 in 1:1 v/v ethyl acetate/n-hexane).

Characterisation data for Pre-SOC-5 can be found in Table 2.

1,9-Dimethyl-1,4,5,10-tetrahydrobenzo[b]pyrazolo[3,4-e][1,4]diazepine (FB-SOC-5)

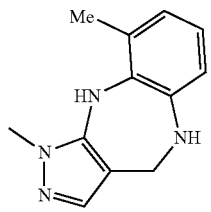

FB-SOC-5 was prepared (211 mg, 82%) as pale yellow crystals, m.p. 137-139° C., ($R_f$=0.50 in 1:9 v/v methanol/dichloromethane) as per General Procedure 2.

Characterisation data for FB-SOC-5 can be found in Table 2.

5-((4-Methoxy-2-nitrophenyl)amino)-1-methyl-1H-pyrazole-4-carbaldehyde (Pre-SOC-6)

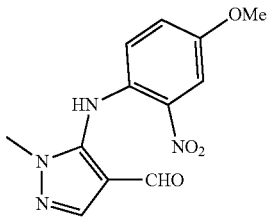 [SMILES: COc1ccc(Nc2c(C=O)cnn2C)c([N+](=O)[O-])c1]

Pre-SOC6 was prepared (401 mg, 42%) as an orange solid, m.p. 132-133° C., ($R_f$=0.27 in 1:1 v/v ethyl acetate/n-hexane) as per General Procedure 1 with 4-methoxy-2-niroaniline.

Characterisation data for Pre-SOC-6 can be found in Table 2.

7-Methoxy-1-methyl-1,4,5,10-tetrahydrobenzo[b]pyrazolo[3,4-e][1,4]diazapine (FB-SOC-6)

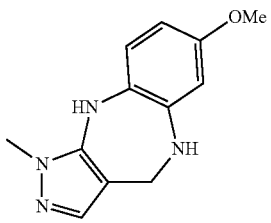 [SMILES: COc1ccc2c(c1)NCc1cnn(C)c1N2]

FB-SOC-6 was prepared (251 mg, 91%) as a pale pink solid, m.p. 126-128° C., ($R_f$=0.55 in 1:9 v/v methanol/dichloromethane) as per General Procedure 2.

Characterisation data for FB-SOC-6 can be found in Table 2.

1-(1-methyl-4,10-dihydrobenzo[b]pyrazolo[3,4-e][1,4]diazepin-5(1H)-yl)ethan-1-one (FB-SOC-7)

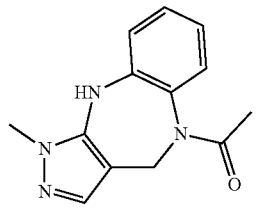 [SMILES: CC(=O)N1Cc2cnn(C)c2Nc2ccccc21]

An ice cold magnetically stirred suspension of FB-SOC-1 (200 mg, 1 mmol) in dry DCM (10 mL) and triethylamine (279 µL, 2 mmol) was treated with acetyl chloride (85 µL, 1.2 mmol) and stirring continued at room temperature for 4 hours. The resultant mixture was diluted with DCM (50 mL) and washed with saturated bicarbonate solution (2×100 mL). The organic phase was separated and washed with brine (50 mL), dried (MgSO$_4$) and concentrated under reduced pressure to give a yellow powder which was purified by column chromatography (silica, eluent: 19:1-9:1 v/v DCM:MeOH gradient elution) and concentration of the relevant fractions ($R_f$=0.40 in 9:1 v/v DCM:MeOH) gave compound FB-SOC-7 as a white powder (197 mg, 0.81 mmol, 81%).

1-Methyl-4,5-dihydro-1H-benzo[b]pyrazolo[4,3-f][1,4]oxazepine (FB-SOC-8)

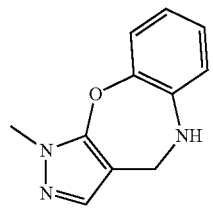

FB-SOC-8 can be synthesized via two multi-step processes (Synthesis 1 and Synthesis 2, respectively).

Synthesis 1

A solution of 1 (500 mg, 3.46 mmol), 2-nitrophenol (1.44 g, 10.38 mmol) and powdered KOH (388 mg, 6.92 mmol) in DMF (4 mL) was irradiated in a CEM Explorer™ microwave reactor at 120° C. for 0.5 hours. The resulting mixture was cooled to room temperature then treated with NH$_4$Cl (50 mL of a saturated aqueous solution) and extracted with ethyl acetate (3×20 mL). The combined organic phases were washed with brine (1×10 mL) before being dried (MgSO$_4$), filtered and concentrated under reduced pressure to afford a yellow oil. Subjection of this residue to flash column chromatography (silica, 1:4→1:1 v/v ethyl acetate/hexane gradient elution) and concentration of the relevant fractions ($R_f$=0.26 in 1:1 v/v ethyl acetate/hexane) afforded 1-methyl-5-(2-nitrophenoxy)-1H-pyrazole-4-carbaldehyde.

Subsequently a suspension of -methyl-5-(2-nitrophenoxy)-1H-pyrazole-4-carbaldehyde (300 mg, 1.21 mmol) and palladium on carbon (20 mg of 10% w/w) in methanol (15 mL) was stirred magnetically at room temperature under an atmosphere of H$_2$ (1 atm) for 18 hours. The resulting mixture was filtered through Celite™ and the solids thus retained were washed with methanol (3×20 mL). The combined filtrates were concentrated under reduced pressure to afford a white solid. Recrystallisation (dichloromethane/hexane) afforded FB-SOC-8 (229 mg, 94%) as white crystals, m.p. 143-145° C., ($R_f$=0.50 in 1:9 v/v methanol/dichloromethane).

Synthesis 2

A magnetically stirred solution of 1 (500 mg, 3.46 mmol) and 2-aminophenol (1.13 g, 10.38 mmol) in DMF (4 mL) was treated with powdered KOH (388 mg, 6.92 mmol) then heated at 120° C. for 2 hours. The resulting mixture was cooled to room temperature then treated with NH$_4$Cl (50 mL of a saturated aqueous solution) and extracted with ethyl acetate (3×20 mL). The combined organic phases were washed with brine (1×10 mL) before being dried (MgSO$_4$), filtered and concentrated under reduced pressure to afford a yellow oil. Subjection of this residue to flash column chromatography (silica, 1:4→1:1 v/v ethyl acetate/hexane gradient elution) and concentration of the relevant fractions ($R_f$=0.21 in 1:1 v/v ethyl acetate/hexane) afforded 1-methyl-1H-benzo[b]pyrazolo[4,3-f][1,4]oxazepine (400 mg, 58%) as a brown oil.

Subsequently, a magnetically stirred solution of 1-methyl-1H-benzo[b]pyrazolo[4,3-f][1,4]oxazepine (350 mg, 1.76 mmol) in methanol (8.5 mL) at 0° C. was treated, in portions over 5 minutes, with NaBH$_4$ (136 mg, 3.51 mmol). The resulting mixture was warmed to room temperature and stirred for 1.5 hours before being treated carefully with H$_2$O (5 mL). Once hydrogen evolution had ceased the methanol was removed under reduced pressure and the resulting aqueous mixture extracted with ethyl acetate (3×10 mL). The combined organic phases where dried (MgSO$_4$), filtered and concentrated under reduced pressure to afford FB-SOC-8 as a white powder.

Characterisation data for FB-SOC-8 can be found in Table 2.

Synthesis of 1-Methyl-4,5-dihydro-1H-benzo[b]pyrazolo[4,3-f][1,4]thiazapine (FB-SOC-9)

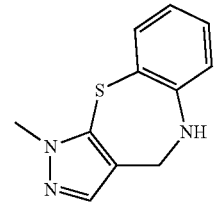

A magnetically stirred solution of 1(150 mg, 1.0 mmol), 2-aminothiophenol (120 µL, 1.1 mmol) and piperidine (11 µL 0.1 mmol) in EtOH (5 mL) was heated at reflux for 3 hours at which point TLC indicated there was no starting aldehyde 1 remaining. The reaction mixture was cooled to 0° C. and treated, in portions, with NaBH$_4$ (98 mg, 2.6 mmol, 2.5 equiv.) and once all was dissolved, the mixture was reheated to reflux for 1 hour then evaporated down to afford a yellow residue. This was dissolved in saturated NaHCO$_3$ solution (20 mL) and extracted with diethyl ether (3×20 mL). The combined organic layers were dried (MgSO$_4$), filtered and concentrated under reduced pressure to afford a yellow solid. Subjection of this residue to flash column chromatography (silica, 3:7→8:2 v/v ethyl acetate/hexane gradient elution v/v ethyl acetate/hexane gradient elution)

and concentration of the relevant fractions ($R_f$=0.15 in 1:1 v/v ethyl acetate/hexane) afforded FB-SOC-9 (54 mg, 24%) as a white solid, m.p. 134-137° C.

Characterisation data for compound FB-SOC-9 is shown in Table 2.

1-Methyl-4,5-dihydro-1H-benzo[b]pyrazolo[4,3-f][1,4]thiazepine 10-oxide (FB-SOC-10)

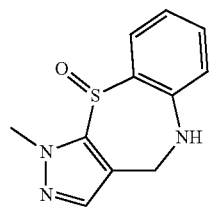 [SMILES: Cn1ncc2c1S(=O)c1ccccc1NC2]

Compound FB-SOC-10 was synthesised in a multi-step reaction. Initially, a magnetically stirred solution of SOC-9 (200 mg, 920 µmol) and triethylamine (96 µL, 2.8 mmol) in THF (3 mL) at 0° C. was treated dropwise with trifluoroacetic anhydride (200 µL, 1.4 mmol). The resulting solution was allowed to stir at 0° C. for 3 hours and then at room temperature for a further 18 hours. The resulting mixture was then concentrated under reduced pressure to afford a yellow oil which was subjected to flash column chromatography (silica, 1:7 v/v ethyl acetate/hexane elution). Concentration of the relevant fractions ($R_f$=0.43 in 1:1 v/v ethyl acetate/hexane) afforded 2,2,2-trifluoro-1-(1-methyl-1H-benzo[b]pyrazolo[4,3-f][1,4]thiazepin-5(4H)-yl)ethanone (261 mg, 94%) as a yellow solid, m.p. 115-118° C.

To produce FB-SOC-10, a solution of 2,2,2-trifluoro-1-(1-methyl-1H-benzo[b]pyrazolo[4,3-f][1,4]thiazepin-5(4H)-yl)ethanone (90 mg, 273 µmol), and $K_2CO_3$ (100 mg, 720 µmol) in MeOH (6 mL) was stirred magnetically at room temperature for 18 hours. The resulting mixture was then concentrated under reduced pressure followed by the addition of water (15 mL), which was then extracted with ethyl acetate (3×15 mL). The combined organic phases were dried ($MgSO_4$), filtered and concentrated under reduced pressure to afford FB-SOC-10 (60 mg, 94%) as a white solid, m.p. 192-194° C., ($R_f$=0.45 in 1:9 v/v methanol/dichloromethane).

Characterisation data for compound FB-SOC-10 is shown in Table 2.

1-Methyl-4,5-dihydro-1H-benzo[b]pyrazolo[4,3-f][1,4]thiazepine 10,10-dioxide (FB-SOC-11)

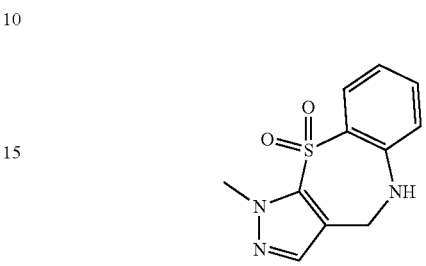

Compound FB-SOC-11 was synthesised in a multi-step reaction. Initially a magnetically stirred solution of 2,2,2-trifluoro-1-(1-methyl-1H-benzo[b]pyrazolo[4,3-f][1,4]thiazepin-5(4H)-yl)ethanone, produced as described in the synthesis of SOC-10 (50 mg, 160 µmol) in glacial acetic acid (0.6 mL) was treated dropwise with hydrogen peroxide (50 µL of a 30% aq. solution, 480 µmol) at room temperature then heated to 80° C. for 4 hours. The resulting solution was cooled to room temperature and treated with water (15 mL) and extracted with ethyl acetate (3×15 mL). The combined organic phases were dried ($MgSO_4$), filtered and concentrated under reduced pressure to afford 2,2,2-trifluoro-1-(1-methyl-10,10-dioxido-1H-benzo[b]pyrazolo[4,3-f][1,4]thiazepin-5(4H)-yl)ethanone (55 mg, 80%) as a yellow solid, m.p. 187-190° C., ($R_f$=0.25 in 1:1 v/v ethyl acetate/hexane).

Next a solution of 2,2,2-trifluoro-1-(1-methyl-10,10-dioxido-1H-benzo[b]pyrazolo[4,3-f][1,4]thiazepin-5(4H)-yl)ethanone (56 mg, 159 µmol), and $K_2CO_3$ (62 mg, 450 µmol) in MeOH (4 mL) was stirred magnetically at room temperature for 18 hours. The resulting mixture was then concentrated under reduced pressure followed by the addition of water (15 mL) which was then extracted with ethyl acetate (3×15 mL). The combined organic phases were dried ($MgSO_4$), filtered and concentrated under reduced pressure to afford FB-SOC-11 (39 mg, 97%) as a white solid, m.p. 172-174° C., ($R_f$=0.39 in 1:9 v/v methanol/dichloromethane).

Characterisation data for compound FB-SOC-11 is shown in Table 2.

TABLE 2

Characterisation data for selected compounds

| Compound (Compound Code) | Structure | Characterisation Data |
|---|---|---|
| 1-Methyl-1H-pyrazol-5-ol (1) | 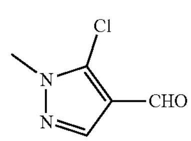 | $^1$H NMR (CDCl$_3$, 300 MHz): J = 9.82 (s, 1H), 7.95 (s, 1H), 3.89 (s, 3H). $^{13}$C NMR (CDCl$_3$, 75 MHz): δ = 182.5 (CH), 140.1 (CH), 132.5 (C), 119.1 (C), 36.2 CH$_3$). IR (ZnSe cell, Film) vmax: 1683, 1529, 1424, 1390, 1196, 814, 770 cm$^{-1}$. LRMS: (ESI +) 145 [(M + H)$^+$, 100%]. |

TABLE 2-continued

Characterisation data for selected compounds

| Compound (Compound Code) | Structure | Characterisation Data |
|---|---|---|
| 1-Methyl-5-((2-nitro-phenyl)amino)-1H-pyrazole-4-carbaldehyde (Pre-SOC-1) | | $^1$H NMR: (CDCl$_3$, 300 MHz): δ = 9.74 (s, 1H), 9.35 (s, 1H), 8.22 (d, J = 8.4 Hz, 1H), 7.97 (s, 1H), 7.46 (t, J = 8.1 Hz, 1H), 6.98 (t, J = 8.1 Hz, 1H), 6.60 (d, J = 8.4 Hz, 1H), 3.72 (s, 3H). $^{13}$C NMR (CDCl$_3$, 75 MHz): δ = 183.2 (CH), 140.9 (CH), 140.3 (C), 140.1 (C), 136.1 (CH), 134.6 (C), 126.6 (CH), 120.2 (CH), 116.2 (C and CH, two overlapping signals), 35.8 (CH$_3$). IR (ZnSe cell, Film) vmax: 3340, 1679, 1613, 1579, 1506, 1338, 1271, 1226, 1149, 742 cm$^{-1}$. LRMS (+ ESI) m/z: 269 [(M + Na)$^+$, 100%]. HRMS (+ ESI) Found: (M + Na)$^+$, 269.0646. C$_{11}$H$_{10}$N$_4$O$_3$ requires (M + Na)$^+$, 269.0651. |
| 1-Methyl-1,4,5,10-tetra-hydrobenzo[b]pyrazolo-[3,4-e][1,4]diazapine (FB-SOC-1) | | $^1$H NMR (d$_6$-DMSO, 300 MHz): δ = 7.99 (s, 1H), 7.05 (d, J = 7.6 Hz, 1H), 6.97 (s, 1H), 6.81 (d, J = 7.6 Hz, 1H), 6.73 (t, J = 7.6 Hz, 1H), 6.64 (t, J = 7.6 Hz, 1H), 5.36 (s, 1H), 3.86 (s, 2H), 3.67 (s, 3H). $^{13}$C NMR (d$_6$-DMSO, 75 MHz): δ = 140.9 (C), 139.5 (C), 135.0 (CH), 133.0 (C), 121.7 (CH), 120.8 (CH), 120.2 (CH), 118.9 (CH), 101.5 (C), 43.4 (CH$_2$), 35.0 (CH$_3$). IR(ZnSe cell, Film) vmax: 3293, 1560, 1505, 1393, 1318, 761 cm$^{-1}$. LRMS (+ ESI) m/z: 201 [(M + H)$^+$, 100%]. |
| 5-((4-Fluoro-2-nitro-phenyl)amino)-1-methyl-1H-pyrazole-4-carbaldehyde (Pre-SOC-2) | | $^1$H NMR (CDCl$_3$, 300 MHz) δ 9.70 (s, 1H), 9.15 (s, 1H), 7.92 (s, 1H), 7.90 (dd, J = 2.9 and 8.6 Hz, 1H), 7.20 (dt, J = 2.9 and 6.9 Hz, 1H), 6.55 (dd, J = 4.5 and 9.3 Hz, 1H), 3.68 (s, 3H). $^{13}$C NMR (CDCl$_3$, 75 MHz) δ 183.2 (CH), 156.9 and 153.6 (CF), 141.4 (CH), 139.8 (C), 137.0 (C), 134.3 (C), 124.3 and 124.0 (CH), 118.0 and 117.9 (CH), 116.1 (C), 112.8 and 112.5 (CH), 35.8 (CH$_3$). IR vmax 2970, 1737, 1581, 1365, 1216 cm$^{-1}$. Mass Spectrum (ESI +) 287 [(M + Na)$^+$, 10%], 265 [(M + H)$^+$, 100%]. HRESIMS Found: (M + Na)$^+$, 287.0550. C$_{11}$H$_9$FN$_4$O$_3$ requires (M + Na)$^+$, 297.0551. |
| 7-Fluoro-1-methyl-1,4,5,10-tetrahydro-benzo[b]pyrazolo-[3,4-e][1,4]diazapine (FB-SOC-2) | | $^1$H NMR (DMSO-d$_6$, 300 MHz) δ 7.99 (s, 1H), 7.03 (dd, J = 6.0 and 8.7 Hz, 1H), 6.98 (s, 1H), 6.66 (dd, J = 2.7 and 10.6 Hz, 1H), 6.55 (dt, J = 2.7 and 8.3 Hz, 1H), 5.60 (s, 1H), 3.87 (d, J = 2.3 Hz, 2H), 3.66 (s, 3H). $^{13}$C NMR (DMSO-d$_6$, 75 MHz) δ 160.5 (C), 157.4 (C), 143.5 and 143.4 (CF), 137.7 (CH), 132.1 (C), 122.5 and 122.4 (CH), 110.3 and 110.0 (CH), 109.5 and 109.2 (CH), 103.7 (C), 45.7 (CH$_2$), 37.6 (CH$_3$). IR vmax 3293, 3280, 1747, 1736, 1715, 1616, 1579, 1541, 1518, 1498, 1457, 1435, 1383, 1311, 1263, 1166, 852, 805 cm$^{-1}$. Mass Spectrum (APCI +) 219 [(M + H)$^+$, 100%]. HRESIMS Found: (M + H)$^+$, 219.1041. C$_{11}$H$_{11}$FN$_4$ requires (M + H)$^+$, 219.1041. |

TABLE 2-continued

Characterisation data for selected compounds

| Compound (Compound Code) | Structure | Characterisation Data |
|---|---|---|
| 5-((4-Chloro-2-nitrophenyl)amino)-1-methyl-1H-pyrazole-4-carbaldehyde (Pre-SOC-3) | | $^1$H NMR (CDCl$_3$, 300 MHz) δ 9.76 (s, 1H), 9.30 (s, 1H), 8.25 (d, J = 2.3 Hz, 1H), 8.00 (s, IH), 7.41 (dd, J = 2.3 and 9.0 Hz, 1H), 6.57 (d, J = 9.0 Hz, 1H), 3.75 (s, 3H). $^{13}$C NMR (CDCl$_3$, 75 MHz) δ 183.2 (CH), 141.5 (CH), 139.3 (C), 139.1 (C), 136.2 (CH), 134.7 (C), 126.1 (CH), 125.3 (C), 117.7 (CH), 116.3 (C) 35.9 (CH$_3$). IR vmax 2969, 1737, 1507, 1365, 1217, 1026, 738 cm$^{-1}$. Mass Spectrum (ESI +) 303 [(M + Na)$^+$, 100%]. HRESIMS Found: (M + Na)$^+$, 303.0256. C$_{11}$H$_9$$^{35}$ClN$_4$O$_3$ requires (M + Na)$_+$, 303.0255. |
| 7-Chloro-1-methyl-1,4,5,10-tetrahydrobenzo[b]pyrazolo-[3,4-e][1,4]diazapine (FB-SOC-3) | | $^1$H NMR (CDCl$_3$, 300 MHz) δ 7.12 (s, 1H), 6.87-6.75 (complex m, 3H), 5.84 (s, 1H), 4.10 (s, 2H), 3.74 (s, 3H), (one NH proton not observed). $^{13}$C NMR (CDCl$_3$, 75 MHz) δ 139.9 (C), 139.6 (C), 135.7 (C), 131.8 (C), 126.2 (C), 122.2 (2 × CH), 119.9 (CH), 101.6 (C), 44.2 (CH2), 34.5 (CH3). IR vmax 3329, 1678, 1627, 1574, 1558, 1522, 1456, 1443, 1409, 1339, 1276, 1228, 1191, 1153, 823, 762 cm$^{-1}$. Mass Spectrum (ESI +) 235 [(M + H)$^+$, 100%]. HRESIMS Found: (M + H)$^+$, 235.0746. C$_{11}$H$_{11}$$^{35}$ClN$_4$ requires (M + H)$^+$, 235.0745. |
| 1-Methyl-5-((4-methyl-2-nitrophenyl)-amino)-1H-pyrazole-4-carbaldehyde (Pre-SOC-4) | | $^1$H NMR (CDCl$_3$, 300 MHz) δ 9.69 (s, 1H), 9.18 (s, 1H), 7.98 (d, J = 1.3 Hz, 1H), 7.91 (s, 1H) 7.22 (dd, J = 1.3 and 8.6 Hz, 1H), 6.47 (d, J = 8.6 Hz, 1H), 3.65 (s, 3H), 2.28 (s, 3H). $^{13}$C NMR (CDCl$_3$, 75 MHz) δ 183.3 (CH), 141.0 (CH), 140.6 (C), 138.0 (C), 137.2 (CH), 134.7 (C), 130.4 (C), 126.2 (CH), 116.4 (CH), 116.0 (C) 35.8 (CH$_3$), 20.2 (CH$_3$). IR vmax 3334, 1738, 1630, 1558, 1503, 1417, 1379, 1297, 1216, 990, 839, 817, 765, 697 cm$^{-1}$. Mass Spectrum (ESI +) 283 [(M + Na)$^+$, 100%], 261 [(M + H)$^+$, 25]. HRESIMS Found: (M + Na)$^+$, 283.0802. C$_{12}$H$_{12}$N$_4$O$_3$ requires (M + Na)$^+$, 283.0802. |
| 1,7-Dimethyl-1,4,5,10-tetrahydrobenzo[b]pyrazolo-[3,4-e][1,4]diazapine (FB-SOC-4) | | $^1$H NMR (CDCl$_3$, 300 MHz) δ 7.10 (s, 1H), 6.71 (m, 2H), 6.63 (s, 1H), 5.79(s, 1H), 4.08 (s, 2H), 3.71 (s, 3H), 2.23 (s, 3H), (one NH proton not observed). $^{13}$C NMR (CDCl$_3$, 75 MHz) δ 140.5 (C), 138.5 (C), 135.8 (CH), 131.6 (C), 130.9 (C), 123.3 (2 × CH), 119.0 (CH), 101.5 (C), 44.6 (CH$_2$), 34.4 (CH$_3$), 20.4 (CH$_3$). IR vmax 2734, 1649, 1525, 1351, 838 cm$^{-1}$. Mass Spectrum (ESI +) 215 [(M + H)$^+$, 100%]. HRESIMS Found: (M + H)+, 215.1291. C$_{12}$H$_{14}$N$_4$ requires (M + Na)$^+$, 215.1291. |
| 1-Methyl-5-((2-methyl-6-nitrophenyl)-amino)-1H-pyrazole-4-carbaldehyde (Pre-SOC-5) | | $^1$H NMR (CDCl$_3$, 300 MHz) δ 9.77 (s, 0.4H), 9.50 (s, 0.6H), 8.62 (s, 1H), 7.83 (d, J = 8.3 Hz, 1H), 7.75 (s, 0.4H), 7.71 (s, 0.6H), 7.38 (d, J = 7.6 Hz, 1H) 7.16 (m, 1H), 3.66 (s, 1.2H), 3.36 (s, 1.8H), 2.85 (s, 1.8H), 1.98 (s, 1.2H). $^{13}$C NMR (CDCl$_3$, 75 MHz) δ 183.2 (CH), 182.9 (CH), 145.0 (C), 144.5 (CH), 142.0 (CH), 140.9 (CH), 136.6 (CH), 135.0 (C), 133.7 (C), 125.1 (CH), 123.4 (CH), 112.0 (C), 43.1 (CH3), 35.9 (CH$_3$), 35.6 (CH$_3$), 18.5 (CH$_3$). IR vmax 3331, 1738, 1567, 1483, 1457, 1432, 1299, 787 cm$^{-1}$. |

TABLE 2-continued

Characterisation data for selected compounds

| Compound (Compound Code) | Structure | Characterisation Data |
| --- | --- | --- |
| | | Mass Spectrum (ESI +) 283 [(M + Na)$^+$, 100%], 261 [(M + Na)$^+$, 75]. HRESIMS Found: (M + Na)$^+$, 283.0803. $C_{12}H_{12}N_4O_3$ requires (M + Na)$^+$, 283.0802. |
| 1,9-dimethyl-1,4,5,10-tetrahydro-benzo[b]pyrazolo-[3,4-e][1,4]diazapine (FB-SOC-5) | 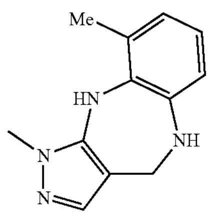 [SMILES: Cc1cccc2c1Nc1c(cnn1C)CN2] | $^1$H NMR (DMSO-d$_6$, 300 MHz) δ 6.99 (s, 1H), 6.81-6.65 (Complex m, 4H), 5.26 (s, 1H), 3.87 (s, 2H), 3.69 (s, 3H), 2.31 (s, 3H). $^{13}$C NMR (DMSO-d6, 75 MHz) 141.7 (C), 140.8 (C), 134.7 (CH), 132.1 (C), 127.7 (C), 123.2 (CH), 121.3 (CH), 120.2 (CH), 101.5 (C), 43.8 (CH$_2$), 34.5 (CH$_3$), 18.3 (CH$_3$). IR vmax 3271, 1705, 1568, 1491, 1433, 1384, 1307, 990, 808 cm$^{-1}$. Mass Spectrum (ESI +) 451 [(2M + Na)$^+$, 100%]. HRESIMS Found: (M + Na)$^+$, 237.1111. $C_{12}H_{14}N_4$ requires (M + Na)$^+$, 237.1111. |
| 5-((4-Methoxy-2-nitrophenyl)amino)-1-methyl-1H-pyrazole-4-carbaldehyde (Pre-SOC-6) | 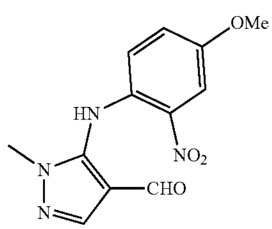 [SMILES: COc1ccc(Nc2c(C=O)cnn2C)c([N+](=O)[O-])c1] | $^1$H NMR (CDCl$_3$, 300 MHz) δ 9.72 (s, 1H), 9.13 (s, 1H), 7.93 (s, 1H), 7.66 (d, J = 2.5 Hz, 1H), 7.10 (dd, J = 2.5 and 9.2 Hz, 1H), 6.59 (d, J = 9.2 Hz, 1H), 3.82 (s, 3H), 3.68 (s, 3H). $^{13}$C NMR (CDCl$_3$, 75 MHz) δ 183.3 (CH), 153.1 (C), 141.0 (CH), 140.9 (C), 135.1 (C), 134.2 (C), 125.1 (CH), 118.1 (CH), 115.6 (C), 108.2 (CH), 55.9 (CH$_3$), 35.9 (CH$_3$). IR vmax 3401, 1737, 1678, 1519, 1365, 1287, 1230, 1034, 761 cm$^{-1}$. Mass Spectrum (ESI +) 299 [(M + Na)$^+$, 100%], 277 [(M +H)$^+$, 40]. HRESIMS Found: (M + Na)$^+$, 299.0752. $C_{12}H_{12}N_4O_4$ requires (M + Na)$^+$, 299.0751. |
| 7-Methoxy-1-methyl-1,4,5,10-tetrahydro-benzo[b]pyrazolo-[3,4-e][1,4]diazapine (FB-SOC-6) | 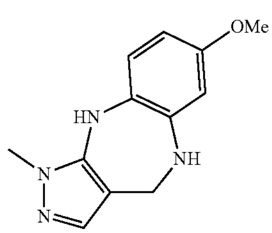 [SMILES: COc1ccc2c(c1)NCc1cnn(C)c1N2] | $^1$H NMR (CDCl$_3$, 300 MHz) δ 7.10 (s, 1H), 6.77 (d, J = 8.6 Hz, 1H), 6.48 (dd, J = 2.4 and 8.6 Hz, 1H), 6.41 (d, J = 2.4 Hz, 1H), 5.63 (s, 1H) 4.10 (s, 2H), 3.76 (s, 3H), 3.72 (s, 3H), (one NH proton not observed). $^{13}$C NMR (CDCl$_3$, 75 MHz) δ 155.0 (C), 140.6 (C), 140.1 (C), 135.8 (CH), 127.3 (C), 120.0 (CH), 108.3 (CH), 107.9 (CH), 101.2 (C), 55.5 (CH3), 44.6 (CH$_2$), 34.4 (CH$_3$). IR vmax 1748, 1716, 1575, 1558, 1541, 1518, 1507, 1489, 1456, 1205 cm$^{-1}$. Mass Spectrum (ESI +) 231 [(M + H)$^+$, 100%]. HRESIMS Found: (M + Na)$^+$, 253.1060. $C_{12}H_{14}N_4O$ requires (M + Na)$^+$, 253.1060. |
| 1-(1-Methyl-4,10-dihydrobenzo[b]-pyrazolo[3,4-e][1,4]-diazepin-5(1H)-yl)-ethan-1-one: (FB-SOC-7) | 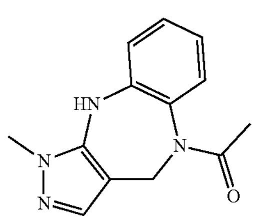 [SMILES: CC(=O)N1Cc2cnn(C)c2Nc2ccccc21] | $^1$H NMR (500 MHz, DMSO-d$_6$) δ 8.41 (s, 1H), 7.34 (dd, J = 8.1, 1.5 Hz, 1H), 7.28 (td, J = 7.4, 1.5 Hz, 1H), 7.23 (dd, J = 7.8, 1.5 Hz, 1H), 7.08 (s, 1H) 6.97 (td, J = 7.4, 1.5 Hz, 1H), 5.38 (d, J = 14.5 Hz, 1H), 3.72 (d, J = 14.5 Hz, 1H), 3.70 (s, 3H), 1.69 (s, 3 H). $^{13}$C NMR (126 MHz, DMSO-d$_6$) δ 168.41, 139.30, 139.14, 135.60, 131.69, 130.05, 128.68, 121.36, 119.98, 100.71, 42.51, 35.26, 21.93. IR (Diamond cell, film) $v_{max}$: 3291, 1639, 1560, 1504, 1395, 1294, 1254, 1086, 747 cm$^{-1}$. LRMS (+ ESI) m/z: 243 ([M + H]$^+$, 100%). HRESIMS (+ ESI) Found: (M + H)$^+$, 243.1244. $C_{13}H_{14}N_4O$ requires (M + H)$^+$, 243.1246. |

TABLE 2-continued

Characterisation data for selected compounds

| Compound (Compound Code) | Structure | Characterisation Data |
|---|---|---|
| 1-Methyl-4,5-dihydro-1H-benzo[b]pyrazolo[4,3-f][1,4]oxazepine (FB-SOC-8) | | $^1$H NMR (d$_6$-DMSO, 300 MHz): δ = 7.99 (s, 1H), 7.05 (d, J = 7.6 Hz, 1H), 6.97 (s, 1H), 6.81 (d, J = 7.6 Hz, 1H), 6.73 (t, J = 7.6 Hz, 1H), 6.64 (t, J = 7.6 Hz, 1H), 5.36 (s, 1H), 3.86 (s, 2H), 3.67 (s, 3H). $^{13}$C NMR (d$_6$-DMSO, 75 MHz): δ =140.9 (C), 139.5 (C), 135.0 (CH), 133.0 (C), 121.7 (CH), 120.8 (CH), 120.2 (CH), 118.9 (CH), 101.5 (C), 43.4 (CH$_2$), 35.0 (CH$_3$). IR (ZnSe cell, Film) vmax: 3293, 1560, 1505, 1393, 1318, 761 cm$^{-1}$. LRMS (+ ESI) m/z: 201 [(M + H)+, 100%]. |
| 1-Methyl-4,5-dihydro-1H-benzo[b]pyrazolo[4,3-f][1,4]thiazapine (FB-SOC-9) | | $^1$H NMR (300 MHz, CD$_3$OD): δ = 7.37 (d, J = 7.8 Hz, 1H), 7.29 (s, 1H), 7.20 (dd, J = 7.8 and 7.8 Hz, 1H), 6.99 (d, J = 7.8 Hz, 1H), 6.89 (dd, J = 7.8 and 7.8 Hz, 1H), 4.25 (s, 2H), 3.83 (s, 3H). $^{13}$C NMR (75 MHz, CD$_3$OD): δ = 152.1 (C), 137.5 (CH), 132.8 (C), 132.5 (CH), 130.9 (CH), 124.0 (CH), 123.9 (C), 123.3 (CH), 120.6 (C), 44.7 (CH$_2$), 36.5 (CH$_3$).IR (ZnSe cell, film) vmax: 3358, 2937, 1479, 1417, 1312 cm$^{-1}$. LRMS (+ ESI) m/z: 218 ([M + H]$^+$, 100%). HRMS (+ ESI) Found: (M + Na)$^+$, 240.0566. C$_{11}$H$_{11}$N$_3$S requires (M + Na)$^+$, 240.0566. |
| 1-Methyl-4,5-dihydro-1H-benzo[b]pyrazolo[4,3-f][1,4]thiazepine 10-oxide (FB-SOC-10) | | $^1$H NMR (200 MHz, CD$_3$OD): δ = 7.62 (d, J = 8.2 Hz, 1H), 7.47 (s 1H), 7.32 (t, J = 7.6 Hz, 1H), 7.80 (m, 2H), 4.77 (d, J = 15.6 Hz, 1H), 4.29 (d, J = 15.6 Hz, 1H), 4.03 (s, 3H), (the NH proton was not observed). $^{13}$C NMR (75 MHz, CD$_3$OD): δ = 148.3 (C), 140.0 (C), 137.3 (CH), 135.3 (CH), 134.0 (CH), 123.0 (C), 121.5 (CH), 120.2 (C), 117.9 (CH), 38.0 (CH$_3$), 37.6 (CH$_2$). IR (ZnSe cell, film) vmax: 3302, 3096, 2928, 1547, 1468, 1029 cm$^{-1}$. LRMS (+ ESI) m/z: 234 ([M + H]$^+$, 100%). HRMS (+ ESI) Found: (M + Na)$^+$, 256.0515. C$_{11}$H$_{11}$N$_3$OS requires (M + Na)$^+$, 256.0515. |
| 1-Methyl-4,5-dihydro-1H-benzo[b]pyrazolo[4-3-f][1,4]thiazepine 10,10-dioxide (SOC-11) (FB-SOC-11) | | $^1$H NMR (200 MHz, d$_4$-MeOD): δ = 7.80 (d, J = 8.4 Hz, 1H), 7.45 (s 1H), 7.29 (t, J = 7.0 Hz, 1H), 7.69 (m, 2H), 4.57 (s, 2H), 4.11 (s, 3H), (the NH proton was not observed). $^{13}$C NMR (75 MHz, d$_4$-MeOD): δ = 146.0 (C), 140.0 (C), 137.0 (CH), 135.6 (CH), 126.8 (CH), 122.6 (C), 120.9 (CH), 117.1 (C), 116.7 (CH), 38.8 (CH$_2$), 38.5 (CH$_3$). IR (ZnSe cell, film) vmax: 3398, 3078, 2958, 1602, 1447, 1312, 1164 cm$^{-1}$. LRMS (+ ESI) m/z: 250 ([M + H]$^+$, 100%). HRMS (+ ESI) Found: (M + Na)$^+$, 272.0464. C$_{11}$H$_{11}$N$_3$O$_2$S requires (M + Na)$^+$, 272.0454. |

Example 2—Salts

The production of salts is known to those skilled in the art. For example, for the production of a hydrochloride salt, HCl (4M in dioxane, 1.1 equivalents) can be added to a magnetically stirred solution of a free base, for example (FB-SOC-1 or FB-SOC-2) in THF. Stirring was continued for 30 minutes. The resulting precipitate was collected via filtration to give the corresponding salt derivatives as hydrochloride salts.

One example salt of Formula (I) is the hydrochloride salt of:

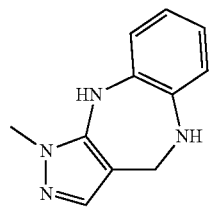

The hydrochloride salt:

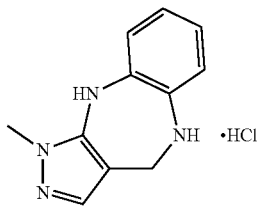

is utilised in the following examples and has been given the code SOC-1.

Example 3—In Vivo Studies (Behavioural Effects—Social Interaction Tests with Hooded Wistar Rats)

A social interaction test was conducted using Hooded Wistar rats and SOC-1 was shown to elicit a powerful pro-social effect in the rodents. The primary phenotypic effect was a massive increase in a behaviour called "adjacent lying" where unfamiliar rats come together in passive social contact for prolonged periods. As can be seen in FIG. 1, image (A), SOC-1 given as an intraperitoneal injection (IP) to male Hooded Wistar rats caused a massive increase in adjacent lying in the social interaction test at doses of 5 and 10 mg/kg IP. (n=6-8 pairs per condition, 20 minute test). Remarkably the effects of SOC-1 outlive its acute administration and a prolonged upregulation of social behaviour (measured as time spent in close proximity) in rats given only 3 doses of SOC-1, 2 weeks previously, was observed (FIG. 1, image (B)). Two weeks following SOC-1 treatment (3 doses in total across 6 days) male Hooded Wistar rats show increased proximity towards a novel conspecific relative to controls (time spent within 1 body length)). Similar long-term upregulation of social behaviour was found with oxytocin (OT) (M. Bowen, et al., "Adolescent Oxytocin Exposure Causes Persistent Reductions in Anxiety and Alcohol Consumption and Enhances Sociability in Rats", PloS One, 6(11), 2011-e27237; and A. Suraev, et al., "Adolescent exposure to oxytocin, but not the selective oxytocin receptor agonist TGOT, increases social behavior and plasma oxytocin in adulthood", Hormones and Behavior, 65(5), 488-496, 2014. Direct comparisons of the most efficacious dose of SOC-1 to the most efficacious doses of the other substances known to elicit adjacent lying behaviour in rats (arginine vasopressin (AVP), 3,4-methylenedioxy-methamphetamine (MDMA) and WAY 267,464), showed that SOC-1 had the most powerful pro-social effects by a considerable margin (FIG. 1, image (C)).

Figure 2:
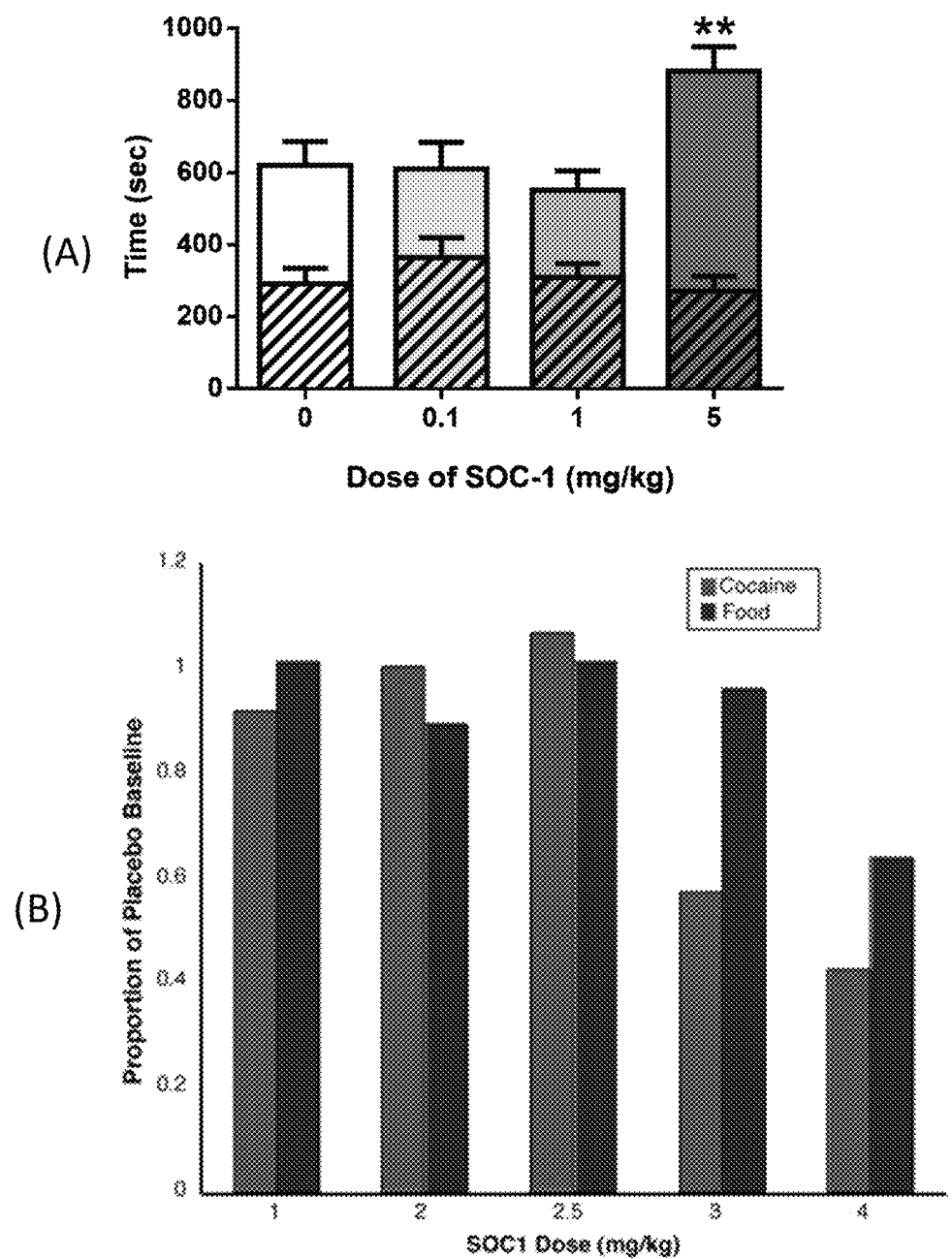
FIG. 2—Image (A) shows the results of a social preference test, whereby SOC-1 (5 mg/kg IP) enhanced rats natural preference for an unfamiliar live rat (solid portion of bars) over a toy rat (patterned portion of bars); and image (B) shows the selective effects of orally administered SOC-1 (3 mg/kg) on intravenous cocaine self-administration in *rhesus* monkeys.

Social preference was shown to increase in male Albino Wistar rats due to the administration of SOC-1 in rats given a choice between spending time with a caged conspecific or a toy rat (FIG. 2, image (A)). As can be seen in FIG. 2, image (A), SOC-1, at a dose of 5 mg/kg, significantly elevated preference for the live rat.

Example 4—In Vivo Studies (Behavioural Effects—Non-Human Addiction with Rhesus Monkeys)

Figure 3:
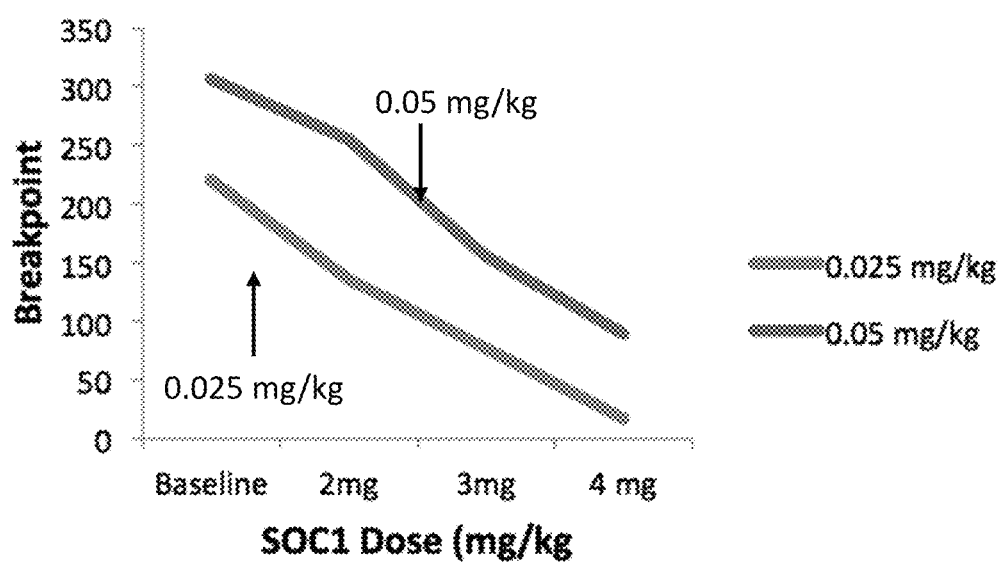
FIG. 3—The progressive ratios for cocaine self-administration for *Rhesus* monkeys administered SOC-1.

Additional behavioural studies using SOC-1 in non-human primate models of addiction and social behaviour have shown that SOC-1 given orally to rhesus monkeys at a dose of 3 mg/kg nearly halved intravenous cocaine self-administration relative to baseline levels without affecting food consumption (FIG. 2, image (B)). In this study the administration of SOC-1 drastically reduced cocaine consumption without affecting food consumption. The progressive ratio for cocaine self-administration is shown in FIG. 3.

Example 5—In Vivo Studies (Pharmacokinetics)

Figure 4:
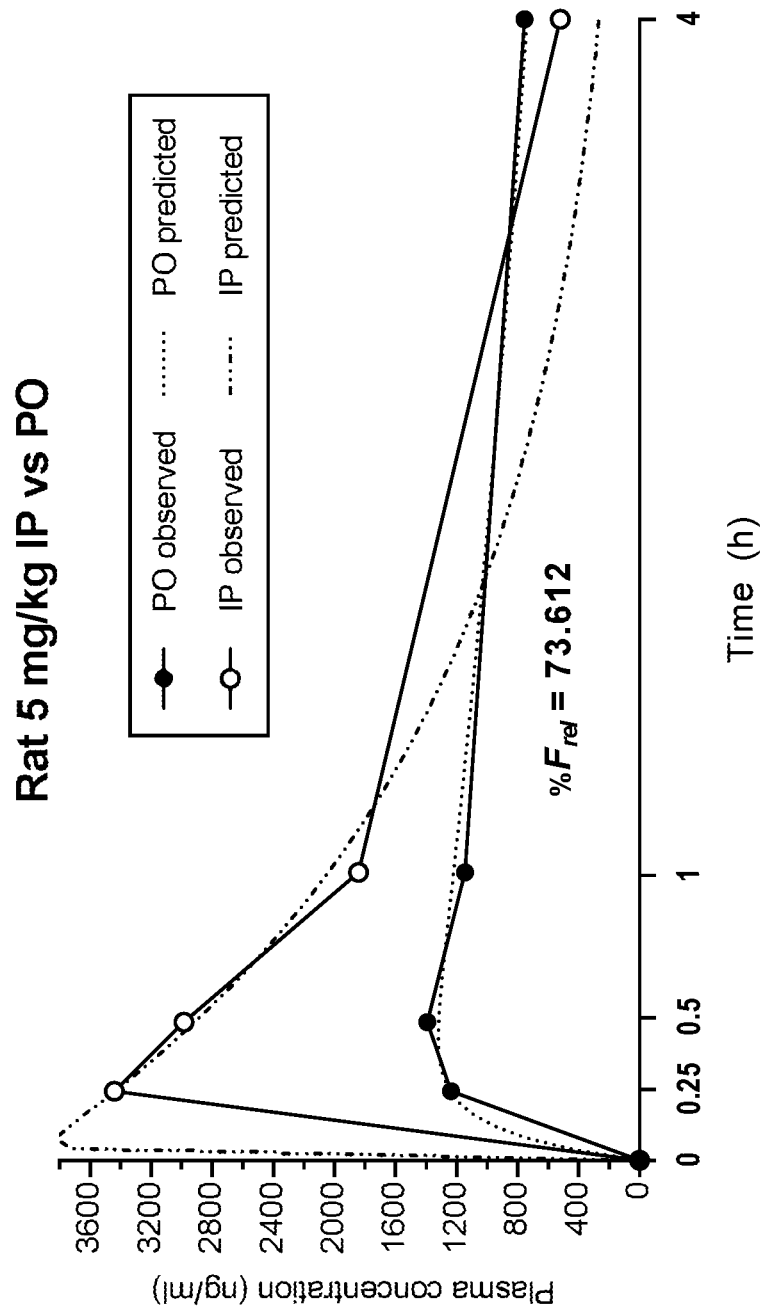
FIG. 4—Concentration-time profiles between the same 5 mg/kg dose of SOC-1 given via intraperitoneal injections (IP) or orally (PO).

In in vivo rodent models using Hooded Wistar rats, SOC-1 demonstrates excellent oral bioavailability and pharmacokinetic parameters relative to the behaviourally effective intraperitoneal route of administration (Table 3 and FIG. 4). When given via an intraperitoneal injection (IP), SOC-1 plasma levels show a rapid elevation. This swiftly declines over the first hour before settling into a less hasty decrease in concentration over the proceeding hours. Conversely, the same dose of SOC-1 given orally demonstrates far greater stability in plasma concentration over many hours. The initial increase in plasma levels is less pronounced when SOC-1 is given orally but the decline is far less rapid, with plasma concentration becoming equivalent to IP between 1 and 4 hours. In many ways this is a more favourable profile as, unlike the IP dosing, oral dosing results in levels of SOC-1 that are still high but that are also very stable over many hours, with a half-life of over four hours.

TABLE 3

Pharmacokinetic data for intraperitoneal injection (IP) and oral (PO) administration of SOC-1

| Route of Administration | Dose (mg/kg) | R2 | $k_a$ (h$^{-1}$) | $k_e$ (h$^{-1}$) | $t_{1/2ka}$ (h) | $t_{1/2ke}$ (h) | $T_{max}$ (h) | $C_{max}$ (ng/ml) | $AUC_{0-inf}$ (ng/ml*h) | $AUC_{0-t}$ (ng/ml*h) |
|---|---|---|---|---|---|---|---|---|---|---|
| IP | 5 | 0.995 | 71.727 | 0.679 | 9.663 × 10$^{-3}$ | 1.021 | 0.066 | 3837.864 | 5910.67 | 5515.82 |
| PO | 5 | 0.998 | 9.45 | 0.0167 | 0.073 | 4.147 | 0.435 | 1319.358 | 8488.6 | 4060.31 |

Figure 5:
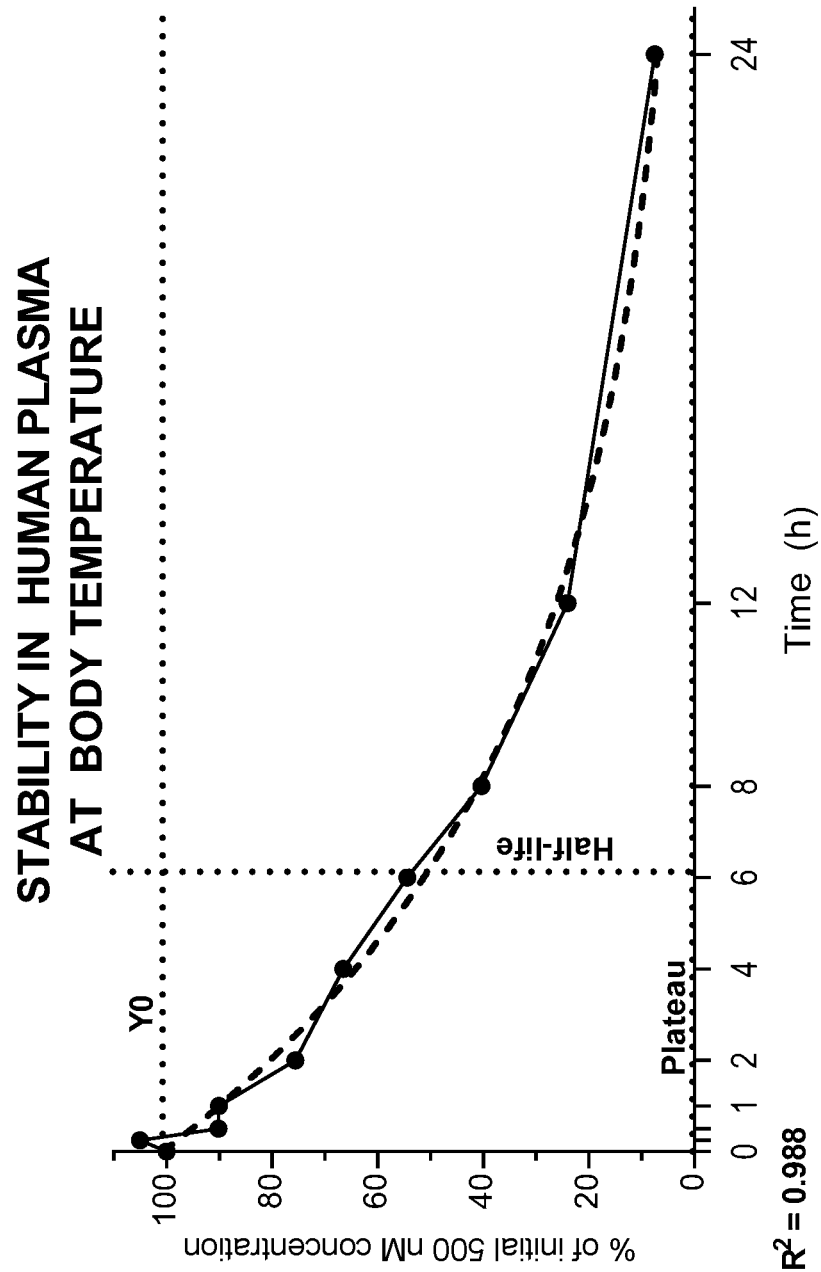
FIG. 5—Stability of SOC-1 incubated at body temperature in human plasma.

SOC-1 demonstrates excellent stability in human plasma in in vitro plasma stability assays (FIG. 5). Even at relatively low concentrations (500 nM) SOC-1 demonstrates a half-life of over 6 hours when incubated in human plasma at body temperature.

Example 6—In Vivo Studies (Pharmacodynamics)

Figure 6:
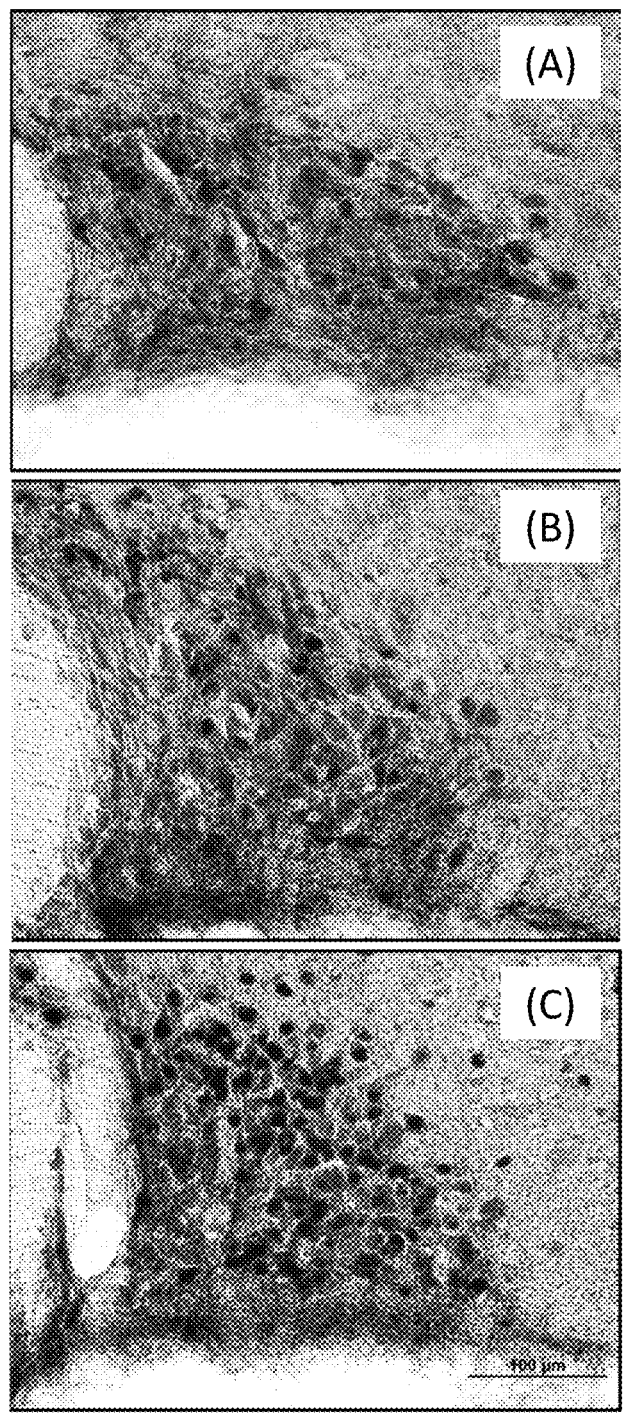
FIG. 6—The results of a Fos immunohistochemistry study examining activation of the oxytocin-containing cells in the supraoptic nucleus of the hypothalamus (SON) of male Wistar rats, with: a vehicle (image (A)); oxytocin at a concentration of 1 mg/kg (image (B)); and SOC-1 at a concentration of 5 mg/kg (image (C)).

Fos immunohistochemistry was used to identify the neural "signature" of SOC-1 (5 mg/kg) in rat brain relative to injections of peripheral oxytocin (OT) (1 mg/kg). Results are shown in Table 4. SOC-1 produces a similar overall pattern of neural activation and behavioural effects as OT. However, the effects are much larger and additional areas are activated by SOC-1 that are implicated in the regulation of social behaviour (e.g. lateral septum, medial preoptic area and supraoptic nucleus). SOC-1 produces powerful activation of OT-containing neurons in both the supraoptic (FIG. 6: (A)=vehicle; (B)=oxytocin; and (C)=SOC-1) and paraventricular nucleus of the hypothalamus. SOC-1 (5 mg/kg) given to male Wistar rats strongly activates Fos expression in the oxytocin-positive cells in the supraoptic nucleus of the hypothalamus (SON). SOC-1 is substantially more effective at activating these oxytocin-containing cells in the SON than 1 mg/kg of oxytocin (intraperitoneal injection).

TABLE 4

Mean number (±standard error of the mean (SEM)) of Fos-positive cells in brain regions of interest

| Region | Vehicle (VEH) | Oxytocin (OT) | SOC-1 |
|---|---|---|---|
| Sites where SOC-1 caused greater activation than VEH and OT | | | |
| Lateral septum (ventral) | 10 (1.97) | 9.17 (2.55) | 34.17 (5.26)[a), b)] |
| Medial preoptic area | 3.38 (0.80) | 3.8 (1.85) | 10.30 (1.69)[a), b)] |
| Supraoptic nucleus | 2.75 (1.45) | 4.57 (1.82) | 15.42 (1.95)[a), b)] |
| Sites where SOC-1 caused greater activation than VEH but not OT | | | |
| BNST (middle anterior part)) | 2.88 (.69) | 5.83 (0.95) | 7 (1.18)[a)] |
| BNST (dorsolateral division) | 4.38 (.73) | 11.33 (2.36) | 10.25 (1.38)[a)] |
| Median preoptic nucleus | 4.13 (.67) | 7.17 (1.38) | 7.08 (0.96)[a)] |
| Paraventircular nucleus | 5.88 (1.29) | 55.57 (9.89) | 47.18 (6.51)[a)] |
| Central nucleus of the amygdala | 2.88 (0.89) | 25.14 (3.76) | 14.33 (2.31)[a)] |
| PAG (ventrolateral) | 2.75 (1.52) | 6.57 (1.36) | 8.58 (1.95)[a)] |
| Lateral Parabrachial nucleus | 0.75 (0.62) | 19.14 (1.22) | 12.91 (1.68)[a)] |
| Locus Ceruleus | 0 (0) | 4.14 (0.31) | 8.08 (1.84)[a)] |
| Nucleus of Solitary Tract | 1.50 (0.57) | 31.68 (4.65) | 17.58 (2.49)[a)] |
| Mean percent (±SEM) of OT cells in hypothalamic regions that were Fos positive | | | |
| Supraoptic nucleus | 7.83 (3.34) | 13.5 (6.64) | 32.59 (4.24)[a), b)] |
| Paraventircular nucleus | 1.54 (0.70) | 22.07 (4.94) | 23.41 (2.95)[a)] |

[a)]SOC-1 significantly > VEH;
[b)]SOC-1 significantly > OT

Remarkably, however, SOC-1 does not show affinity for the orthosteric binding sites on the oxytocin receptor (OTR) (human OT receptor, IC50 (nM) against [3H]OT=>10000). Furthermore, examination of IP1 signalling on OTR HEK cells has revealed that SOC-1 is not an agonist or antagonist at OTRs, nor a positive allosteric modulator of the OTR. Nor does SOC-1 show any affinity for the orthosteric binding sites of AVP receptors (V1A, V1B or V2) (e.g. human V1a receptor, IC50 (nM) against [3H]AVP=>10000). IP1 signalling on V1aR HEK cells revealed that SOC-1 is not an agonist or positive allosteric modulator of V1aRs, but showed weak antagonist activity at these receptors.

Comprehensive screening of affinity for the orthosteric binding sites for numerous receptors from the Psychoactive Drug Screening Program (PDSP) have failed as yet to identify a target, despite the powerful OT-like behavioural effects of the compound evident in vivo and the clear activation of brain OT systems evident from our Fos data. In the PDSP, SOC-1 had no notable affinity for 5-HT1A, 5-HT1B, 5-HT1D, 5-ht1e, 5-HT2A, 5-HT2B, 5-HT2C, 5-HT3, 5-ht5a, 5-HT6, 5-HT7, Alpha1B, Alpha1D, Alpha2A, Alpha2B, Alpha2C, Beta1, Beta2, Beta3, BZP Rat Brain Site, D1, D2, D3, D4, D5, DAT, DOR, GABAA, H1, H2, H3, KOR, M1, M2, M3, M4, M5, MOR, NET, PBR, SERT, Sigma 1 and Sigma 2 receptors.

Examination of signalling using rat hypothalamic neurons showed that SOC-1 did not alter IP1 levels and did not reliably alter $Ca^{2+}$ levels. However, SOC-1 was able to decrease basal cAMP, but did not reliably decrease forskolin-stimulated cAMP. All of this suggests that it may either be working on a Gs-coupled receptor as an inverse agonist, or as a Gi-coupled receptor agonist.

Example 7—Examination of Toxicity and Adverse Effects

No apparent cytotoxicity of SOC-1 has been seen in vitro or toxicity in vivo. In a test, SH-SY5Y neuroblastoma cells and HEK-293 cells ($4 \times 10^4$ cells per well) were exposed to OT or SOC-1 (0.01-10 µM) for 48 hours, with daily media changes. Viability of cells was assessed after a 4 hour exposure to Cell Titer Blue (Promega). No significant differences in viability were induced by OT or SOC-1 at any assayed concentration (Table 5). As SH-SY5Y cells express the OTR (P. Cassoni, et al., Int J Cancer, 77, 695-700, 1998) and HEK-293 cells express little endogenous OTR (BMC Genomics 12:4), these results suggest SOC-1 does not induce receptor or non-receptor-mediated cytotoxic events, even at excess concentrations.

TABLE 5

Viability of cells exposed to oxytocin or SOC-1 for 48 hours. Viability is expressed as mean percentage of vehicle viability ± standard deviation (SD). No significant differences in viability were induced by oxytocin or SOC-1 at any assayed concentration.

| Concentration (µM) | SH-SY5Y | | HEK-293 | |
|---|---|---|---|---|
| | Oxytocin | SOC-1 | Oxytocin | SOC-1 |
| 0.01 | 100.4 ± 2.4 | 98.9 ± 2.7 | 97.8 ± 6.6 | 102.6 ± 2.1 |
| 0.1 | 101.3 ± 1.0 | 99.1 ± 2.9 | 100.0 ± 3.2 | 102.1 ± 3.2 |
| 1 | 100.2 ± 1.1 | 97.7 ± 1.6 | 101.5 ± 3.7 | 102.5 ± 3.6 |
| 10 | 100.6 ± 2.9 | 97.0 ± 2.5 | 104.3 ± 2.6 | 103.2 ± 1.2 |

Figure 7:
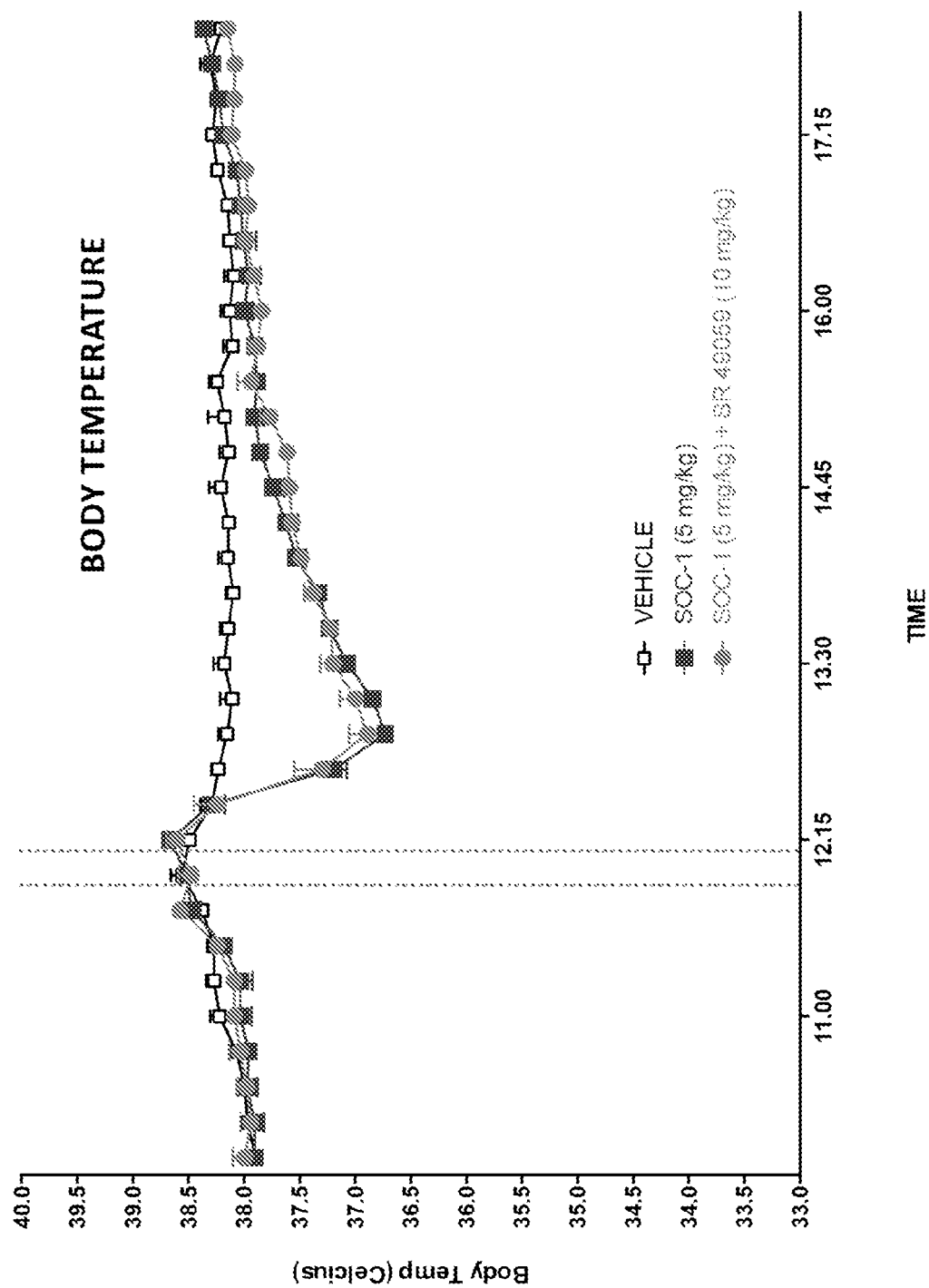
FIG. 7—The monitored body temperatures of Wistar rats administered vehicle, SOC-1 (5 mg/kg), or SOC-1 and the V1A receptor antagonist SR49059 (10 mg/kg).
Figure 8:
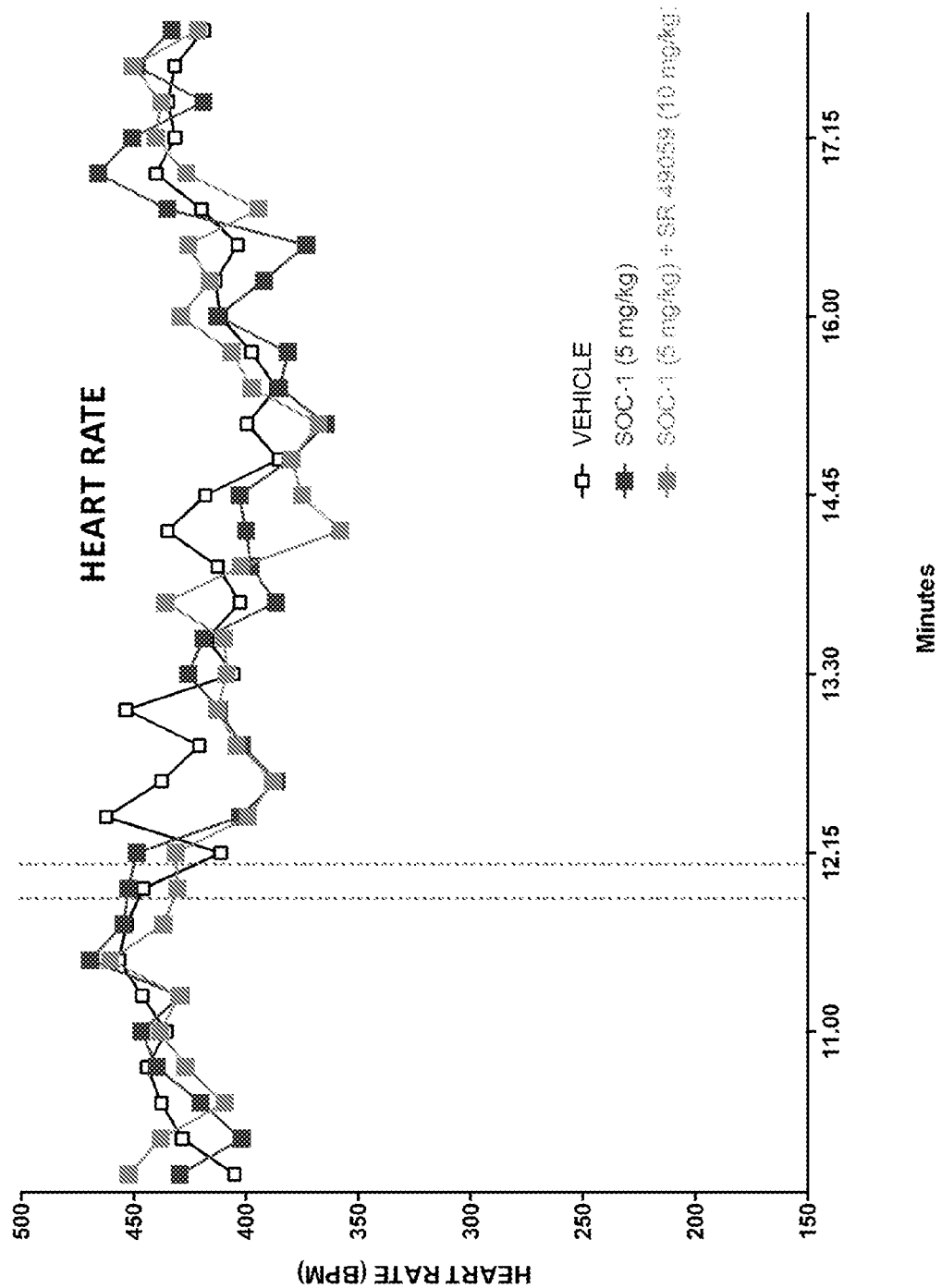
FIG. 8—The monitored heart rates for Wistar rats administered vehicle, SOC-1 (5 mg/kg), or SOC-1 and the V1A receptor antagonist SR49059 (10 mg/kg).

With regard to in vivo toxicity/adverse events: at higher doses in rats (10-20 mg/kg IP), some mild inhibition of locomotor activity was present. However, the rats were not ataxic or comatose, they were simply in a relaxed quiescent state. The rats tolerated repeated dosing with SOC-1 without any apparent adverse effects such as a loss of body weight or a change in coat condition. SOC-1 is without effect in conventional non-social tests of anxiety (e.g. elevated plus maze, open field) either during acute dosing or as a residual long-term effect. SOC-1 does not produce a conditioned place preference in rats suggesting low abuse potential. Biotelemetry experiments show a modest hypothermia in rats at 5 mg/kg, but no effect of SOC-1 on heart rate (FIG. 7 and FIG. 8). Effects on body temperature and other behaviours are not blocked by pre-treatment with the vasopressin V1A receptor antagonist SR49059 (10 mg/kg). The modest hypothermia produced by SOC-1 is abolished at higher ambient temperatures (i.e. 30° C.) but the social effects of the drug remain at these temperatures. The data in these two studies was gathered with DataSciences International biotelemetry system.

Example 8—Drug Relapse Study with Sprague-Dawley Rats

Animals 32 male Sprague Dawley rats (weighing 200-250 g) were obtained from the Animal Resources Centre (Perth, WA, Australia). Rats were housed in pairs (cage size: 40×27×16 cm until week 6 when they were relocated to larger cages: 64×20×40 cm) with the exception of a two-day postoperative period of individual housing. Food and water were available ad libitum in the home cages and not during experimental procedures. Lighting was kept on a 12-hour light/dark cycle (lights on 06:00), with all experiments conducted during the light cycle. Housing room temperature was maintained at 21° C. (±1° C.). Prior to the start of experimentation, rats were acclimatised to the facility for seven days and were handled daily for a further seven days. All experimental procedures were conducted in accordance with the *Australian Code of Practice for the Care and Use of Animals for Scientific Purposes* (8th edition, 2013) and were approved by the Macquarie University Animal Ethics Committee.

Drugs

Methamphetamine hydrochloride (METH) was purchased from the Australian Government Analytical Laboratories (Pymble, NSW, Australia). SOC-1 was synthesized by Prof Michael Kassiou (School of Chemistry, University of Sydney, Australia). METH and SOC-1 were dissolved in saline (0.9%) for injection purposes. The V1a receptor antagonist SR49059 was purchased from Axon Medchem BV (Groningen, The Netherlands) and the oxytocin receptor antagonist C25 (5-(3-(3-(2-chloro-4-fluorophenoxy)azetidin-1-yl)-5-(methoxymethyl)-4H-1,2,4-triazol-4-yl)-2-methoxypyridine) was synthesized according to the procedures of Hudsen et al (2005) and Brown et al (2010). SR49059 and C25 were dissolved in a 15% dimethyl sulfoxide (DMSO), 2% tween 80, and 83% saline vehicle. All solutions were freshly prepared for each test session.

Apparatus

Testing was conducted in 16 standard operant response chambers (32×25×34 cm; Med Associates, St Albans, VT, USA), which were housed in sound attenuating boxes (41× 56×56 cm) equipped with a fan for masking noise and to provide ventilation. Each chamber was equipped with two retractable levers (1 active, 1 inactive), cue lights positioned above each lever, and a house light. The chambers also contained a metal arm with an adjustable weight and a spring connector, which were attached to a swivel. Polyethylene tubing threaded through the spring connector was connected to a 10 ml syringe attached to an infusion pump (Med Associates) located outside of the sound-attenuating chamber. The tubing exiting from the base of the spring connector was connected to the back mount of the intravenous catheter.

Four infrared photobeam detectors were also positioned on the sidewall of each operant chamber to measure locomotor activity. Active and inactive lever presses, number of infusions and locomotor activity was collected and recorded using MED-PC software.

Surgery

Rats were implanted with a chronic indwelling catheter in the right jugular vein. To achieve this, rats were anaesthetised with isoflurane gas (3% in oxygen 2 l/min) and aseptic surgical techniques were used. Catheter implantation, as well as catheter construction is as previously described (Moteby et al., 2013). Rats were treated with 0.2 ml of the antibiotic cephazolin sodium (100 mg/ml) intravenously and the analgesic carpofen (5 mg/kg) subcutaneously at the time of surgery and daily for the following two days. Following this, catheter patency was maintained by a daily intravenous flush of 0.2 ml of cephazolin sodium in heparinised saline (300 IU/ml). Rats were allowed 7 days to recover from surgery before experimentation began.

Methamphetamine Intravenous Self-Administration (IVSA) Procedure

Following recovery from surgery, rats were able to self-administer intravenous METH during 2 hour sessions. At the beginning of each session, catheters were flushed with 0.1 ml heparinised saline (10 IU/ml) and were connected to the infusion line. Lever extension and house light illumination indicated the initiation of the session. Levers were allocated as active or inactive, where the location of the active lever was counterbalanced across chambers. Depression of the active lever delivered a 3 s infusion of METH (0.1 mg/kg/infusion, 50 µL), illuminated the cue light, and extinguished the house light. The house light was extinguished for a 20 second time period during which depression of the active lever had no programmed consequences. Depression of the inactive lever had no programmed consequences at any time. At the end of each session, the infusion line was disconnected and catheters were flushed with 0.2 ml of cephazolin sodium in heparinized saline solution.

Prior to the initiation of the IVSA procedure, rats were habituated to the chambers. The levers were retracted and no infusions were available. The session was conducted for 60 minutes.

Experiment 1—Acquisition and Maintenance of METH IVSA

Rats acquired self-administration of METH during daily 2 hour fixed ratio 1 scheduled sessions. To avoid overdose, each rat was limited to a maximum of 60 infusions per session. Rats continued under the FR-1 schedule until stable responding was met as indicated by less than 10% variability in number of infusions and active lever presses compared to the day prior. Stable self-administration baselines were achieved within 10 days, after which rats advanced to the progressive ratio schedule.

Progressive Ratio Schedule

Under the progressive ratio (PR) schedule, METH infusions were delivered according to the ratio: $((5 \times (e^{reinforcer \; \# \times 0.2}) - 5)$. The number of active lever presses that were required to receive one METH infusion increased according to the following sequence: 1, 2, 4, 6, 9, 12, 15, 20, 25, 32, 40, 50, 62, 77, 95, 118, 145, 178, 219, 268 (Cornish et al., 2005). The daily PR sessions were completed after 2 hours or if an infusion had not been self-administered for 60 minutes. Rats continued with PR sessions until lever pressing stabilised, which was determined by less than 10% variability in number of infusions and active lever presses for two consecutive days. Lever pressing stabilised after 7 days. During this time, the rats were given a sham saline i.p. (1 ml/kg) injection prior to the session.

Once lever pressing had stabilised, testing with SOC-1 commenced. Each test day was separated by 2-3 PR scheduled sessions to regain their baseline level of responding for METH infusions. Rats received SOC-1 in an ascending dose sequence (0, 1.25, 2.5, 5, and 10 mg/kg), which was administered 15 minutes prior to the test session. On the final test session, rats received a vehicle injection to ensure that they continued to engage in similar lever pressing as on their first test session and that the lowered lever pressing evident on SOC-1 test days was due to the effects of the compound, not injection stress.

Experiment 2—Acquisition and Maintenance of METH IVSA

Acquisition and maintenance of METH IVSA in experiment 2 was identical to Experiment 1, except that IVSA sessions were conducted 5 days a week for 21 days.

Extinction

Following the last day of METH self-administration, rats were exposed to daily 2-hour extinction sessions. The sessions were identical to self-administration sessions except that depression of the active lever now resulted in a saline infusion coupled with illumination of the cue light and the max out criteria was omitted. Rats continued under extinction conditions for a minimum of ten days and until <25 lever presses were made per session for two consecutive days. During the second week of extinction, rats were given one sham saline i.p. (1 ml/kg saline) injection before the 2-hour session.

Reinstatement

Once extinction criteria were met, rats underwent reinstatement testing. Each reinstatement test session was separated by three extinction days. Prior to each reinstatement test session, rats received the first injection (DMSO and tween vehicle, C25 or SR49059) 5 minutes prior to the second injection (saline vehicle or SOC-1) after which they received their final injection (saline vehicle or METH) 5 minutes later and were then immediately placed in the chamber for 2 hours to measure lever pressing and locomotor activity.

Rats initially received SOC-1 in an ascending dose sequence (0, 2.5, 5, 10 mg/kg, i.p.) followed by a METH prime (1 mg/kg, i.p.). Following the completion of the first four reinstatement sessions, an antagonist pretreatment (C25 at a dose of 10 mg/kg i.p. or SR49059 at a dose of 1 mg/kg, i.p.) was administered before the SOC-1 10 mg/kg dose and METH prime. The antagonist injections were counterbalanced across two reinstatement sessions such that half of the rats received C25 and the other half received SR49059 before each session. On the reinstatement session subsequent to antagonist testing, rats received the highest tested dose of SOC-1 accompanied by vehicle injections to ensure that SOC-1 alone did not alter lever pressing activity. To also ensure that rats were continuing to reinstate to METH, additional reinstatement test sessions where rats received vehicle i.p. injections prior to a METH prime were included following the completion of the SOC-1 ascending dose test schedule and on the final reinstatement test session. Reinstatement conditions were identical to extinction sessions.

Statistical Analysis

Daily rates of active and inactive lever pressing during acquisition of self-administration was analysed using a two-way repeated measures analysis of variance (ANOVA) followed by planned pairwise comparisons. Number of infusions and active lever pressing across the 20-day period were also compared using a repeated-measures ANOVA to ensure rats acquired METH self-administration followed by planned pairwise comparisons. Locomotor activity throughout self-administration was analysed using a repeated measures ANOVA with planned pairwise comparisons.

The effect of SOC-1 on METH intake and active lever pressing under a progressive ratio schedule was analysed using a repeated measures ANOVA followed by planned pairwise comparisons. A comparison of active and inactive lever pressing after drug administration was undertaken using a two way repeated measures ANOVA. Locomotor activity following SOC-1 administration was also analysed using a repeated measures ANOVA followed by planned pairwise comparisons.

To assess whether rats extinguished METH-paired responses, mean active lever pressing from the last three METH self-administration sessions was compared to active lever pressing during the extinction sessions using a repeated measures ANOVA with planned comparisons, as was changes in locomotor activity.

To determine that rats reinstated METH-paired lever responding, active lever pressing from the last day of extinction prior to reinstatement was compared to active lever pressing during reinstatement testing using a two-way repeated measures ANOVA. Active and inactive lever pressing on reinstatement were compared using a two-way repeated measures ANOVA to ensure that rats continued to differentiate the levers. Locomotor activity was also analysed across extinction and reinstatement using a two-way repeated measures ANOVA. The effect of SOC-1 on reinstating METH-seeking behaviour was evaluated using a repeated measures ANOVA followed by planned pairwise comparisons. Statistical analyses were performed using SPSS 20 Graduate Student Version for Mac. In cases where the assumption of sphericity was violated, the Greenhouse-Geisser correction was reported. Statistical significance was set at $P<0.05$.

Results

Testing SOC-1 Under a Progressive Ratio Schedule

Figure 9:
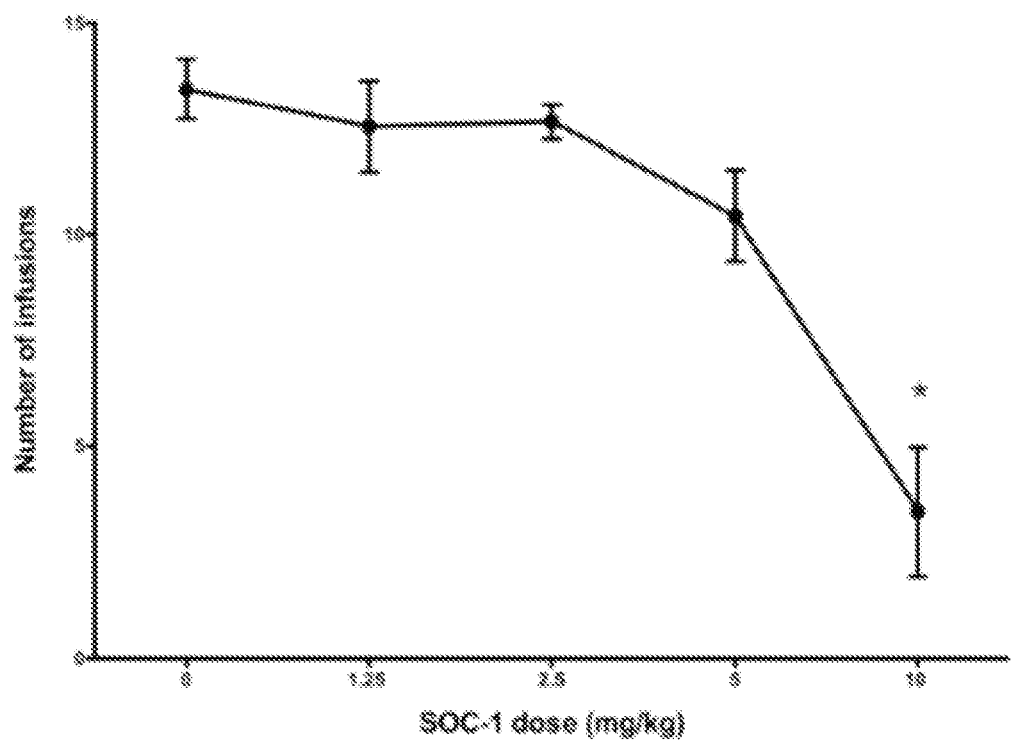
FIG. 9—The effect of SOC-1 on infusions in rats self-administering methamphetamine under a progressive ratio schedule. * indicates $p<0.05$ versus vehicle.
Figure 10:
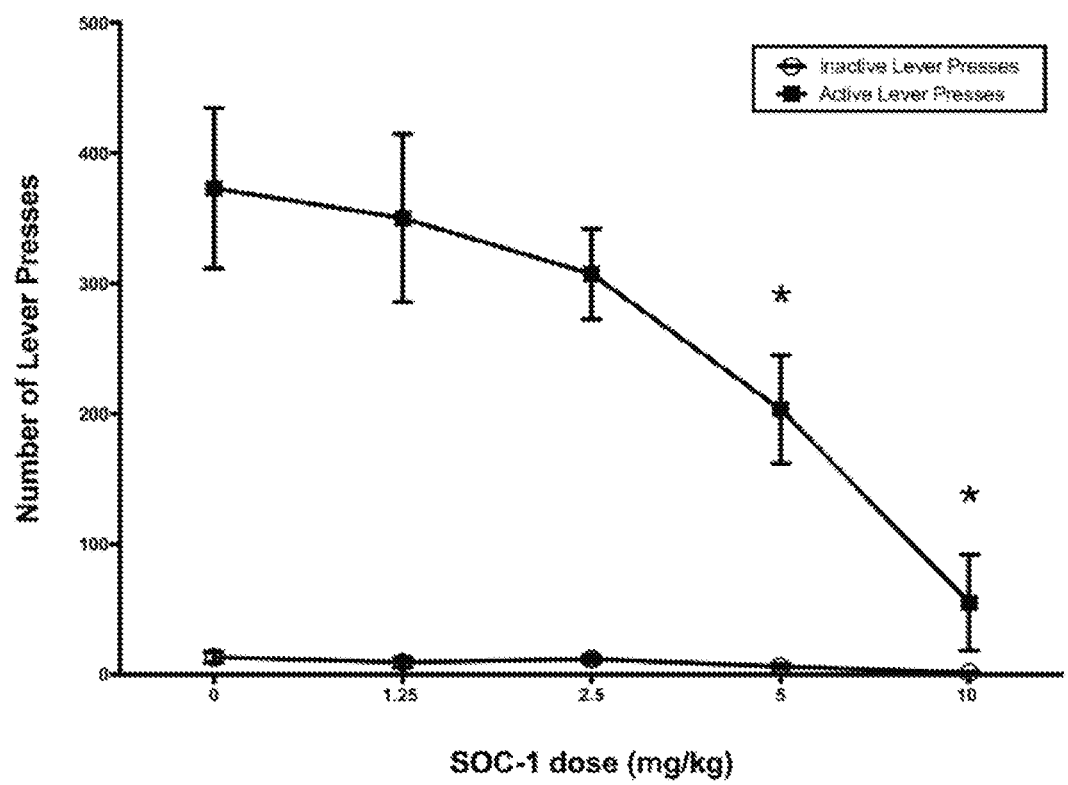
FIG. 10—The effect of SOC-1 on lever pressing in rats self-administering methamphetamine under a progressive ratio schedule. * indicates $p<0.05$ versus vehicle.
Figure 11:
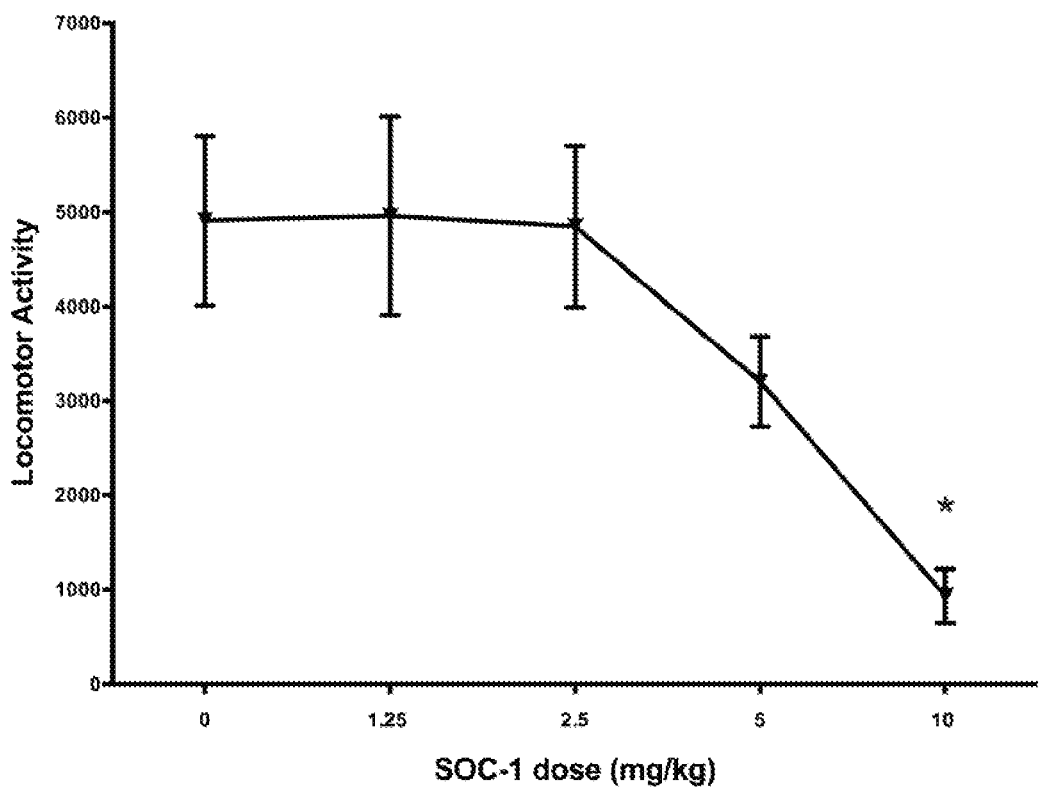
FIG. 11—The effect of SOC-1 on locomotor activity in rats self-administering methamphetamine under a progressive ratio schedule. * indicates $p<0.05$ versus vehicle.

FIG. 9, FIG. 10 and FIG. 11 show the effects of SOC-1 or vehicle on a) infusions (FIG. 9), b) lever pressing (FIG. 10), and c) locomotor activity (FIG. 11), in rats self-administering methamphetamine under a progressive ratio schedule. In these figures * indicates $p<0.05$ versus vehicle.

Following recovery from surgery for catheter implantation in the right jugular vein, male Sprague Dawley rats were trained during daily 2 hour FR-1 scheduled sessions to lever press for methamphetamine (0.1 mg/kg/infusion). Stable responses under the FR-1 schedule were achieved within 10 days. Rats were then transferred to a PR schedule, which they remained on for 7 days until their responding stabilised. Once their lever pressing stabilised, SOC-1 testing began. Each test day was separated by 2-3 PR scheduled sessions. Rats received SOC-1 in an ascending dose sequence (0, 1.25, 2.5, 5, and 10 mg/kg, IP), which was administered 15 minutes prior to the test session. On the final test session, rats received a vehicle injection.

SOC-1 administration significantly reduced active lever pressing under a PR schedule at doses of 5 mg ($p=0.043$) and 10 mg/kg ($p=0.007$) compared to vehicle administration. A significant reduction in infusion breakpoint and locomotor activity was evident following the 10 mg/kg dose ($p=0.001$ and $p=0.005$ respectively) when compared to vehicle administration. Active lever pressing ($p=0.236$), infusions (p=0.191), and locomotor activity (p=0.107) were not significantly different on the first compared to the last vehicle reinstatement session.

Testing SOC-1 on Methamphetamine-Primed Reinstatement

Figure 12:
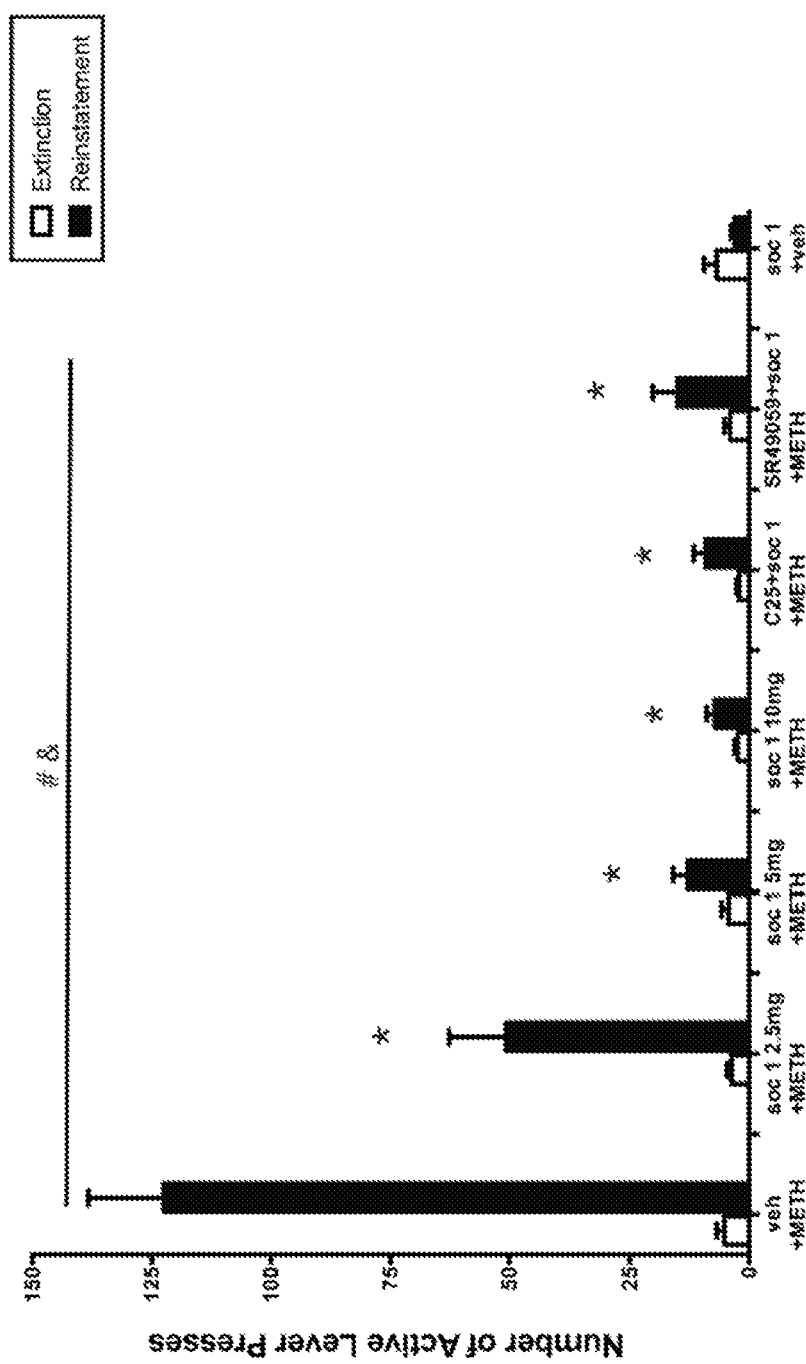
FIG. 12—The effect of vehicle, SOC-1, and combined SOC-1 with C25 or SR49059 administration on active lever presses during methamphetamine primed reinstatement. # denotes $p<0.05$ main effect of days, & indicates $p<0.05$ main effect of treatment and * denotes $p<0.05$ versus vehicle+METH condition.
Figure 13:
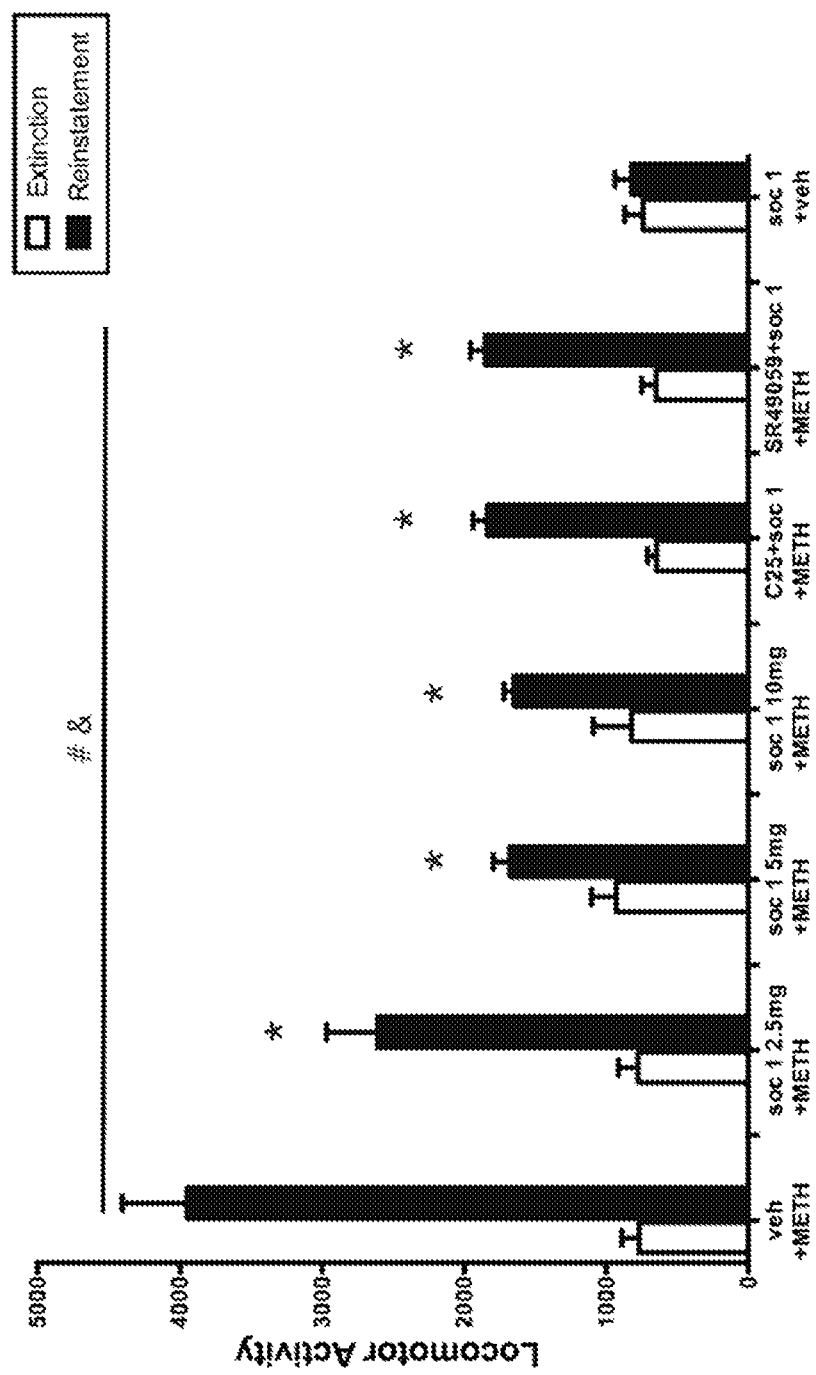
FIG. 13—The effect of vehicle, SOC-1, and combined SOC-1 with C25 or SR49059 administration on locomotor activity during methamphetamine primed reinstatement. # denotes $p<0.05$ main effect of days, & indicates $p<0.05$ main effect of treatment and * denotes $p<0.05$ versus vehicle+METH condition.

FIG. 12 and FIG. 13 show the effects of vehicle, SOC-1, and combined SOC-1 with C25 or SR49059 administration on a) active lever presses (FIG. 12) and b) locomotor activity (FIG. 13), during methamphetamine primed reinstatement. In these figures # denotes p<0.05 main effect of days, & indicates p<0.05 main effect of treatment and * denotes p<0.05 versus vehicle+METH condition.

Following recovery from surgery for catheter implantation in the right jugular vein, male Sprague Dawley rats were allowed to acquire self-administration of methamphetamine (0.1 mg/kg/infusion) during 2 hour FR-1 scheduled sessions conducted 5 days a week for 21 days. Following this, rats were exposed to daily 2-hour extinction sessions. Rats met the extinction criteria (minimum of 10 days and less than 25 active lever presses per session for 2 consecutive days) after 15 sessions. Once the extinction criteria were met, rats underwent reinstatement testing. Each reinstatement test session was separated by three extinction days. Prior to each reinstatement session, rats received the first injection (DMSO and tween vehicle, C25 or SR49059) 5 minutes prior to the second injection (saline vehicle or SOC-1) after which they received their final injection (saline vehicle or methamphetamine) 5 minutes later and were then immediately placed in the chamber for 2 hours. The treatment schedule was as follows: rats initially received SOC-1 in an ascending dose sequence (0, 2.5, 5, 10 mg/kg, IP) followed by a methamphetamine prime (1 mg/kg, IP). After this, an antagonist pre-treatment (C25 at a dose of 10 mg/kg IP or SR49059 at a dose of 1 mg/kg IP) was administered before the 10 mg/kg SOC-1 dose and methamphetamine prime. On the next session, rats received the 10 mg/kg SOC-1 dose prior to a vehicle injection to ensure that SOC-1 alone did not alter lever pressing activity. On the reinstatement session subsequent to SOC-1 dose testing and the final reinstatement session, additional vehicle+methamphetamine sessions were conducted to ensure that rats continued to reinstate.

Rats reinstated to their previous lever pressing activity as shown through a significant increase in active lever pressing on reinstatement compared to the prior extinction day (p<0.005). A comparison of vehicle administration to drug treatments on reinstatement sessions demonstrated that SOC-1 administration at doses of 2.5 mg (p<0.005), 5 mg (p<0.005), and 10 mg/kg (p<0.005) significantly reduced active lever pressing produced by a methamphetamine prime. Administration of an oxytocin receptor antagonist (C25) or a Via receptor antagonist (SR49059) failed to block the attenuating effect of SOC-1 administration on methamphetamine-primed reinstatement as shown through a significant reduction in active lever pressing (both p<0.005). SOC-1 administration on its own (SOC-1+vehicle) did not significantly alter lever-pressing activity when compared to the extinction day prior (p=0.147). On the additional vehicle reinstatement sessions, rats continued to reinstate to their prior active lever pressing activity (p<0.05).

Locomotor activity was also significantly higher on reinstatement sessions than on extinction sessions (p<0.005). Across reinstatement sessions, locomotor activity was significantly lower when 2.5 mg (p=0.006), 5 mg (p<0.005), and 10 mg/kg doses (p<0.005) of SOC-1 were administered prior to a methamphetamine prime. A similar effect was evident following the administration of oxytocin receptor (p<0.005) and Via receptor antagonists (p<0.005) prior to SOC-1 and methamphetamine administration. The sole administration of SOC-1 did not significantly change locomotor activity during reinstatement compared to the previous extinction session (p=0.472).

Example 9—Assessment of the Acute Toxicity of SOC-1 Test Item Following Intravenous Administration of a Single Bolus Dose to Sprague-Dawley Rats in a One Week Dose Range Finding Study The acute toxicity of the SOC-1 test item was assessed in Sprague Dawley rats following intravenous administration of a single bolus dose. A total of four groups of n=3 adult female rats were treated with 1, 3, 10 and 30 mg/kg doses of SOC-1. The rats were then observed for 7 days prior to termination on Study Day 8 without necropsy.

Treatment with SOC-1 test item was tolerated in this study at all dose levels. There were dose related findings of mild piloerection, hunched posture and gait and palpebral closure which were detected post-treatment on Study Day 1. These findings were generally resolved within 4-24 hours and are considered treatment related. There was also a finding of an exaggerated flinch reaction and vocalisation at the time of dose administration which was considered treatment related.

The acute tolerated dose of SOC-1 administered as a bolus intravenous injection in this study is identified as at least 30 mg/kg.

This test was conducted in compliance with the Organisation for Economic Co-operation and Development (OECD) Principles on Good Laboratory Practice (GLP) (revised 1997). Studies conducted according to OECD and US FDA Good Laboratory Practice standards are accepted by signatories to the OECD Mutual Acceptance of Data Agreement, including the USA and Japan.

The primary objective of this study was to investigate the tolerability and acute toxicity of the SOC-1 test item following administration of a single bolus dose by the intravenous route to adult Sprague Dawley rats.

This study was conducted in accordance with the guidelines set out in the National Health and Medical Research Council, Australian Code of Practice for the Care and Use of Animals for Scientific Purposes, 8th edition, 2013 (1). The study was assessed and approved by the University of Queensland Animal Ethics Committee.

Test and Vehicle/Control Item

The "Test Item" and "Vehicle/Control Item" are shown in Table 6 and Table 7, respectively.

TABLE 6

| Test item used the present example | |
| --- | --- |
| Identification | SOC-1 |
| Manufacturer | The University of Sydney, NSW 2006 Australia |
| Batch Number | TAR058-031115 |
| Molecular weight | 273.16 |
| Description | White/off-white powder |
| Storage Conditions | 2-8° C. |

TABLE 7

| Vehicle/Control item used in the present example | |
| --- | --- |
| Identification | Sodium Chloride Injection BP (0.9% saline) |

TABLE 7-continued

Vehicle/Control item used in the present example

| | |
|---|---|
| Manufacturer | Pfizer |
| Product ID | PF_0158594 |
| Batch Number | JT58 |
| Description | 0.9%; 90 mg sodium chloride in 10 mL water; 10 mL Steriluer ampoules |
| Storage Conditions | Ambient temperature |

Test and Control Formulation

The SOC-1 test item was dissolved in 0.9% saline for dose administration per Table 8. The formulations were prepared under clean conditions in a laminar flow hood using sterile polypropylene tubes, and with gentle swirling/vortexing to ensure the compound is fully dissolved in the vehicle prior to use.

TABLE 8

Dose formulation used in the present example

| | SOC-1 Treatment | | |
|---|---|---|---|
| Study Group | Dose Formulation (mg/mL) | Dose Volume (mL/kg) | Dose Rate (mg/kg) |
| 1 | 0.5 | 2 | 1 |
| 2 | 1.5 | 2 | 3 |
| 3 | 5 | 2 | 10 |
| 4 | 5 | 6 | 30 |

The test item formulations were maintained at ambient temperature on each day of use (and used on the same day). Dose formulation samples were not collected for this study.

GLP Reserve

The unused test item was retained at the test facility under appropriate storage conditions.

Animals

The details relating to the animals utilised in the study are shown in Table 9.

TABLE 9

Animals used in the present example

| | |
|---|---|
| Species | Rat |
| Strain | Sprague Dawley |
| Source | Animal Resources Centre Canning Vale WA 6970, Australia |
| Number of Animals | 12 females |
| Sex | Females (nulliparous and non-pregnant) |
| Weight at Start of Dosing | Females: 188 g to 215 g |
| Age at Start of Dosing | 6-8 weeks |
| Identification | Animals were identified by unique animal numbers which was associated with a microchip implanted subcutaneously into each animal at the time of receipt. A Mini-TracKer Reader (AVID Identification System. Inc.) was used to read the microchip prior to all procedures. Tails were also marked with permanent pen for identification within cages, but these marks were not used as the primary identifier for any animal. |
| Randomisation | Animals were randomly assigned to study treatment groups using Provantis 9.3.1.1. |

TABLE 9-continued

Animals used in the present example

| | |
|---|---|
| Acclimation | Animals were subject to at least a 5 day acclimation period prior to dose administration. This acclimation period included a health examination and only animals without visible signs of illness were used for the study. |

The Test System Environment is shown in Table 10.

TABLE 10

Test system environment used in the present example

| | |
|---|---|
| Housing | Animals were housed in their study groups with up to three animals per individually ventilated cage (IVC). Cages were changed once weekly. |
| Cage Clearance | Whenever animals are removed from a cage, all animals were returned to the cage prior to any animals being removed from another cage. |
| Air Flow | The IVC units have a minimum of 15 air changes per hour. |
| Bedding | Animal bedding (PuraChip Aspen Enrichment Bedding, Able Scientific Pty Ltd) |
| Environmental Enrichment | Environmental enrichment was added to each IVC. These items included chew sticks, rodent hutches and Alpha-Twist nesting material. |
| Feed | Autoclaved Rat and Mouse Pellets (Speciality Feeds, Glen Forest, WA, Australia). Pellets were available ad libitum throughout the study. |
| Water | Tap water (ad libitum). Water samples are analysed on a quarterly basis for the presence of any impurities which may interfere with interpretation of the study and these records are retained within the facility. |
| Temperature & Humidity | Housing Temperature: 23 ± 3° C. Housing Humidity: 50 ± 20% |
| Lighting | 12-hour light/dark cycle |

Methods

The design of this acute single dose toxicity study in rats was adapted from OECD Guideline for Testing of Chemicals No. 420 Acute Oral Toxicity—Fixed Dose Procedure' 2001 (2) and the test facility Standard Operating Procedure SP_T002 'Dose Range Finding Study in Rodents'. The study procedures were conducted as outlined below and according to related test facility Standard Operating Procedures.

The study design is summarised in Table 11.

TABLE 11

Study design used in the present example

| Group | SOC-1 (mg/kg) | Sprague Dawley Rats (female) | Termination Day |
|---|---|---|---|
| 1 | 1 | 3 | 8 |
| 2 | 3 | 3 | 8 |
| 3 | 10 | 3 | 8 |
| 4 | 30 | 3 | 8 |

The commencement of the study was staggered by two days between Groups 2 and 3 to allow for possible adjustment of each dose level based on toxicities at the preceding dose.

Briefly, on completion of the acclimation period the study was commenced with administration of the treatment on Study Day 1. The animals were observed for signs of toxicity throughout the in-life study period as outlined below. Body weights were also collected daily. On Study Day 8 the surviving animals were culled without necropsy.

Treatments

The test item treatments were administered as a bolus intravenous injection in a dose volume of 2 mL/kg on Study Day 1 with restraint on conscious animals (with the exception of Group 4 where the treatment was administered in a dose volume of 6 mL/kg on lightly anaesthetised animals following the administration of isofluorane anaesthetic).

Observations

Morbidity and mortality observations were recorded daily during the acclimation period and on Day 8, and twice daily from Day 1 through Day 7.

Clinical observations were conducted at least once during the acclimation period. Clinical observations were conducted at least once daily from Day 1 up to and including the day prior to termination. On the day of treatment the animals were monitored continuously for the first 30 min post-treatment with formal observations made at 30 minutes, 1 hour and 4 hours post-treatment.

The clinical observations included examination of animals for changes in skin and fur, eyes and mucous membranes, respiratory and circulatory function, gait and posture, behaviour, tremors or convulsions and any other abnormal findings.

The clinical observations also included daily examination of the tail for any injection site reaction (for example, erythema or oedema).

Body Weights

Body weight was recorded once during the acclimation period and daily from the time of treatment on Day 1 to Day 8. The mean body weight values for study days 1-8 are shown as group mean±standard deviation (SD) in FIG. 14.

Necropsy

On Day 8 all animals were subjected to a final body weight measurement and then euthanised by an overdose of pentobarbitone (via intraperitoneal injection). The carcasses were discarded without necropsy.

Data Collection and Evaluation

Data was collected using either Provantis v.9.3.1.1 or recorded on the appropriate TetraQ forms. The data was then tabulated using either Provantis v9.3.1.1, GraphPad Prism 6 and/or Excel 2010.

Morbidity and Mortality

There were no unscheduled deaths or findings of morbidity in this study.

Clinical Observations

There were findings of piloerection, hunched posture and gait and palpebral closure post-dose on Study Day 1 in the rats treated with 10 and 30 mg/kg of SOC-1 test item. These findings were graded as mild in severity with the exception of a finding of moderate palpebral closure for one rat. The findings were typically detected within 30 minutes of treatment and resolved within 4-24 hours post-dose, with the exception of one finding of mild piloerection which was resolved on Day 3. These findings are considered treatment-related.

There was also a finding that the Group 3 rats showed an exaggerated flinch reaction and vocalisation at the time of administration of the 10 mg/kg dose. The finding is considered treatment-related. The 30 mg/kg rats were subsequently administered isofluorane anaesthetic prior to dosing to facilitate dosing and minimise pain/distress to the animals.

There were no findings of injection site reactions.

Clinical findings are summarised in Table 12.

TABLE 12

Clinical signs incidence summary for the present example

| Finding | SOC-1 (mg/kg) | | | |
|---|---|---|---|---|
| | 1 | 3 | 10 | 30 |
| n | 3 | 3 | 3 | 3 |
| Number of abnormalities detected: | 3 | 3 | 0 | 0 |
| Piloerection- mild | 0 | 0 | 3 | 3 |
| Reduced activity- mild | 0 | 0 | 0 | 2 |
| Hunched posture or gait- mild | 0 | 0 | 3 | 0 |
| Palpebral closure- mild/moderate | 0 | 0 | 0 | 1 |

There were no effects of SOC-1 test item treatment on body weight. The body weights for all animals increased the study.

Figure 14:
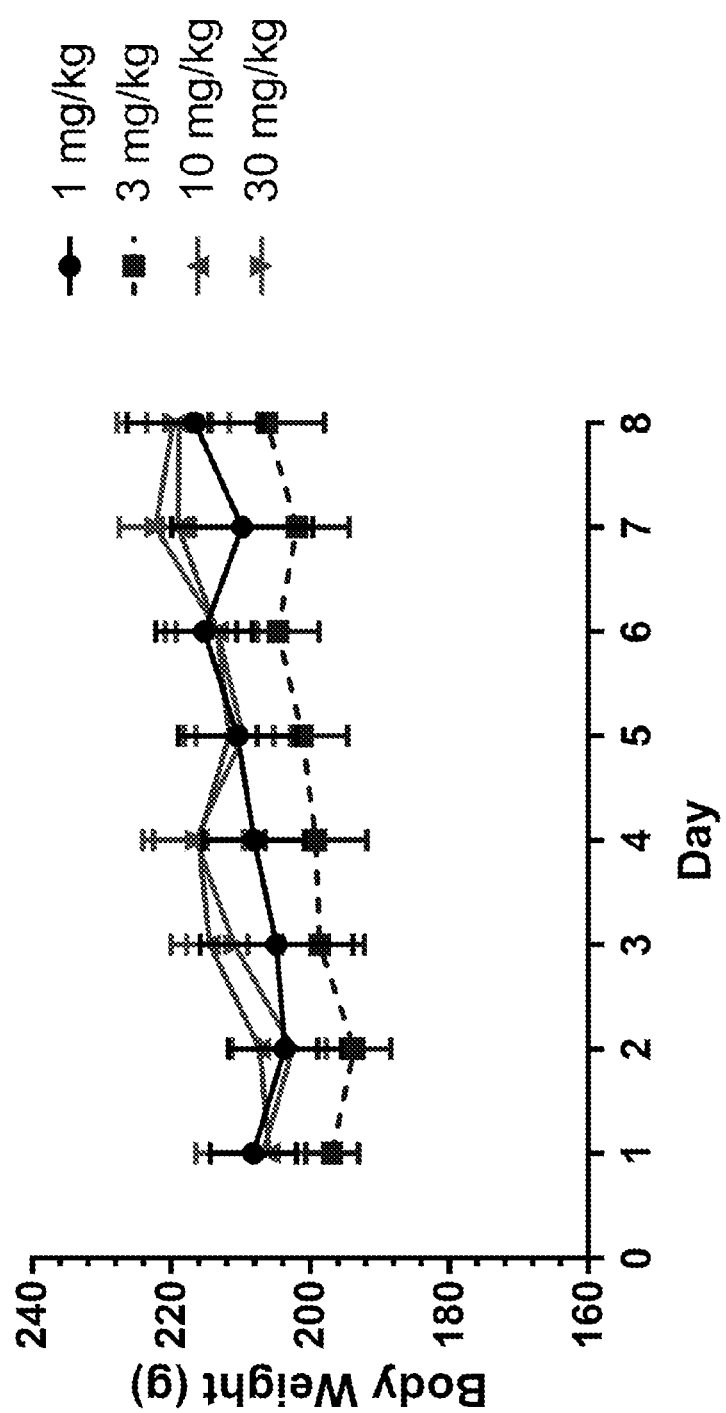
FIG. 14—Mean body weight values for Sprague Dawley rats consuming SOC-1.

Body weight values are summarised in FIG. 14 and Table 13.

TABLE 13

The mean bodyweights for rats used in groups 1 to 4 for the present example

| | | Bodyweight (g) Day numbers relative to start date | | | | | | | | | |
|---|---|---|---|---|---|---|---|---|---|---|---|
| Group | Animal | −5 | −3 | −1 | 1 | 2 | 3 | 4 | 5 | 6 | 7 | 8 |
| 1 | Mean | 179.667 | | 201.333 | 208.233 | 203.733 | 204.933 | 208.100 | 210.467 | 215.300 | 209.833 | 216.633 |
| | S.D. | 4.933 | | 6.028 | 6.204 | 8.140 | 11.0559 | 7.238 | 8.558 | 6.929 | 10.149 | 9.750 |
| | N | 3 | 0 | 3 | 3 | 3 | 3 | 3 | 3 | 3 | 3 | 3 |
| 2 | Mean | 178.667 | | 194.333 | 196.867 | 193.700 | 198.733 | 199.233 | 201.200 | 204.733 | 201.967 | 206.333 |
| | S.D. | 4.041 | | 5.58 | 3.850 | 5.257 | 6.430 | 7.304 | 6.534 | 5.935 | 7.559 | 8.355 |
| | N | 3 | 0 | 3 | 3 | 3 | 3 | 3 | 3 | 3 | 3 | 3 |
| 3 | Mean | | 200.667 | | 205.933 | 207.267 | 214.533 | 216.100 | 211.733 | 213.433 | 219.000 | 218.900 |
| | S.D. | | 5.033 | | 0.153 | 4.022 | 5.590 | 6.437 | 6.506 | 5.876 | 2.381 | 4.670 |
| | N | 0 | 3 | 0 | 3 | 3 | 3 | 3 | 3 | 3 | 3 | 3 |
| 4 | Mean | | 199.333 | | 206.833 | 202.567 | 210.967 | 216.500 | 209.667 | 213.367 | 222.300 | 219.767 |
| | S.D. | | 3.215 | | 9.672 | 4.769 | 6.824 | 7.608 | 6.800 | 7.534 | 5.257 | 8.059 |
| | N | 0 | 3 | 0 | 3 | 3 | 3 | 3 | 3 | 3 | 3 | 3 |

Conclusion

Treatment with SOC-1 test item was tolerated in this study at dose levels of 1, 3, 10 and 30 mg/kg. There were dose related findings of mild piloerection, hunched posture and gait and palpebral closure which were detected post-treatment on Study Day 1. These findings were generally resolved within 4-24 hours and are considered treatment related. There was also a finding of an exaggerated flinch reaction and vocalisation in the 10 mg/kg treated rats at the time of dose administration which was considered treatment related and is consistent with acute local venous irritation.

The acute tolerated dose of SOC-1 administered as a bolus intravenous injection in this study is identified as at least 30 mg/kg.

Example 10—A 24-Hour Pharmacokinetic Study in Sprague Dawley Rats with SOC-1 Test Item Administered by the Intravenous Route A single intravenous 20 mg/kg (corresponding to ~17.1 mg/kg expressed as the free base corrected for purity) bolus dose of SOC-1 test item formulated in Hartman's solution was administered to three adult male Sprague Dawley rats. A total of 10 blood samples were collected from each rat at time points ranging from pre-dose to 24 hours post-dose. The blood samples were subsequently processed to plasma and analysed for plasma concentrations of SOC-1 using a screening LC-MS/MS method (assay range=50-5000 ng/mL). Pharmacokinetic parameters were estimated from the plasma concentration versus time data by non-compartmental methods using Phoenix 64 WinNonlin® software.

This study was undertaken to evaluate the pharmacokinetics of SOC-1 following intravenous (i.v.) administration to male Sprague Dawley rats over a 24 hour period. The compound was administered as a bolus i.v. dose formulated using Hartman's solution (saline) to a group of n=3 rats at a rate of 20 mg/kg (17.1 mg/kg expressed as the free base corrected for purity). A total of ten blood samples were collected from each rat at time points ranging from pre-dose to 24 hours post-dose. These samples were subsequently processed to plasma and analysed for the concentration of SOC-1 using an LC-MS/MS based screening bioanalytical method.

The objective of this study was to investigate the pharmacokinetics of the SOC-1 test item following administration of a single bolus dose at 20 mg/kg by the intravenous route to adult Sprague Dawley rats.

This study was conducted in accordance with the guidelines set out in the National Health and Medical Research Council, Australian Code of Practice for the Care and Use of Animals for Scientific Purposes, 8th edition, 2013 (1). The study was assessed and approved by the University of Queensland Animal Ethics Committee.

Test and Vehicle/Control Item

The "Test Item" "Bioanalytical Reference Item" and "Vehicle/Control Item" are shown in Table 14, Table 15 and Table 16, respectively.

TABLE 14

Test item used in the present example

| | |
|---|---|
| Identification | SOC-1 |
| Manufacturer | The University of Sydney, NSW 2006 Australia |
| Batch Number | TAR058-031115 |
| Molecular weight | 273.16 (as the hydrochloride salt) |
| Description | White/off-white powder |
| Storage Conditions | 2-8° C. |

TABLE 15

Bioanalytical reference item used in the present example

| | |
|---|---|
| Identification | SOC-1 |
| Manufacturer | The University of Sydney, NSW 2006 Australia |
| Batch Number | TAR090-01-12-15 |
| Molecular weight | 273.16 (as the hydrochloride salt) |
| Purity (HPLC) | 98.65% |
| Description | White/off-white powder |
| Storage Conditions | 2-8° C. |

TABLE 16

Vehicle/Control item used in the present example

| | |
|---|---|
| Identification | Compound Sodium Lactate Intravenous Infusion BP (Hartmann's solution) |
| Manufacturer | Baxter |
| Product ID | Baxter AHB 2323 |
| Description | Sterile solution for intravenous infusion |
| Storage Conditions | Ambient temperature |

Test and Control Formulation

The SOC-1 test item was dissolved in Hartmann's solution at a final concentration of 5 mg/mL for dose administration. The formulation were prepared under clean conditions in a laminar flow hood using sterile polypropylene tubes and with gentle swirling/vortexing to ensure the compound was fully dissolved in the vehicle prior to use.

The test item formulation was maintained at ambient temperature and used on the same day. Dose formulation analysis samples were not collected for this study.

Animals

The details relating to the animals utilised in the study are shown in Table 17.

TABLE 17

Animals used in the present example

| | |
|---|---|
| Species | Rat |
| Strain | Sprague Dawley |
| Source | Animal Resources Centre Canning Vale WA 6970, Australia |
| Number of Animals | 3 male rats |
| Sex | Male |
| Weight at Start of Dosing | 304-328 gram |
| Age at Start of Dosing | 8-12 weeks |
| Identification | Animals were identified by unique animal numbers which was associated with a microchip implanted subcutaneously into each animal at the time of receipt. A Mini-TracKer Reader (AVID Identification System. Inc.) was used to read the microchip prior to all procedures. Tails were also marked with permanent pen for identification within cages, but these marks were not used as the primary identifier for any animal. |
| Acclimation | Animals were subject to a 4 day acclimation period prior to surgical cannulation. This acclimation period included a health examination and only animals without visible signs of illness were used for the study. |

Sprague Dawley rats are regarded as an acceptable and commonly used species for pharmacokinetics studies.

The Test System Environment is shown in Table 18.

TABLE 18

Test system environment used in the present example

| | |
|---|---|
| Housing | Animals were housed in groups of up to three per cage prior to cannulation. After cannula placement the animals were housed individually in metabolic cages for dose administration and blood sampling. |
| Air Flow | The IVC units have a minimum of 15 air changes per hour. |
| Bedding | Animal bedding (PuraChip Aspen Enrichment Bedding, Able Scientific Pty Ltd) |
| Environmental Enrichment | Environmental enrichment was added to each IVC. These items included chew sticks, rodent hutches and Alpha-Twist nesting material. |
| Feed | Autoclaved Rat and Mouse Pellets (Speciality Feeds, Glen Forest, WA, Australia). Pellets were available ad libitum throughout the study. |
| Water | Tap water (ad libitum). Water samples are analysed on a quarterly basis for the presence of any impurities which may interfere with interpretation of the study and these records are retained within the facility. |
| Temperature & Humidity | Housing Temperature: 23 ± 3° C. Housing Humidity: 50 ± 20% |
| Lighting | 12-hour light/dark cycle |

Methods

The pharmacokinetics study was conducted according to the UOS-004 Study Plan and related test facility Standard Operating Procedures (SOPs) as outlined below. The study design is shown in Table 19.

TABLE 19

Study design used in the present example

| Group | Test Item | Formulation (mg/mL) | Dose Rate (mL/kg) | Dose (mg/kg) | Males |
|---|---|---|---|---|---|
| 1 | SOC-1 | 5 | 4 | 20[a] | 3 |

[a] ~17.1 mg/kg expressed as the free base and corrected for purity.

Prior to treatments the rats were subject to surgery to cannulate the jugular vein (for dose administration, IV) and femoral artery (for blood sample collection, IA) with exteriorisation of the cannulas per test facility SOPs. Following recovery from surgery the rats were transferred to a Culex system for dose administration and blood sampling (with both lines tended per test facility SOPs).

The intravenous treatments were administered via the jugular cannula with a dosing volume of 4.0 mL/kg on the day following surgery. The treatments were followed by ~200 μL vehicle to ensure a full dose was delivered to the animals.

Blood samples (~250 μl) were collected in lithium heparin tubes from the IA cannula at the following time points: pre-dose, 2, 5, 10, 30, 60 minutes, 2, 4, 8 and 24 hours post-dose Blood samples were kept on ice immediately after collection to minimize degradation and centrifuged as soon as possible at approximately 4000×rcf for 10 min. Pre-dose samples were centrifuged separately prior to dosing. The plasma was then transferred to polypropylene tubes and stored frozen at −80° C.

After the last sample has been collected the animals were euthanased with Lethabarb™ administered via the IV cannula at 325 mg/kg.

Study samples were subsequently transferred on dry-ice for measurement of SOC-1 concentrations.

Body weight values were collected immediately prior to surgery. Morbidity and mortality checks were completed once daily during the acclimation period and at least twice during the study.

SOC-1 Plasma Concentration Analysis

Plasma concentrations of SOC-1 were determined using a screening LC-MS/MS method with a following liquid/liquid extraction. Briefly, 50 μL aliquots of the test samples and calibration standards were mixed with 1 mL of hexane:dichloromethane (1:1) for 5 minutes following the addition of 10 μl of internal standard, then centrifuged and the organic phase decanted and dried under nitrogen. The samples were then reconstituted with 0.5 mL of 0.1% formic acid in 30% methanol in deionised water and 0.2 mL transferred to a 96 well plate. A 5 μL aliquot of this sample was then analysed using an ABSciex API 4000 MS/MS coupled to a Shimadzu Prominence HPLC. The HPLC gradients included 0.1% formic acid in deionised water (Mobile Phase A) and 0.1% formic acid in methanol (Mobile Phase B). The LC-MS/MS instrument settings are summarised in Appendix 2. The samples were analysed with calibrated samples (50 to 5000 ng/mL) and concentration data determined by back calculation from the standard curve.

Plasma concentration data was derived using Analyst™ v1.6.1 (AB Sciex) software. The data was then tabulated using either GraphPad Prism 6 and/or Excel 2010.

Group mean±standard error values for plasma concentration versus time values were determined using Phoenix 64 WinNonlin software. The following pharmacokinetic parameters were also calculated by non-compartmental methods, using Phoenix 64 WinNonlin software:

Rsq—Coefficient of association for the terminal elimination phase (R2).

Lambda—Terminal elimination rate constant associated with the terminal (log-linear) portion of the curve (1/h).

$T_{1/2}$—Terminal elimination half-life (h)

$C_0$—Initial concentration at time 0 min (ng/mL) determined by back-extrapolating from the first two measured concentration values.

$T_{max}$—Time to maximum plasma concentration following extravascular administration.

$C_{max}$—Maximum plasma concentration following extravascular administration $AUC_{last}$—Area under the curve from the time of dosing (Dosing time, time 0 min) to the last measurable concentration (ng·h/mL).

$AUC_{inf}$—AUC from Dosing time extrapolated to infinity, based on the last observed concentration (obs). (ng·h/mL).

AUC % Extrap—Percentage of AUCinf due to extrapolation from time of last measurable concentration to infinity.

$V_z$—Volume of distribution (L/kg).

Cl—Total body clearance (L/h/kg).

Note: Terminal elimination phase parameters were not reported if either R2<0.85 and/or AUC % Extrapolation>20%.

Body Weights and Clinical Signs

The SOC-1 treatments were tolerated and there were no findings of morbidity or mortality. Individual body weight values prior to treatment are shown in Table 20.

TABLE 20

Body weights for rats used in the present example

| Treatment | Rat ID | Body Weight[a] (g) |
|---|---|---|
| SOC-1 (20 mg/kg)[b] | Rat #1 | 328.4 |
| | Rat #2 | 316.2 |
| | Rat #3 | 304.3 |

[a] Body weight values were determined at the time of surgery on the day prior to treatment.
[b] 17.1 mg/kg expressed as the free base corrected for purity.

Plasma Concentration versus Time Data

Figure 15:
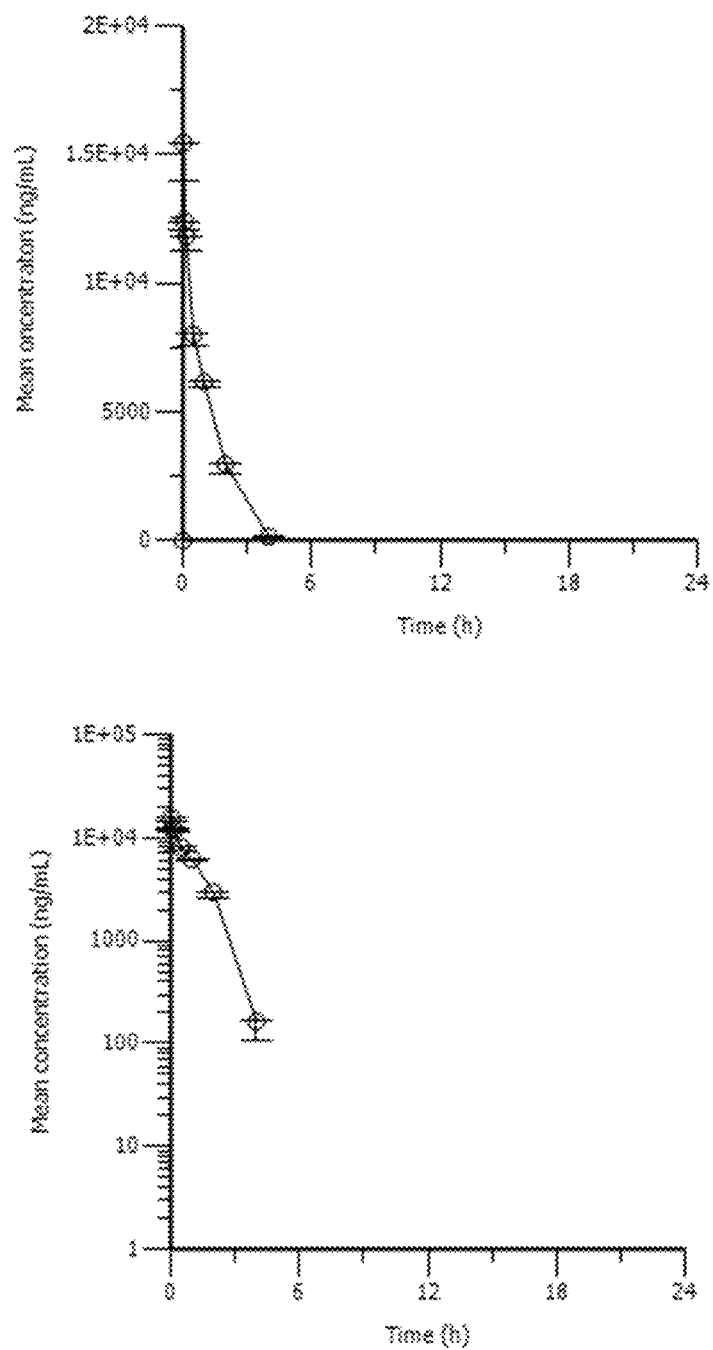
FIG. 15—Mean (+standard error of the mean (SEM)) plasma SOC-1 concentration versus time plots for Sprague Dawley rats.

Individual and mean plasma SOC-1 concentration versus time results are shown in Table 21 and FIG. 15.

TABLE 21

SOC-1 plasma concentration versus time for rats utilised in the present example

| | Plasma SOC-1 (ng/mL) | | |
|---|---|---|---|
| Time Post-Dose | Rat #1 | Rat #2 | Rat #3 |
| Pre-dose | BLOQ[a] | BLOQ[a] | BLOQ[a] |
| 2 | 17200 | 12600 | 16500 |
| 5 | 11900 | 13100 | 12200 |
| 10 | 12800 | 10900 | 11700 |
| 30 | 7120 | 8790 | 8120 |
| 1 | 5720 | 6480 | 6310 |
| 2 | 2310 | 3610 | 2980 |
| 4 | 115 | 286 | 97.3 |
| 8 | BLOQ[a] | BLOQ[a] | BLOQ[a] |
| 24 | BLOQ[a] | BLOQ[a] | BLOQ[a] |

[a] BLOQ = below lower limit of quantitation of 50 ng/mL.
SOC-1 plasma concentration versus time data determined after administration of a single intravenous 20 mg/kg (17.1 mg/kg expressed as the free base corrected for purity) bolus dose to male Sprague Dawley rats.

Pharmacokinetic Parameters

Pharmacokinetic parameters are summarized in Table 22.

TABLE 22

SOC-1 Pharmacokinetic parameters observed in the present example

| Rat ID | Rsq | Lambda (1/h) | $T_{1/2}$ (h) | $C_0$ (ng/mL) | $AUC_{last}$ (ng · h/mL) | $AUC_{inf}$ (ng · h/mL) | AUC % Extrap (%) | Vz (L/kg) | Cl (L/h/kg) |
|---|---|---|---|---|---|---|---|---|---|
| #1 | 0.988 | 1.33 | 0.521 | 21900 | 15400 | 15500 | 0.559 | 0.831 | 1.11 |
| #2 | 0.976 | 1.07 | 0.646 | 12600 | 18100 | 18400 | 1.45 | 0.868 | 0.931 |
| #3 | 0.973 | 1.44 | 0.483 | 20100 | 17000 | 17000 | 0.398 | 0.699 | 1.00 |
| N | 3 | 3 | 3 | 3 | 3 | 3 | 3 | 3 | 3 |
| Mean | 0.979 | 1.28 | 0.550 | 18200 | 16800 | 17000 | 0.803 | 0.799 | 1.01 |
| SE | 0.00452 | 0.108 | 0.0494 | 2860 | 790 | 840 | 0.328 | 0.0512 | 0.0507 |
| CV % | 0.800 | 14.6 | 15.6 | 27.2 | 8.14 | 8.58 | 70.7 | 11.1 | 8.66 |

SOC-1 plasma concentration versus time data determined after administration of a single intravenous 20 mg/kg (17.1 mg/kg expressed as the free base corrected for purity) bolus dose to male Sprague Dawley rats.

Briefly, following intravenous administration of 20 mg/kg SOC-1 (17.1 mg/kg expressed as the free base corrected for purity) the mean (±standard error of the mean (SEM)) values for $C_0$ and $AUC_{inf}$ were 18200 (±2860) ng/mL, and 17000 (±840) ng·h/mL, respectively. The mean (±SEM) value for T½ was estimated at 0.550 (±0.049) h, and the mean (±SEM) values for $V_z$ and Cl were 0.799 (±0.051) L/kg and 1.01 (±0.051) L/h/kg, respectively.

Visual inspection of the data indicates that the concentration versus time data declined mono-exponentially, However, it is possible that the observed reduction in plasma concentration may only reflect redistribution of SOC-1, and not elimination, as the terminal elimination phase for SOC-1 may not have been captured. The terminal elimination phase may be more accurately defined using an assay with improved sensitivity that enables quantification of sample concentrations beyond 4 hours.

Conclusion

The pharmacokinetics of SOC-1 have been characterized in this study following administration of a single 20 mg/kg (~17.1 mg/kg expressed as the free base corrected for purity) bolus dose by the intravenous route in adult male Sprague Dawley rats.

Example 11—Assessment of the Acute Toxicity of SOC-1 Test Item Following Intravenous Administration of a Single Bolus Dose of 50 mg/kg to Sprague-Dawley Rats in a One Week Dose Range Finding Study The acute toxicity of SOC-1 test items was assessed in Sprague Dawley rats following intravenous administration of a single bolus dose of 50 mg/kg. A total of n=3 adult female rats were treated and then observed for 7 days prior to termination on Study Day 8 without necropsy.

Treatment with SOC-1 test item was tolerated in this study at a dose level of 50 mg/kg. There were findings of mild piloerection and reduced activity levels detected post-treatment on Study Day 1. These findings were resolved within 4 hours and are considered treatment related.

The acute tolerated dose of SOC-1 administered as a bolus intravenous injection in this study is identified as at least 50 mg/kg.

The nonclinical toxicity study described here entailed intravenous administration of a single bolus dose of SOC-1 to adult Sprague Dawley rats followed by a one week observation period. A previous study conducted at the test facility has shown that treatment at up to 30 mg/kg is tolerated in rats (1). The dose range finding study described here included administration of a 50 mg/kg dose of test article. This dose is considered a maximum feasible dose for administration via the intravenous route with the existing 5 mg/mL formulation.

The objective of this study was to investigate the tolerability and acute toxicity of the SOC-1 test item following administration of a single bolus dose of 50 mg/kg by the intravenous route to adult Sprague Dawley rats.

This study was conducted in accordance with the guidelines set out in the National Health and Medical Research Council, Australian Code of Practice for the Care and Use of Animals for Scientific Purposes, 8th edition, 2013 (1). The study was assessed and approved by the University of Queensland Animal Ethics Committee.

Test and Vehicle/Control Item

The "Test Item" and "Vehicle/Control Item" are shown in Table 23 and, Table 24, respectively.

TABLE 23

Test Item used in the present example

| | |
|---|---|
| Identification | SOC-1 |
| Manufacturer | The University of Sydney, NSW 2006 Australia |
| Batch Number | TAR058-031115 |
| Molecular weight | 273.16 |
| Description | White/off-white powder |
| Storage Conditions | 2-8° C. |

TABLE 24

Vehicle/Control item used in the present example

| | |
|---|---|
| Identification | Compound Sodium Lactate Intravenous Infusion BP (Hartmann's solution) |
| Manufacturer | Baxter |
| Product ID | Baxter AHB 2323 |
| Batch Number | 588A2 |
| Description | Sterile solution for intravenous infusion |
| Expiry Date | February 2017 |
| Storage Conditions | Ambient temperature |

Test and Control Formulation

The SOC-1 test item was dissolved in Hartmann's solution at a final concentration of 5 mg/mL for dose administration. The formulation were prepared under clean conditions in a laminar flow hood using sterile polypropylene tubes and with gentle swirling/vortexing to ensure the compound was fully dissolved in the vehicle prior to use.

The test item formulation was maintained at ambient temperature and used on the same day. Dose formulation analysis samples were not collected for this study.

Animals

The details relating to the animals utilised in the study are shown in Table 25.

TABLE 25

Animals used in the present example

| | |
|---|---|
| Species | Rat |
| Strain | Sprague Dawley |
| Source | Animal Resources Centre Canning Vale WA 6970, Australia |
| Number of Animals | 3 females |
| Sex | Females (nulliparous and non-pregnant) |
| Weight at Start of Dosing | Females: 215 g to 229 g |
| Age at Start of Dosing | 6-8 weeks |
| Identification | Animals were identified by unique animal numbers which was associated with a microchip implanted subcutaneously into each animal at the time of receipt. A Mini-TracKer Reader (AVID Identification System. Inc.) was used to read the microchip prior to all procedures. Tails were also marked with permanent pen for identification within cages, but these marks were not used as the primary identifier for any animal. |

TABLE 25-continued

Animals used in the present example

| | |
|---|---|
| Acclimation | Animals were subject to an 8 day acclimation period prior to dose administration. This acclimation period included a health examination and only animals without visible signs of illness were used for the study. |

Sprague Dawley rats are found to be an acceptable and commonly used species for toxicology studies. The study included the use of female rats only to minimise animal usage.

The test system environment is shown in Table 26.

TABLE 26

Test system environment used in the present example

| | |
|---|---|
| Housing | Animals (n = 3) were group housed in their animals in an individually ventilated cage (IVC). Cages were changed once weekly. |
| Air Flow | The IVC units have a minimum of 15 air changes per hour. |
| Bedding | Animal bedding (PuraChip Aspen Enrichment Bedding, Able Scientific Pty Ltd) |
| Environmental Enrichment | Environmental enrichment was added to each IVC. These items included chew sticks, rodent hutches and Alpha-Twist nesting material. |
| Feed | Autoclaved Rat and Mouse Pellets (Speciality Feeds, Glen Forest, WA, Australia). Pellets were available ad libitum throughout the study. |
| Water | Tap water (ad libitum). Water samples are analysed on a quarterly basis for the presence of any impurities which may interfere with interpretation of the study and these records are retained within the facility. |
| Temperature & Humidity | Housing Temperature: 23 ± 3° C. Housing Humidity: 50 ± 20% |
| Lighting | 12-hour light/dark cycle |

Methods

The design of this acute single dose toxicity study in rats was adapted from OECD Guideline for Testing of Chemicals No. 420 Acute Oral Toxicity—Fixed Dose Procedure' 2001 (3) and the test facility Standard Operating Procedure SP_T002 'Dose Range Finding Study in Rodents'. The study procedures were conducted as outlined below and according to related test facility Standard Operating Procedures.

The study design is summarised in Table 27.

TABLE 27

Study design used in the present example

| Group | SOC-1 (mg/kg) | Sprague Dawley Rats (female) | Termination Day |
|---|---|---|---|
| 1 | 50 | 3 | 8 |

Briefly, on completion of the acclimation period the study was commenced with administration of the treatment on Study Day 1. The animals were observed for signs of toxicity throughout the in-life study period as outlined below. Body weights were also collected daily. On Study Day 8 the surviving animals were culled without necropsy.

Treatments

The 5 mg/mL test item treatments were administered as a bolus intravenous injection in a dose volume of 10 mL/kg on Study Day 1 with restraint on conscious animals.

Observations

Morbidity and mortality observations were recorded daily during the acclimation period and on Day 8, and twice daily from Day 1 through Day 7.

Clinical observations were conducted at least once during the acclimation period. Clinical observations were conducted at least once daily from Day 1 up to and including the day prior to termination. On the day of treatment the animals were monitored continuously for the first 30 minutes post-treatment with formal observations made at 30 minutes, 1 hour and 4 hours post-treatment.

The clinical observations included examination of animals for changes in skin and fur, eyes and mucous membranes, respiratory and circulatory function, gait and posture, behaviour, tremors or convulsions and any other abnormal findings.

The clinical observations also included daily examination of the tail for any injection site reaction (for example, erythema or oedema).

Body Weights

Body weight was recorded once during the acclimation period and daily from the time of treatment on Day 1 to Day 8.

Necropsy

On Day 8 all animals were subjected to a final body weight measurement and then euthanised by an overdose of pentobarbitone (via intraperitoneal injection). The carcasses were discarded without necropsy.

Data Collection and Evaluation

Data was collected manually and tabulated using either GraphPad Prism 6 and/or Excel 2010.

Morbidity and Mortality

There were no unscheduled deaths or findings of morbidity in this study.

Clinical Observations

There were findings of mild piloerection and reduced activity levels post-dose on Study Day 1 in the rats treated with 50 mg/kg of SOC-1 test item. These findings were typically detected within 30 minutes of treatment and were resolved within 4 hours post-dose. These findings are considered treatment-related. There was also a finding of hunched posture or gait for one animal on Study Day 5 only which is considered incidental and unrelated to treatment. There were no findings of injection site reactions and the clinical findings are shown in Table 28.

TABLE 28

Clinical signs incidence summary for rats used in the present example

| Finding | SOC-1 (mg/kg) 50 |
|---|---|
| n | 3 |
| No abnormalities detected: | 0 |
| Piloerection- mild | 1 |
| Reduced activity | 3 |
| Hunched posture or gait- mild | 1 |

The body weights for all animals increased or were stable during the study. There were no body weight findings that were considered treatment related.

Figure 16:
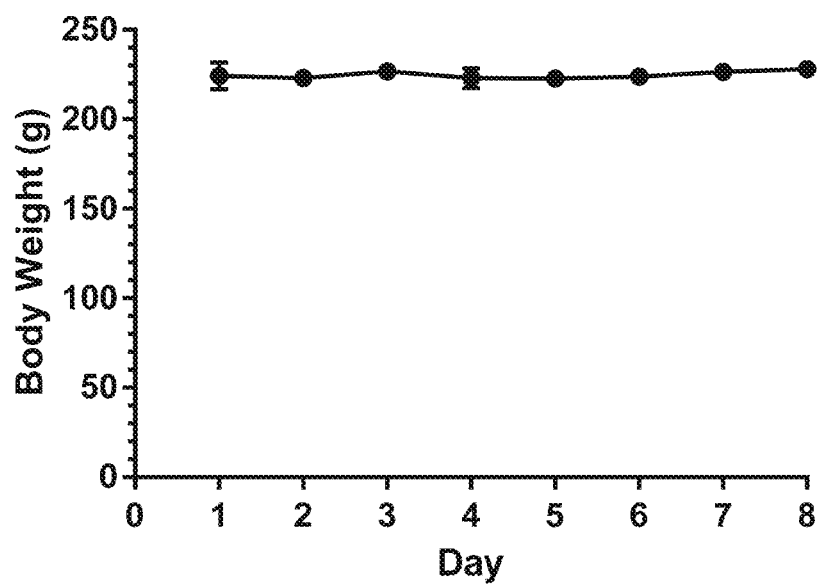
FIG. 16—Mean body weight values for study days for Sprague Dawley rats administered SOC-1.

Body weight values are summarised in FIG. 16 and Table 29 and individual body weight values are shown in Table 30.

TABLE 29

Mean body weights ± standard deviation (SD) for rats used in the present example

| Study Day | Body Weight (g) |
|---|---|
| 1 | 224.30 ± 7.45 |
| 2 | 223.07 ± 4.37 |
| 3 | 226.87 ± 4.33 |
| 4 | 223.03 ± 5.34 |
| 5 | 222.77 ± 4.75 |
| 6 | 223.80 ± 3.70 |
| 7 | 226.60 ± 2.57 |
| 8 | 228.03 ± 3.81 |

TABLE 30

Body weight values for individual rats used in the present example

| SOC-1 (mg/kg) | Rat ID | Study Day 1 | 2 | 3 | 4 | 5 | 6 | 7 | 8 |
|---|---|---|---|---|---|---|---|---|---|
| 50 | 1 | 228.4 | 220.9 | 225.1 | 229.2 | 219.0 | 220.7 | 225.7 | 229.1 |
| | 2 | 215.7 | 220.2 | 223.7 | 220.1 | 221.2 | 222.8 | 224.6 | 223.8 |
| | 3 | 228.8 | 228.1 | 231.8 | 219.8 | 228.1 | 227.9 | 229.5 | 231.2 |

Body weight values are shown in grams.

Conclusion

Treatment with SOC-1 test item was tolerated in this study at a dose level of 50 mg/kg. There were findings of mild piloerection and reduced activity levels detected post-treatment on Study Day 1. These findings were resolved within 4 hours and are considered treatment related.

It is noted that in a prior study conducted in Sprague Dawley rats that intravenous administration of 10 mg/kg SOC-1 formulated in normal saline was associated with unusual vocalisation and flinch reactions at the time of dosing (1). The administration of 50 mg/kg of SOC-1 formulated in Hartman's solution was not associated with similar reactions in the current study.

The acute tolerated dose of SOC-1 administered as a bolus intravenous injection in this study is identified as 50 mg/kg.

Example 12—Assessment of Alcohol Intake in Baboons Administered SOC-1 Animals

Baboons are regarded as an ideal subject for these studies as the technical field provides sufficient data on alcohol effects in baboons, and responses to feeding manipulations, and operant conditioning are also well studied. The inventors chose to use baboons as the model for alcohol dependence, as baboons will drink heavily, and can be trained to work for alcohol and palatable food rewards. In addition, non-human primates share more homology with the human brain than rodents, The baboons were obtained from World Wide Primates in Florida. The four baboons utilised in the study were part of a larger cohort that had been used in other research, but have not been enrolled in other types of research in more than a year. The four included here were chosen out of an original groups of 8. These 4 were willing to drink alcohol in high quantities, and were chosen for the study protocol. The previous research performed by these baboons included responding for food and drugs (e.g., methamphetamine).

The previous research did not include any surgical procedures or the induction of dependence to drugs of abuse.

The four baboons had a history of moderate drinking. These animals were involved in a previous protocol where they were given limited access to alcohol. Under these conditions, they willingly drank between 0.9 and 1.5 g/kg in two hours on intermittent days.

The baboons were housed in innovative enclosures that consisted of a standard squeeze-back housing cage with a large solid bench running front to back attached to a custom-designed cage extension that had a large perch located at the front of cage with sufficient room for the baboons to sit either below perch or on top of the perch. Sitting on top of the perch was the preferred position for the majority of the animals. This arrangement allowed the animals to walk between cages, use the perch, use the bench, prop themselves up by placing their feet on the ledges half way up each cage, or sit on the floor. This innovative enclosure enabled the provision of a stable housing environment within which could maintain healthy non-human primates for many years, as required by our long-term behavioural and imaging studies.

Alcohol Self-Administration

The baboons were already trained to self-administer 4-8% alcohol (w/v) using a sweetened alcohol procedure. The baboons were accustomed to lever pressing for rewards and were previously trained to respond for sweetened kool-aid. Once responding for kool-aid (mixed to ¼ strength of package instructions) had been re-established, ethanol (4-8% w/v) was added to the kool-aid. Fluid delivery was accompanied by a tone and the illumination of a stimulus light above the fluid spout.

A fixed ratio schedule was used for alcohol self-administration with alcohol available during 2 hour session each day of the study. The first session started at 9:00 AM and the second session started at 1:00 PM. The baboons received their daily food ration at noon each day. Each session consisted of twenty 6 minute trials, wherein the availability of alcohol was indicated by the lights above the alcohol lever. The baboons received an aliquot of alcohol (4% w/v, 5 ml) for pulling the lever 10 times (FR10) and the could earn 5 aliquots during each trial. The trial ended after the baboons earned 5 reinforcers or if no response was made for 6 minutes. Trials were separated by a 1 minute interval during which no alcohol was available. Thus 100 aliquots or 500 ml of beverage were available in the morning and afternoon Mondays through Fridays.

SOC-1 Administration

Administered doses of 1 to 8 mg/kg of SOC-1 where given orally to the baboons during the study. The drug, in a powder form, was delivered to the baboons by placing the correct dosage, along with some sugar, in the centre of figs, and feeding these figs to the baboons 60 minutes before the daily session. The drug or a placebo was given acutely no more than twice a week.

Figure 17:
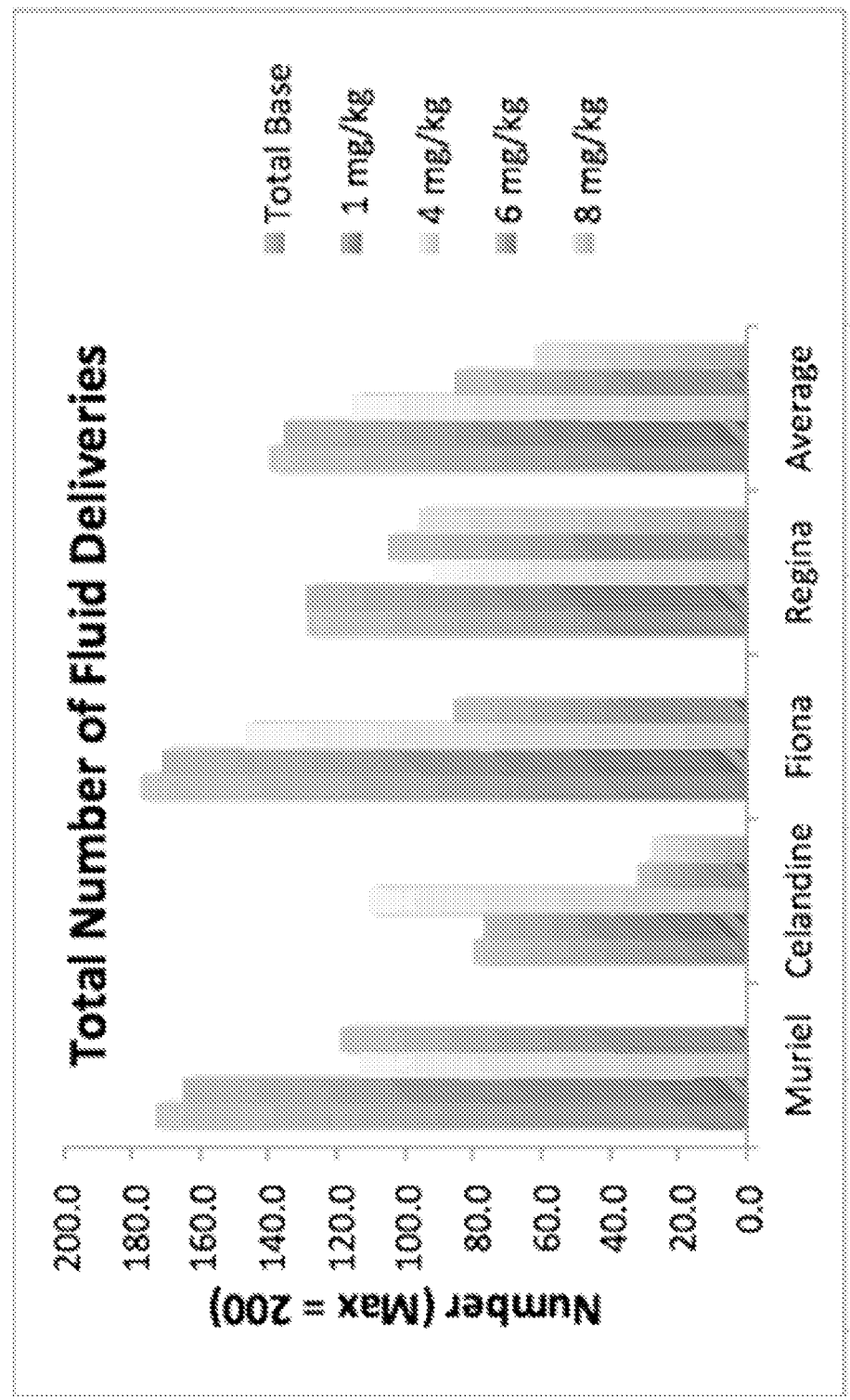
FIG. 17—Total number of fluid deliveries for baboons during a study focusing on alcohol intake versus various concentrations of SOC-1 being administered to said baboons and overall average.
Figure 18:
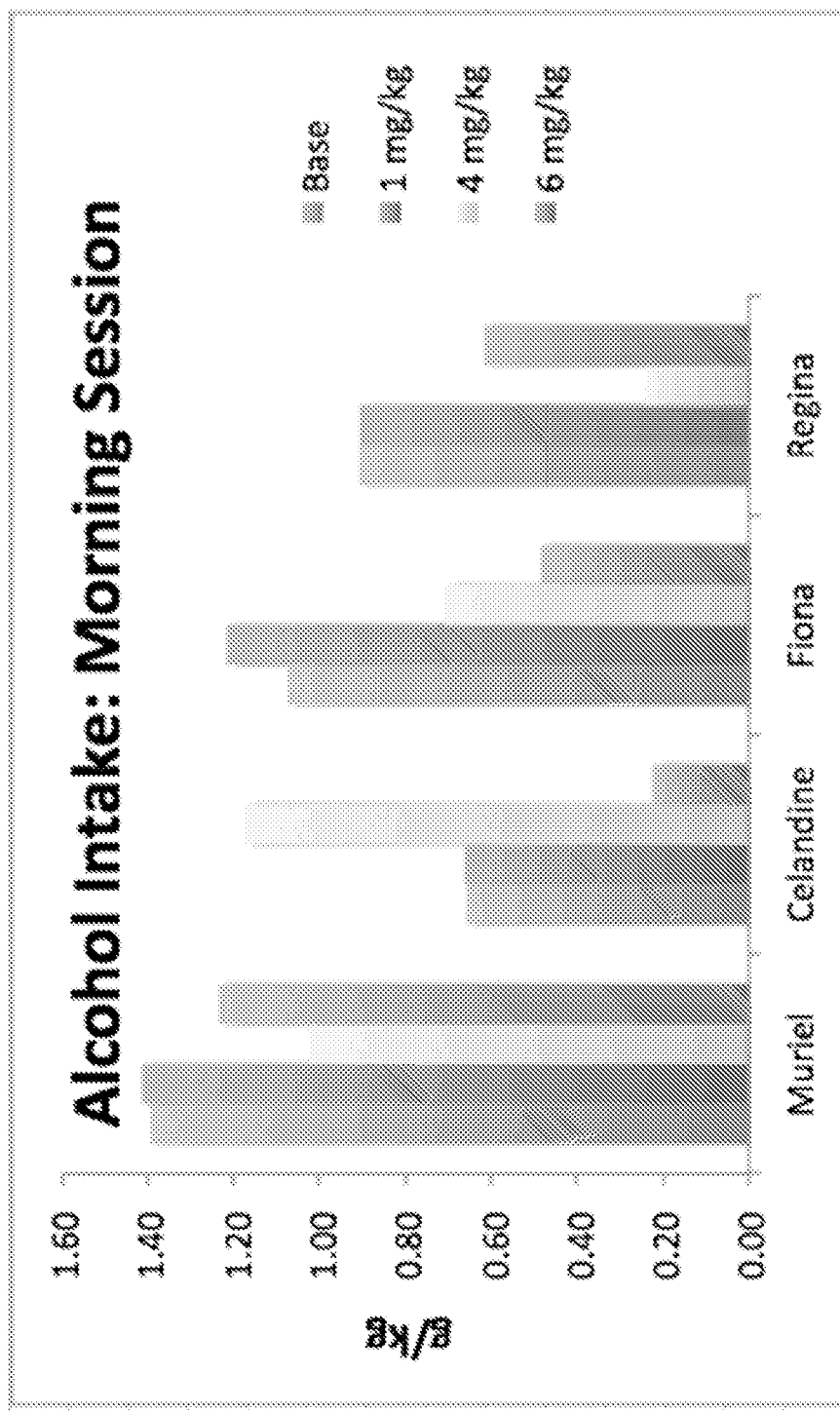
FIG. 18—The intake of alcohol for baboons and the average during morning sessions for baboons being administered various doses of SOC-1.
Figure 19:
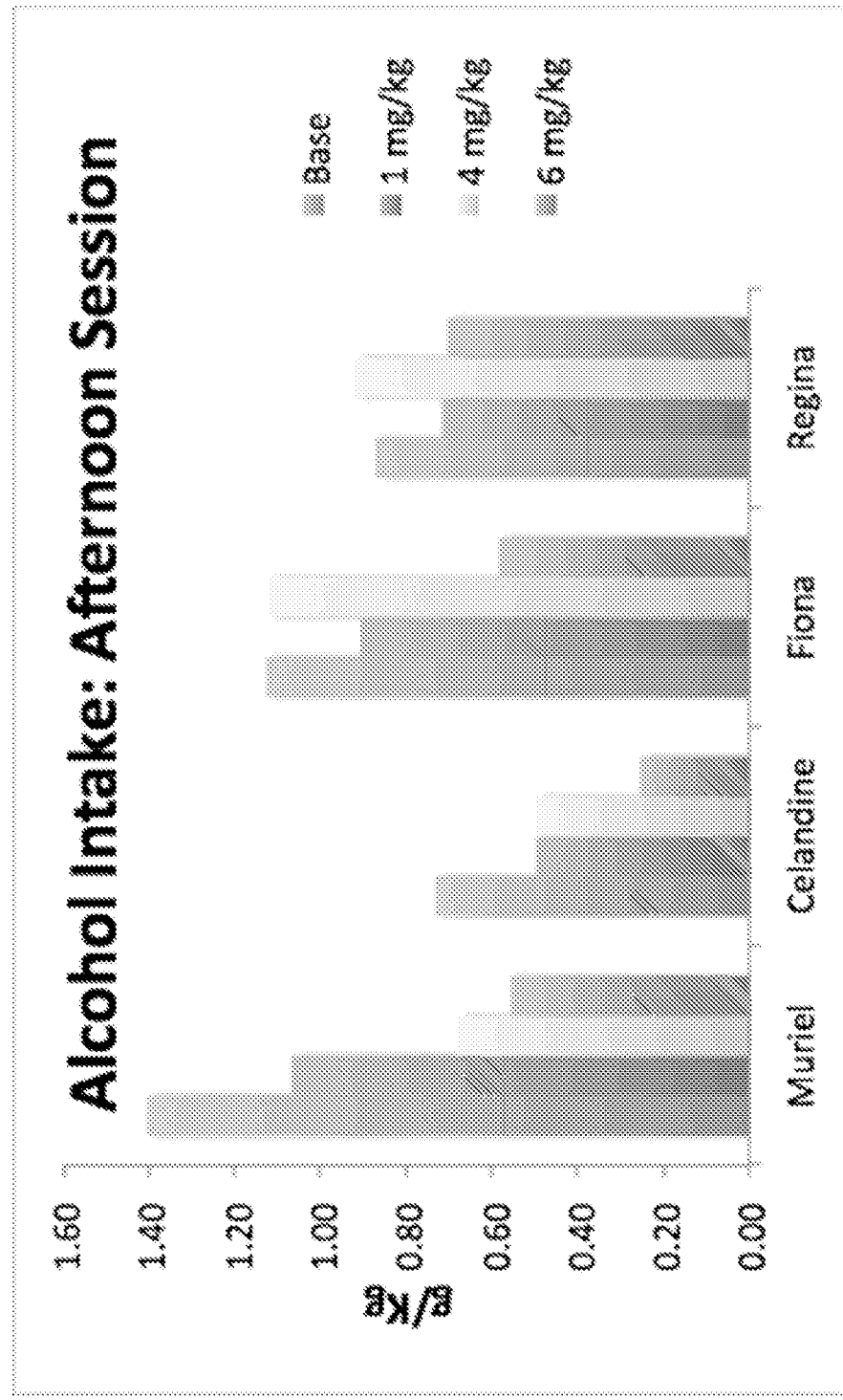
FIG. 19—The intake of alcohol for baboons and the average during afternoon sessions for baboons being administered various doses of SOC-1.

The results of the study are shown in FIG. 17, FIG. 18 and FIG. 19. FIG. 17 shows total number of fluid deliveries as a function of SOC-1 dose. FIG. 18 and FIG. 19 show the results for morning and afternoon intake expressed as alcohol intake, respectively.

Example 13—Assessment of Autism Spectrum Disorders in a BALB/C Mouse Model

Figure 20:
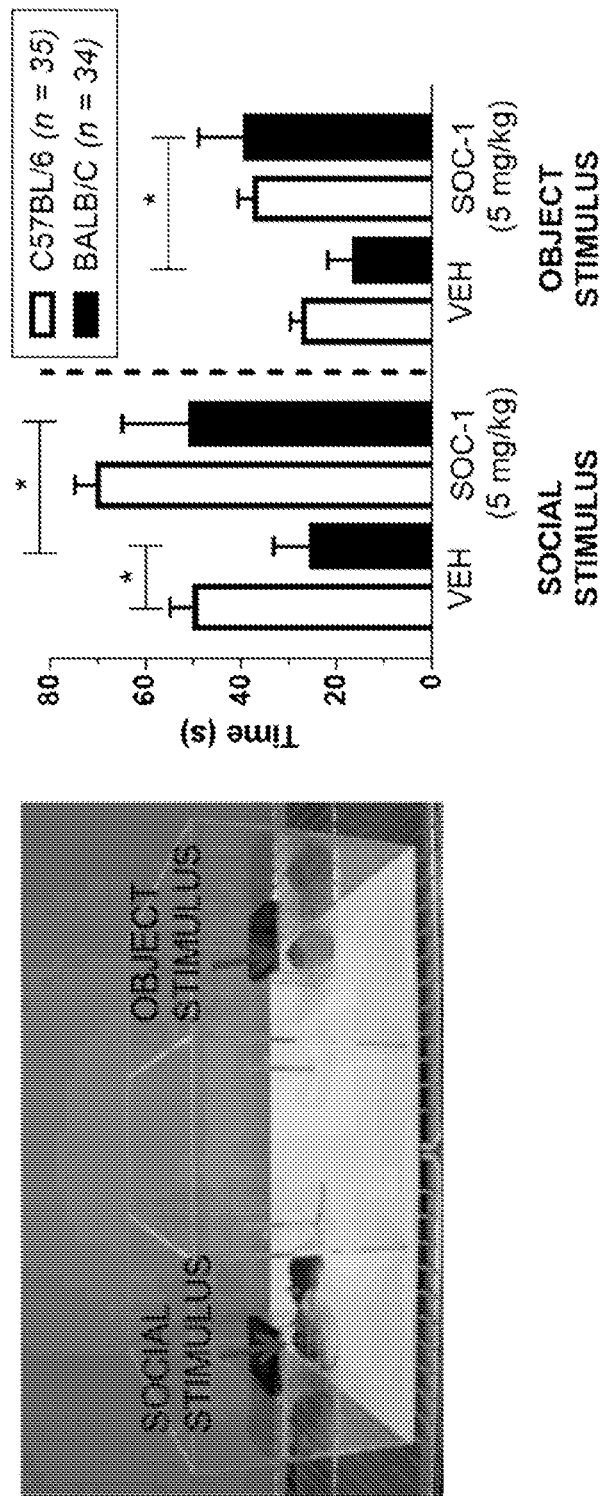
FIG. 20—Results of an autism spectrum disorder study using BALB/C mice administered SOC-1.

BALB/C mice have autistic-like behaviours (including reduced interest in social stimuli) compared to standard C57BL/6 mice. In a social preference test, BALB/C mice show no preference for interacting with a social stimulus (a novel mouse) over an object stimulus (a novel object), whereas C57BL/6 mice show a robust preference. SOC-1 (5 mg/kg IP) significantly increased the amount of time BALB/C mice spent investigating the social stimulus, to the point that they no longer differed from the standard strain C57BL/6 mice. SOC-1 (5 mg/kg IP) also significantly increased the amount of time the BALB/C mice spent investigating the object stimulus, suggesting that in addition to increasing interest in social stimuli, it may also cause a more general increase in exploratory behaviour. The results of the study are shown in FIG. 20.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of treating a substance abuse disorder in a subject,
   wherein the substance abuse disorder relates to a drug or chemical substance selected from cocaine, opiates, amphetamines, heroin, alcohol and nicotine,
   the method comprising administering to a subject in need thereof an effective amount of a compound of Formula (Ia), or a pharmaceutically acceptable salt thereof:

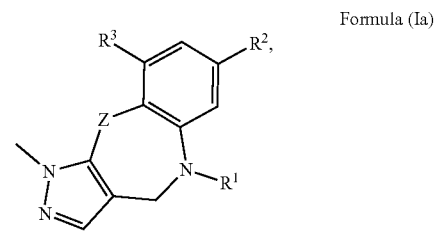

Formula (Ia)

wherein:
   Z is selected from: NH;
   $R^1$ is selected from H or $C(O)R^4$;
   $R^2$ is selected from: H, OH, a halogen, an optionally substituted $C_{1-5}$ alkyl, or an optionally substituted $OC_{1-5}$ alkyl;
   $R^3$ is selected from: H, OH, a halogen, an optionally substituted $C_{1-5}$ alkyl, or an optionally substituted $OC_{1-5}$ alkyl; and
   $R^4$ is an optionally substituted $C_{1-5}$ alkyl.

2. The method of claim 1, comprising administering the compound of formula (Ia) or pharmaceutically acceptable salt thereof by a route selected from: orally, rectally, nasally, topically, parenterally, inhalation, or insufflation.

3. The method of claim 1, wherein $R^1$ is H.

4. The method of claim 1, wherein $R^2$ is H.

5. The method of claim 1, wherein $R^3$ is H.

6. The method of claim 1, wherein each of $R^1$, $R^2$ and $R^3$ are H.

7. The method of claim 1, wherein the compound is selected from the group consisting of:

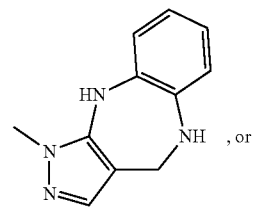 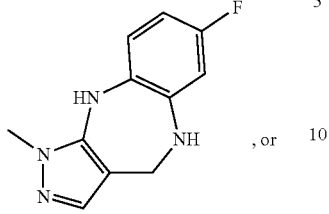

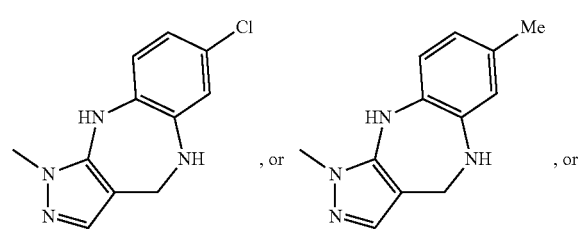

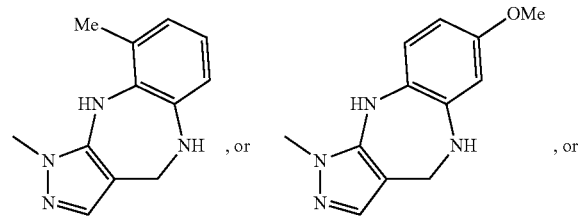

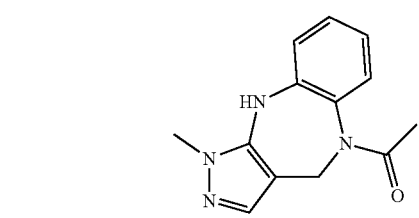

or a pharmaceutically acceptable salt thereof.

8. The method of claim 1, wherein the compound is:

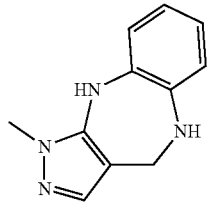

or a pharmaceutically acceptable salt thereof.

9. The method of claim 1, comprising administering the compound in the form of a free base.

10. The method of claim 1, comprising administering the compound in the form of a pharmaceutically acceptable salt.

11. The method of claim 10, wherein the pharmaceutically acceptable salt is selected from the group consisting of: hydrochloric, sulfuric, phosphoric, nitric, carbonic, boric, sulfamic, hydrobromic acids, acetic, propionic, butyric, tartaric, maleic, hydroxymaleic, fumaric, isethionic, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acid salts; or metal salts, including sodium, potassium, lithium, calcium, magnesium and zinc metal salts; or ammonium, alkylammonium salts; or amino acid salts.

12. The method of claim 1, comprising administering the compound or pharmaceutically acceptable salt thereof in the form of a pharmaceutical composition optionally comprising a pharmaceutically acceptable carrier, diluent and/or excipient.

13. The method of claim 1, wherein the substance abuse disorder is abuse of an opiate.

14. The method of claim 1, wherein the substance abuse disorder is abuse of cocaine.

15. The method of claim 1, wherein the substance abuse disorder is abuse of methamphetamine.

16. The method of claim 1, wherein the substance abuse disorder is abuse of alcohol.

17. The method of claim 1, wherein the subject is one who suffers from the substance abuse disorder.

18. The method of claim 1, wherein the subject is recovering from the substance abuse disorder and is seeking to maintain ongoing abstinence from the substance.

* * * * *